United States Patent
Niwa et al.

(10) Patent No.: US 6,350,762 B1
(45) Date of Patent: Feb. 26, 2002

(54) DIHYDROPYRIDINE DERIVATIVE

(75) Inventors: Seiji Niwa; Seiji Ohno; Tomoyuki Onishi; Morikazu Kito; Akira Takahara; Yukitsugu Ono; Hisayuki Uneyama, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/403,575
(22) PCT Filed: Dec. 22, 1998
(86) PCT No.: PCT/JP98/05801
   § 371 Date: Oct. 25, 1999
   § 102(e) Date: Oct. 25, 1999
(87) PCT Pub. No.: WO99/32446
   PCT Pub. Date: Jul. 1, 1999

(30) Foreign Application Priority Data

Dec. 22, 1997 (JP) ............................................. 9-353370
Oct. 23, 1998 (JP) ........................................... 10-303067

(51) Int. Cl.[7] ..................... A61K 31/444; C07D 401/04
(52) U.S. Cl. .................... 514/334; 546/257; 546/283.4; 546/194; 546/276.4; 546/310; 546/316; 544/124; 544/360; 514/336; 514/355; 514/356
(58) Field of Search ................................ 514/334, 336, 514/355, 356; 546/257, 283.4, 316, 116, 194, 272.7, 276.4, 310; 544/124, 360

(56) References Cited

U.S. PATENT DOCUMENTS

| 4,616,002 A | 10/1986 | Kamber et al. |
| 5,767,129 A | 6/1998 | Yuen |
| 5,767,131 A * | 6/1998 | Gluchowski et al. ........ 514/318 |

FOREIGN PATENT DOCUMENTS

| EP | 0 520 200 | 12/1992 |
| EP | 0 622 364 | 11/1994 |
| JP | 63-233058 | 11/1985 |
| JP | 8-41052 | 2/1996 |
| WO | WO 93/13128 | 7/1993 |
| WO | WO 98/49144 | 11/1998 |
| WO | WO 99/43658 | 9/1999 |
| WO | WO 00/24716 | 5/2000 |

OTHER PUBLICATIONS

V.D. Monje, et al., Neuropharmacology, vol. 32, No. 11, pp. 1141–1149, "A New Conus Peptide Ligand for Ca Channel Subtypes," 1993.

H. Uneyama, et al., British Journal of Pharmacology, vol. 122, pp. 37–42, "Blockade of N–Type $Ca^{2+}$ Current by Cilnidipine (FRC–8653) in Acutely Dissociated Rat Sympathetic Neurones," 1997.

S. Fujii, et., The Journal of Pharmacology and Experimental Therapeutics, vol. 280, No. 3, pp. 1184–1191, "Effect of Cilnidipine, A Novel Dihydropyridine $Ca^{++}$–Channel Antagonists, on N–Type $Ca^{++}$ Channel in Rat Dorsal Root Ganglion Neurons," 1997.

D. Nagarathnam, et al., J. Med. Chem., vol. 41, pp. 5320–5333, "Design and Synthesis of Novel $\alpha_{1a}$ Adrenoceptor–Selective Dihydropyridine Antagonists for the Treatment of Benign Prostatic Hyperplasia," 1998.

W.C. Wong, et al., J. Med. Chem. vol. 41, pp. 2643–2650, "Identification of a Dihydropyridine as a Potent $\alpha_{1a}$ Adrenoceptor–Selective Antagonist that Inhibits Phenylephrine–Induced Contraction of the Human Prostate," 1998.

* cited by examiner

Primary Examiner—Charanjit S. Aulakh
(74) Attorney, Agent, or Firm—Oblon, Spivak, McClelland, Maier & Neustadt, P.C.

(57) ABSTRACT

Dihydropyridine derivatives of the following formula, analogs thereof and pharmaceutically acceptable salts thereof have an activity of selectively inhibiting the action of N-type calcium channel. They are used as remedies for various diseases relating to the N-type calcium channel.

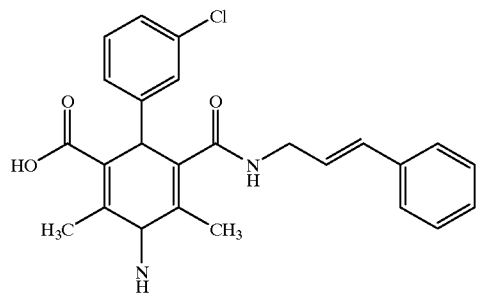

40 Claims, No Drawings

DIHYDROPYRIDINE DERIVATIVE

BACKGROUND OF THE INVENTION

The present invention relates to new dihydropyridine derivatives, and the use of the dihydropyridine derivatives as medicines. It is said that the activation of N-type calcium channel is concerned with diseases such as encephalopathies caused by the ischemia in the acute phase after the onset of cerebral infarction, cerebral hemorrhage (including subarachnoidal bleeding) or the like; progressive neurodegenerative diseases, e. g. Alzheimer's disease; AIDS related dementia; Parkinson's disease; dementia caused by cerebrovascular disorders and ALS; neuropathy caused by head injury; various pains, e. g. sharp pain caused by spinal injury, diabetes or thromboangitis obliterans; pain after an operation; migraine and visceral pain; various diseases caused by psychogenic stress, e. g. bronchial asthma; unstable angina and hypersensitive colon inflammation; emotional disorder; and drug addiction withdrawal symptoms, e. g. ethanol addiction withdrawal symptoms. The compounds of the present invention are effective in inhibiting the activation of N-type calcium channel and, therefore, they are usable as remedies for the above-described diseases.

The calcium channels are now classified into subtypes L, N, P, Q, R and T. Each of the subtypes is distributed specifically to organs. Particularly, it is known that N-type calcium channel is widely distributed in the central nerves, peripheral nerves and adrenal medulla cells and that this calcium channel is concerned with the death of neurons, control of blood catecholamine dynamics and control of senses such as perceptivity.

It was confirmed that peptides, omega conotoxin GVIA and omega conotoxin MVIIA which selectively inhibit the function of N-type calcium channel inhibit the release of excitatory neurotransmitter from a brain slice sample. It was confirmed by animal experiments that they prevent the advancement of neuron necrosis in a cerebrovascular disorder. It is generally considered that a compound having a clinical effect of inhibiting the function of N-type calcium channel is effective in curing encephalopathies caused by the ischemia in the acute phase after the onset of cerebral infarction, cerebral hemorrhage (including subarachnoidal bleeding) or the like; progressive neurodegenerative diseases, e. g. Alzheimer's disease; AIDS related dementia; Parkinson's disease; dementia caused by cerebrovascular disorders and ALS; neuropathy caused by head injury. In addition, it was also confirmed by animal experiments that omega conotoxin MVIIA gets rid of formalin-caused sharp pain, hot plate pain, sharp pain caused by peripheral neuropathy, etc. Therefore, this medicine is considered to be clinically effective for relieving various pains such as sharp pain caused by spinal injury, diabetes or thromboangitis obliterans; pain after an operation; migraine; and visceral pain. Further, omega conotoxin GVIA inhibits the release of catecholamine from cultured sympathetic ganglion cells, the constriction reaction of an isolated blood vessel by the electric stimulation of governing nerves, and the acceleration of catecholamine secretion from dog adrenal medulla, etc. Therefore, it is considered that compounds having the N-type calcium channel-inhibiting activity are clinically effective in treating various diseases caused by psychogenic stress, e. g. bronchial asthma, unstable angina and hypersensitive colon inflammation [Neuropharmacol., 32, 1141 (1993)].

Although several peptide compounds and non-peptide compounds which selectively react on the N-type calcium channel have been disclosed hitherto (for example, WO 9313128), they are not yet used as practical medicines. Some of known compounds which react on the N-type calcium channel also react on other calcium channels than the N-type calcium channel [British Journal of Pharmacology, 122 (1), 37–42, 1997]. For example, compounds which are also antagonistic to L-type calcium channel, which deeply concern with the hypotensive effect, were incompatible with diseases for which N-type antagonists are efficacious (such as cerebral stroke, and pain caused of neuralgia, terminal cancer, spinal injury or the like).

DISCLOSURE OF THE INVENTION

An object of the present invention is to provide new compounds having a selectively antagonistic effect on N-type calcium channel.

Another object of the present invention is to provide antagonists to the N-type calcium channel.

Still another object of the present invention is to provide remedies for encephalopathies caused by the ischemia in the acute phase after the onset of cerebral infarction or cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine, visceral pain, bronchial asthma, unstable angina, hypersensitive colon inflammation and drug addiction withdrawal symptoms.

A further object of the present invention is to provide a medicinal composition.

The above-described objects and other objects of the present invention will be apparent from the following description and Examples.

The inventors synthesized various dihydropyridine derivatives, and made investigations on the effects of these newly synthesized compounds and known dihydropyridine derivatives for inhibiting the electric current of N-type calcium channel. After the investigations, the inventors have found that some specified, new dihydropyridine derivatives have excellent, selective antagonistic effect on the N-type calcium channel. The present invention has been completed on the basis of this finding.

Namely, the present invention provides dihydropyridine derivatives of following general formula (1) or pharmaceutically acceptable salts thereof:

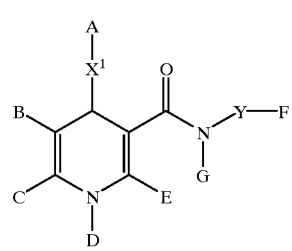

(1)

wherein

A represents a group of following general formula (2), 1-naphthyl group, 2-naphthyl group, thiophene-3-yl group, thiophene-2-yl group, furan-3-yl group, furan-2-yl group, pyridine-4-yl group, pyridine-3-yl group, pyridine-2-yl group, indole-2-yl group or indole-3-yl group:

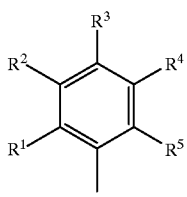
(2)

wherein $R^1$, $R^2$, $R^3$ $R^4$ and $R^5$ may be the same or different from each other, and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group, B represents cyano group, nitro group, acetyl group, tetrazole group, triazole group or a group of following general formula (3) or (4):

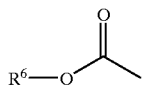
(3)

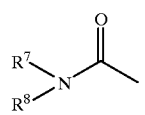
(4)

wherein
$R^6$ to $R^8$ each represent hydrogen atom, a linear or branched, saturated or unsaturated hydrocarbon group having 1 to 6 carbon atoms, an alkyl group substituted with a cyclic alkyl group (which may contain a hetero atom), a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group (excluding pyridine-3-ylpropyl group), a heteroaryl-lower alkenyl group, a cyano-lower alkyl group or a cyano-lower alkenyl group, and the chains in $R^6$ to $R^8$ may have a hetero atom, and $R^7$ and $R^8$ may together form a ring which may contain a hetero atom, C represents hydrogen atom, a lower alkyl group, dimethoxymethyl group, cyano group, a hydroxy-lower alkyl group or a halogeno-lower alkyl group, D represents hydrogen atom, a lower alkyl group, a hydroxy-lower alkyl group or an aryl-lower alkyl group, E represents hydrogen atom, a lower alkyl group, dimethoxymethyl group, cyano group, a hydroxy-lower alkyl group or a halogeno-lower alkyl group, F represents an aryl group, a heteroaryl group or a cyclic alkyl group (which may have a hetero atom), G represents hydrogen atom or a lower alkyl group, $X^1$ represents an interatomic bond, —$CH_2$—, —$CH_2CH_2$—, —CH=CH— or —C≡C—, and Y represents a group of any of following general formulae (5) to (14):

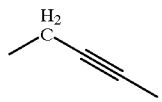
(5)

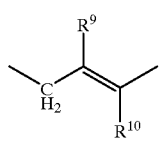
(6)

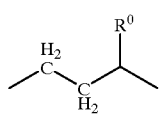
(7)

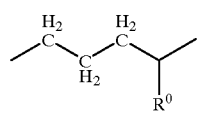
(8)-1

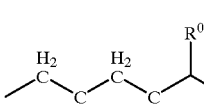
(8)-2

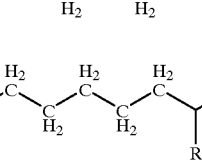
(8)-3

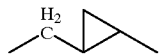
(9)

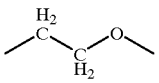
(10)

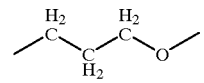
(11)

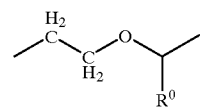
(12)

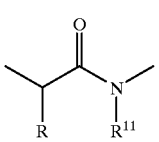
(13)

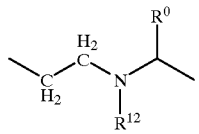

(14)

wherein two of $R^9$ to $R^{12}$ and $R^0$ may be the same or different from each other, and each represent hydrogen atom, a lower alkyl group, a hydroxy-lower alkyl group, a thio-lower alkyl group, an alkylthio-lower alkyl group, an aryl group, an aryl-lower alkyl group or a heteroaryl-lower alkyl group, B and C may together form a lactone ring or lactam ring or two of $R^1$ to $R^3$ may be bonded together to form a ring, and $R^9$ and $R^{10}$ may be bonded together to form a ring.

The present invention also provides an antagonist to the N-type calcium channel, which contains a dihydropyridine derivative of above general formula (1) or general formula (1-1) given below or a pharmaceutically acceptable salt thereof as the active ingredient.

The present invention further provides a medicine containing the above-described dihydropyridine derivative or a pharmaceutically acceptable salt thereof as the active ingredient, and usable for any of encephalopathies caused by the ischemia in the acute phase after the onset of cerebral infarction, cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine and visceral pain, bronchial asthma, unstable angina, hypersensitive colon inflammation, and drug addiction withdrawal symptoms.

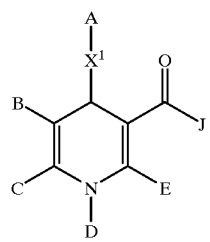

(1-1)

wherein A represents a group of following general formula (2), 1-naphthyl group, 2-naphthyl group, thiophene-3-yl group, thiophene-2-yl group, furan-3-yl group, furan-2-yl group, pyridine-4-yl group, pyridine-3-yl group, pyridine-2-yl group, indole-2-yl group, indole-3-yl group, quinoline-2-yl group, quinoline-3-yl group, quinoline-4-yl group, quinoline-5-yl group, quinoline-6-yl group, quinoline-7-yl group, quinoline-8-yl group, another heteroaryl group, cyclohexyl group, cyclopentyl group or a cyclic alkyl group (which may contain a hetero group), B is as defined above in general formula (1), C represents hydrogen atom, dimethoxymethyl group, cyano group, a lower alkyl group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group, D is as defined above in general formula (1), E represents hydrogen atom, dimethoxymethyl group, cyano group, a lower alkyl group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group, $X^1$ is as defined above in general formula (1), J represents a group of following formulae (J-1) to (J-3):

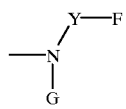

(J-1)

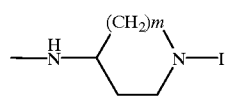

(J-2)

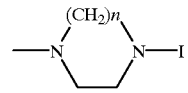

(J-3)

wherein F in formula (J-1) represents an aryl group, a heteroaryl group or a cyclic alkyl group (which may contain a hetero atom), F and G are as defined in general formula (1), Y is as defined in general formula (1), or represents a group of following formula (22) or (23):

(22)

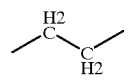

(23)

wherein m in formulae (J-2) and (J-3) represents an integer of 1 to 3, n represents an integer of 2 or 3, I represents an aryl group, a heteroaryl group, a cyclic alkyl group (which may contain a hetero atom) or a group of following formula (Ia):

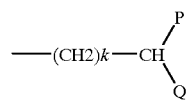

(Ia)

wherein k is 0, 1 or 2, P and Q may be the same or different from each other, and each represent hydrogen atom, a lower alkyl group, a hydroxy-lower alkyl group, a thio-lower alkyl group, an alkylthio-lower alkyl group, an aryl group, an aryl-lower alkyl group, a heteroaryl group or a heteroaryl-lower alkyl group, or P and Q together form a ring which may contain a hetero atom, B and C may together form a lactone ring or lactam ring or two of $R^1$ to $R^3$ may be bonded to form a ring, and $R^9$ and $R^{10}$ may be bonded together to form a ring.

The present invention also provides a medicinal composition containing the above-described dihydropyridine derivative of general formula (1) or a pharmaceutically acceptable salt thereof, a carrier and/or a diluent.

BEST MODE FOR CARRYING OUT THE INVENTION

The term "lower" in, for example, lower alkyl groups, herein indicates that the groups have 1 to 6 carbon atoms. The alkyl groups themselves and the alkyl groups in the alkoxyl, alkenyl, alkylamino, alkylthio and alkanoyl groups may be either linear or branched. The alkyl groups are, for example, methyl group, ethyl group, propyl group, isopropyl group, butyl group and secondary and tertiary butyl groups. Among them, those having 1 to 3 carbon atoms are preferred. The aryl-lower alkoxyl groups include, for example, benzyloxy group. The halogen atoms indicate fluorine, chlorine, bromine and iodine atoms. Examples of the aryl groups herein include substituted and unsubstituted aryl groups, preferably substituted or unsubstituted phenyl groups, and the substituents thereof are particularly preferably halogens, alkyl groups and alkoxyl groups. The heteroaryl groups are substituted or unsubstituted heteroaryl groups, such as preferably, pyridyl group, furyl group, and substituted pyridyl and furyl groups. Particularly preferred examples of the substituents are halogens, alkyl groups and alkoxyl groups. Examples of the aroyl groups include benzoyl group and pyridylcarbonyl group.

The substituents of the substituted aryl groups or substituted heteroaryl groups in $R^6$ to $R^8$ in the groups represented by general formula (3) or (4) are, for example, halogen atoms (such as fluorine, chlorine, bromine and iodine), hydroxyl group, carboxyl group, cyano group, nitro group, lower alkyl groups, lower alkoxyl groups, halogeno-lower alkyl groups and lower alkoxycarbonyl groups.

1-Naphthyl group, 2-naphthyl group, indole-2-yl group and indole-3-yl groups represented by A in general formula (1) are either unsubstituted or substituted, and the substituents of them are the same as those described above with reference to $R^6$ to $R^8$.

Thiophene-3-yl group, thiophene-2-yl group, furan-3-yl group, furan-2-yl group, pyridine-4-yl group, pyridine-3-yl group and pyridine-2-yl group represented by A are also unsubstituted or substituted. When they have two or more substituents, the substituents may form a ring together. The substituents are those described above with reference to 1-naphthyl group. The rings formed by those substituents include benzothiophene, benzofuran, quinoline, isoquinoline, etc.

Quinoline-2-yl group, quinoline-3-yl group, quinoline-4-yl group, quinoline-5-yl group, quinoline-6-yl group, quinoline-7-yl group and quinoline-8-yl group represented by A in general formula (1-1) are either unsubstituted or substituted, and the substituents of them are the same as those described above with reference to 1-naphthyl group or the like. Heteroaryl groups, cyclohexyl group, cyclopentyl group and other cyclic alkyl groups are also unsubstituted or substituted. When they have two or more substituents, these substituents may form a ring together. The substituents are those described above with reference to 1-naphthyl group. The rings formed by these substituents include acridine, benzothiazole, benzoxazole, tetrahydronaphthalene, indan, etc.

The heteroaryl groups and other cyclic alkyl groups include, for example, thiazole, oxazole, pyrimidine, pyrazine and pyridazine; and cyclopropyl, cyclobutyl, cycloheptyl and cyclooctyl groups.

The groups other than those described above as groups represented by A in above general formula (1-1) are the same as those represented with reference to groups represented by A in general formula (1).

The lower alkyl groups, hydroxy-lower alkyl groups, halogeno-lower alkyl groups, amino-lower alkyl groups, azido-lower alkyl groups, aryl-lower alkyl groups and heteroaryl-lower alkyl groups may contain a hetero atom in their chains. The hetero atoms include oxygen, nitrogen and sulfur atoms, and the chains containing the hetero atoms are, for example, hydroxyethoxymethyl group, methoxyethyl group, aminoethoxymethyl group, azidoethoxymethyl group and methylthioethyl group.

F in general formula (1) is preferably a group of following formula (15), thiophene-3-yl group, thiophene-2-yl group, furan-3-yl group, furan-2-yl group, pyridine-4-yl group, pyridine-3-yl group, pyridine-2-yl group, cyclohexyl group, pyrrolidine-1-yl group, morpholine-4-yl group, imidazole-1-yl group or pyrrolidinone-1-yl group:

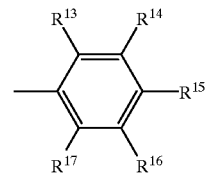

(15)

wherein $R^{13}$, $R^{14}$, $R^{15}$ $R^{16}$ and $R^{17}$ may be the same or different from each other, and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, carbamoyl which may have a substituent, a carboxyamide group which may have a substituent, an aroyl group, an aryl group, a heteroaryl group or a saturated cyclic hydrocarbon group having 3 to 8 carbon atoms, which may have a hetero atom in its chain if necessary; and two of $R^{13}$ to $R^{15}$ may be bonded together to form a ring.

Thiophene-3-yl group, thiophene-2-yl group, furan-3-yl group, furan-2-yl group, pyridine-4-yl group, pyridine-3-yl group, pyridine-2-yl group, cyclohexyl group and pyrrolidine-1-yl group may be either unsubstituted or substituted. When they have two or more substituents, they may form a ring together. The substituents are those described above with reference to $R^6$ to $R^8$. The rings formed by those substituents are, for example, those described above with reference to group A.

F in general formula (1-1) is preferably a group of above formula (15), thiophene-3-yl group, thiophene-2-yl group, furan-3-yl group, furan-2-yl group, pyridine-4-yl group, pyridine-3-yl group, pyridine-2-yl group, imidazole-1-yl group, another heteroaryl group, piperidine-1-yl group, piperidine-4-yl group, pyrrolidine-1-yl group, pyrrolidine-3-yl group, piperidinone-1-yl group, pyrrolidinone-1-yl group, piperazine-1-yl group, morpholine-4-yl group, or a cyclic alkyl group having 3 to 8 carbon atoms such as cyclohexyl group or cyclopentyl group.

The heteroaryl group, pyrrolidine-3-yl group, piperazine-1-yl group, piperidine-4-yl, piperidine-1-yl, pyrrolidine-1-yl, cyclopentyl group, morpholine-4-yl group and cyclic alkyl groups having 3 to 8 carbon atoms may be unsubstituted or substituted. When they have two or more substituents, these substituents may form a ring together. The substituents are those described above with reference to F in above general formula (1). The rings formed by these substituents are, for example, those described above with reference to group A, and tetrahydroisoquinoline Furthermore, the meaning of F in the formula (1-1) is the same as that of F in the formula (1).

Preferred substituents in general formulae (1) and (1-1) in the present invention are as described below.

A is preferably a group of general formula (2), 1-naphthyl group, 2-naphthyl group, thiophene-3-yl group, thiophene-2-yl group, furan-3-yl group, furan-2-yl group, pyridine-4-yl group, pyridine-3-yl group or pyridine-2-yl group.

B is preferably a group of general formula (3) [particularly preferably a group of general formula (3) wherein $R^6$ represents hydrogen atom, an aryl-lower alkenyl group, a heteroaryl-lower alkenyl group or a cyano-lower alkyl group], a group of general formula (4) [particularly preferably a group of general formula (4) wherein either $R^7$ or $R^8$ represents hydrogen atom], or a group, which is condensed with C to form a lactone ring, such as cyano group, nitro group, acetyl group, tetrazole group or triazole group.

C is preferably hydrogen atom, a lower alkyl group, cyano group, chloromethyl group, hydroxymethyl group, hydroxyethoxymethyl group or aminoethoxymethyl group.

D is preferably hydrogen atom, a lower alkyl group, a hydroxy-lower alkyl group or aryl-lower alkyl group.

E is preferably hydrogen atom, a lower alkyl group, cyano group, chloromethyl group, hydroxymethyl group, hydroxyethoxymethyl group or aminoethoxymethyl group. $X^1$ is preferably an interatomic bond, —CH=CH— or —C≡C—, and F is preferably a group of general formula (15), thiophene-3-yl group, thiophene-2-yl group, furan-3-yl group, furan-2-yl group, pyridine-4-yl group, pyridine-3-yl group, pyridine-2-yl group, imidazole-1-yl group, another heteroaryl group, piperidine-1-yl group, piperidine-4-yl group, pyrrolidine-1-yl group, pyrrolidine-3-yl group or morpholine-4-yl group. G is preferably hydrogen atom or a lower alkyl group.

Y is preferably a group of any of general formulae (5) to (7), (8)-1 and (9)–(14). $R^0$ is preferably hydrogen atom. Among these groups, preferred groups are those represented by general formula (6) wherein $R^9$ and $R^{10}$ are particularly preferably hydrogen atom, and those represented by general formulae (7), (8)-1, (8)-2 or (8)-3 wherein $R^0$ is particularly preferably hydrogen atom.

J is preferably a group represented by general formula (J-1) wherein G, Y and F are preferably those described above for general formula (1).

I is preferably an aryl-lower alkyl group, a heteroaryl-lower alkyl group, an aryl group or a heteroaryl group.

In the present invention, Y in general formula (1) is preferably a group represented by general formula (6).

Preferably in general formula (1), D is hydrogen atom, G is hydrogen atom, $X^1$ is an interatomic bond, and Y is a group of general formula (6) wherein $R^9$ and $R^{10}$ are each hydrogen atom.

Preferably in general formula (1), B is a group of general formula (3), a group of general formula (4) wherein either $R^7$ or $R^8$ represents hydrogen atom, or a group which is condensed with C to form a lactone ring, D is hydrogen atom, G is hydrogen atom, $X^1$ is an interatomic bond, and Y is a group of general formula (6) wherein $R^9$ and $R^{10}$ are each hydrogen atom.

Preferably in general formula (1), B is a group of general formula (3) wherein $R^6$ represents hydrogen atom, D is hydrogen atom, G is hydrogen atom, $X^1$ is an interatomic bond, and Y is a group of general formula (6) wherein $R^9$ and $R^{10}$ are each hydrogen atom.

Preferably in general formula (1), B is a group of general formula (3) wherein $R^6$ represents hydrogen atom, or a group of general formula (4) wherein $R^7$ or $R^8$ each represents hydrogen atom, D is hydrogen atom, G is hydrogen atom, $X^1$ is an interatomic bond, and Y is a group of general formula (7), (8)-1, (8)-2 or (8)-3 wherein $R^0$ is particularly preferably hydrogen atom. More preferably, B is a group of general formula (3) wherein $R^6$ represents hydrogen atom.

Preferably in general formula (1), B is a group of general formula (3) wherein $R^6$ represents a group other than hydrogen atom, D is hydrogen atom, G is hydrogen atom, $X^1$ is an interatomic bond, and Y is a group of general formula (7), (8)-1, (8)-2 or (8)-3 wherein $R^0$ is particularly preferably hydrogen atom.

Preferably in general formula (1), B is a group of general formula (3) wherein $R^6$ represents an aryl-lower alkenyl group, a heteroaryl-lower alkenyl group or a cyano-lower alkyl group, D is hydrogen atom, G is hydrogen atom, $X^1$ is an interatomic bond, and Y is a group of general formula (7), (8)-1, (8)-2 or (8)-3 wherein $R^0$ is particularly preferably hydrogen atom.

Preferably in general formula (1), A is a group of general formula (2), B is a group of general formula (3) wherein $R^6$ represents hydrogen, D is hydrogen atom, F is a group of general formula (15), G is hydrogen atom, $X^1$ is an interatomic bond, and Y is a group of general formula (6) wherein $R^9$ and $R^{10}$ are each hydrogen atom.

Preferably in general formula (1-1), A is a group of general formula (2), B is a group of general formula (3) wherein $R^6$ represents hydrogen, D is hydrogen atom, and J is a group of general formula (J-2) wherein m represents 2 and I represents benzyl group or a group of general formula (J-3) wherein n represents 2, and I represents phenyl group.

Among the compounds of general formula (1), those of following general formula (1-a) are preferred:

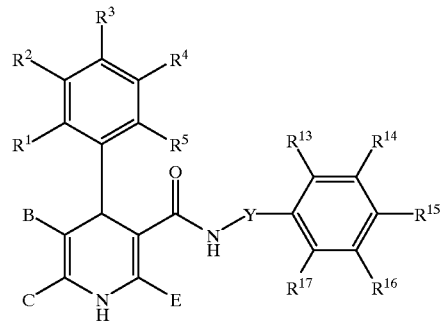

wherein
 $R^1$, $R^2$, $R^3$, $R^4$ and $R^5$ are as defined above,
 B represents a group of above general formula (3) or (4) wherein $R^6$ to $R^8$ are as defined above,
 C and E each represent a lower alkyl group,
 $R^{13}$ to $R^{17}$ are as defined above, and
 Y is represented by above general formula (6) or (7) wherein $R^0$ is preferably hydrogen atom, and $R^9$ and $R^{10}$ are each hydrogen atom.

In the present invention, preferred dihydropyridine derivatives are those of general formula (1-a) or pharmaceutically acceptable salts thereof, wherein B is represented by above general formula (3) wherein $R^6$ represents hydrogen atom, C and E are each methyl group, and Y is represented by above general formula (6) wherein $R^9$ and $R^{10}$ each represent hydrogen atom.

The dihydropyridine derivatives (1) of the present invention can be produced by processes described below.

For example, dihydropyridine derivatives (1-2) wherein B is carboxyl group general formula (3) wherein $R^6$ represents hydrogen atom, C and E are each methyl group and D is hydrogen atom can be produced as follows:

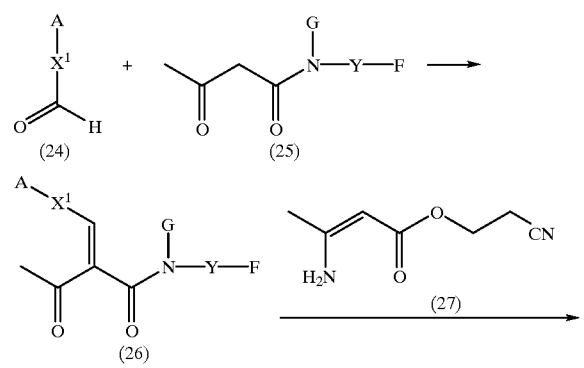

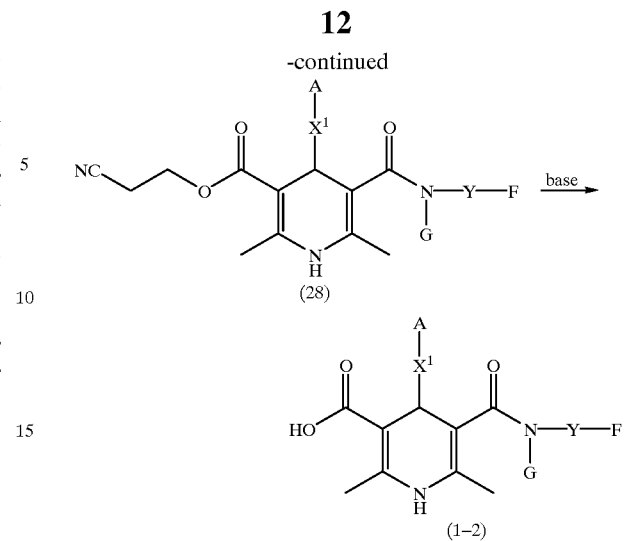

Namely, a compound (26) obtained by Knoevenagel reaction of an aldehyde (24) and an acetoacetamide (25) is reacted with 2-cyanoethyl 3-aminocrotonate (27) to obtain a compound (28), which is then treated with a base such as sodium hydroxide to obtain a dihydropyridine derivative (1-2) of the present invention. Further, the compound (28) can be obtained also by directly reacting the aldehyde (24) with the acetoacetamide (25) and 2-cyanoethyl 3-aminocrotonate (27).

Further, dihydropyridine derivatives (1-2) can be obtained as follows:

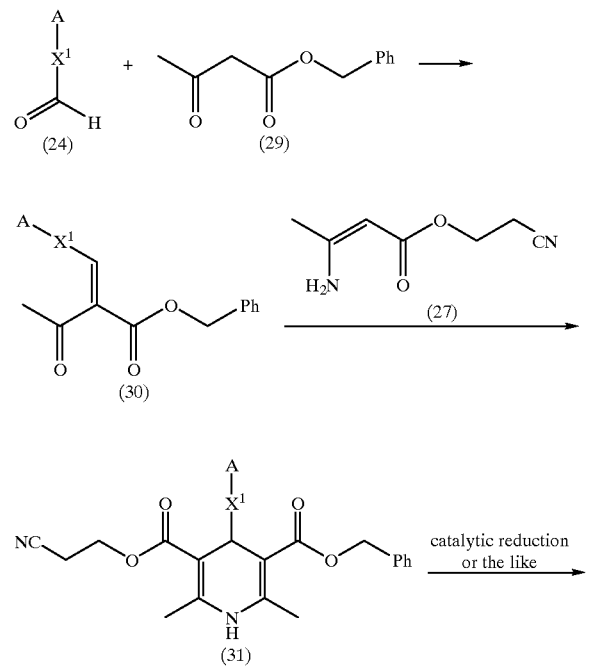

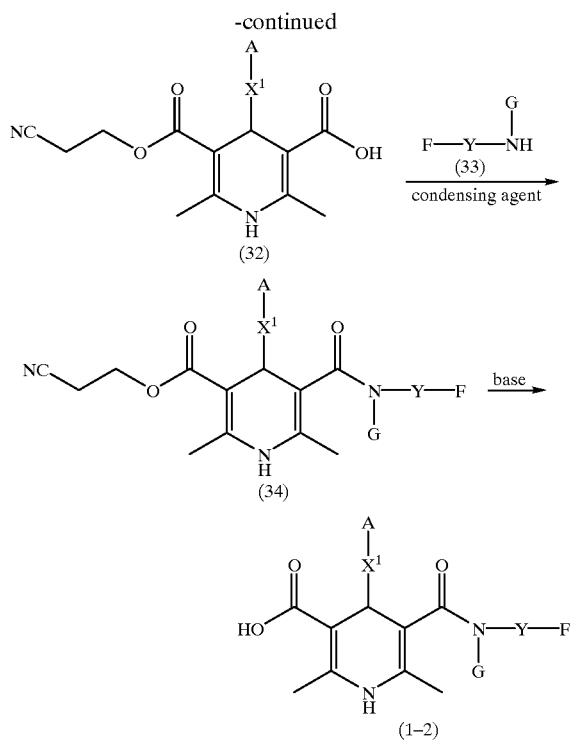

Namely, a compound (30) is obtained by Knoevenagel reaction of an aldehyde (24) and benzyl acetoacetate (29). This compound is reacted with 2-cyanoethyl 3-aminocrotonate (27) to obtain a dihydropyridine derivative (31), which is then converted into a compound (32) by, for example, the catalytic reduction. The compound (32) is condensed with an amine (33) to obtain an amide derivative (34), which is treated with a base such as sodium hydroxide to obtain a dihydropyridine derivative (1-2) of the present invention. Further, dihydropyridine derivatives (1-3), wherein B is an ester group of general formula (3) wherein $R^6$ is a substituent other than hydrogen atom, C and E are each methyl group, and D is hydrogen atom, can be produced as follows:

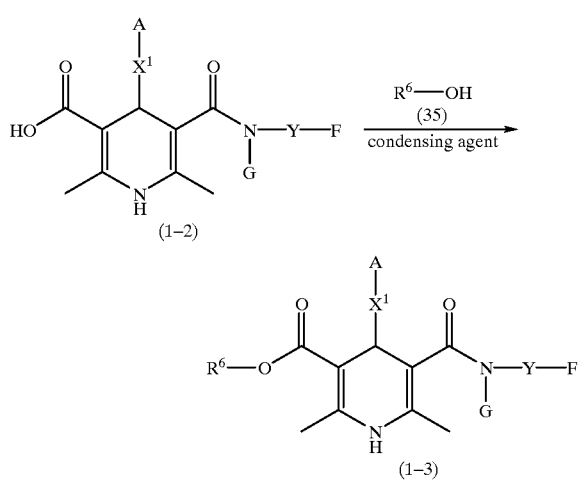

Namely, the dihydropyridine derivative (1-2) synthesized by the above-described method is reacted with an alcohol (35) to obtain a dihydropyridine derivative (1-3) of the present invention.

Dihydropyridine derivatives (1-4) of the above formula wherein B is a substituted carbamoyl group of general formula (4), C and E each represent methyl group, and D is hydrogen atom can be obtained as follows:

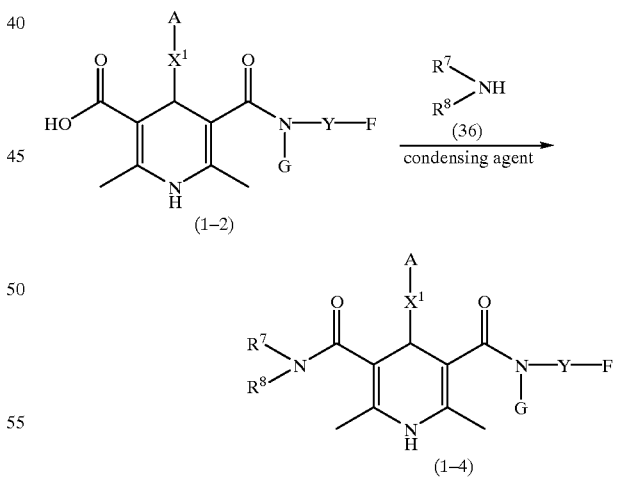

Namely, the dihydropyridine derivative (1-2) synthesized by the above-described method is condensed with a substituted amine (36) to obtain a dihydropyridine derivative (1-4) of the present invention.

Dihydropyridine derivatives (1-5) of the above formula wherein B is a cyano group, C and E each represent methyl group, and D is hydrogen atom can be obtained as follows:

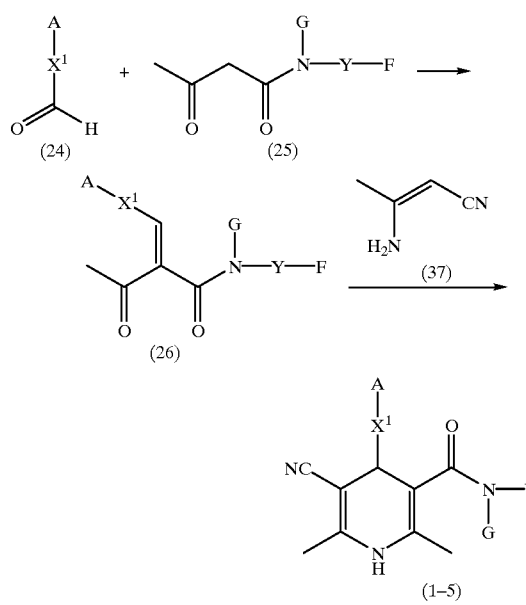

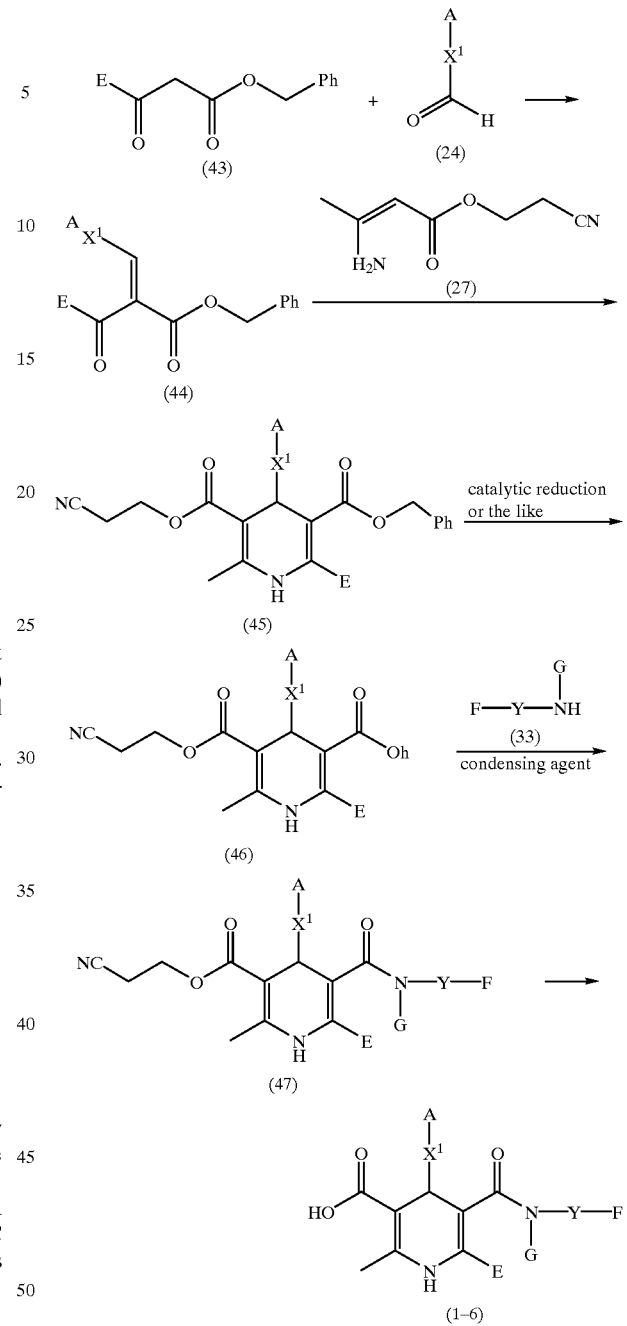

Namely, a dihydropyridine derivative (1-5) of the present invention can be produced by reacting a compound (26) [obtained by Knoevenagel reaction of an aldehyde (24) and an acetoacetamide (25)] with 3-aminocrotonitrile (37).

When the acetoacetamides (25) used as the starting material are not well-known, they can be produced by, for example, the following method:

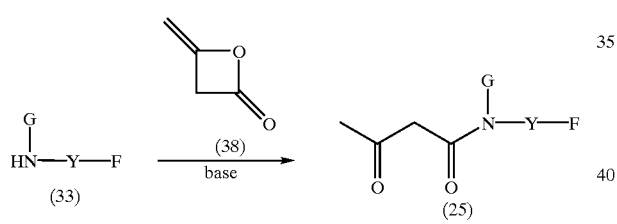

For example, the acetoacetamides (25) can be obtained by heating an amine (33) and a diketene (38) with a suitable base.

Dihydropyridine derivatives (1-6) wherein B is carboxyl group [general formula (3) wherein $R^6$ is hydrogen atom], C is methyl group and D is hydrogen atom can be produced as follows:

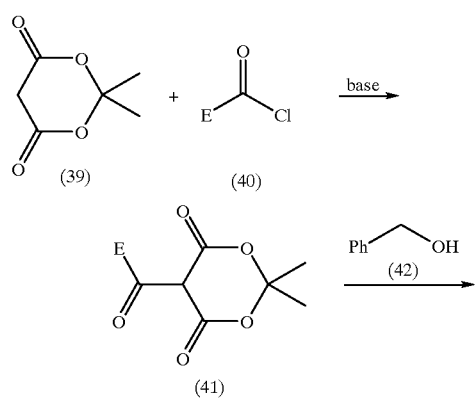

Namely, Meldrum's acid (39) is reacted with an acyl chloride (40) in the presence of a suitable base to obtain a compound (41), which is then reacted with benzyl alcohol (42) to obtain a benzyl acylacetate (43). This ester (43) is then subjected to Knoevenagel reaction with an aldehyde (24) to obtain a compound (44), which is reacted with 2-cyanoethyl 3-aminocrotonate (27) to obtain a dihydropyridine derivative (45). This compound is converted into a compound (46) by, for example, the catalytic reduction. The compound (46) is condensed with an amine (33) to obtain an amide derivative (47), which is treated with a base such as sodium hydroxide to obtain a dihydropyridine derivative (1-6) of the present invention.

The benzyl acylacetate (43) used in the above-described process can be obtained also by transesterifying a methyl acylacetate (48) with benzyl alcohol (42).

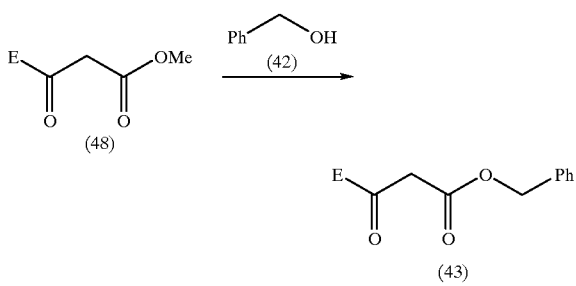

When the compounds of general formula (1) of the present invention can form salts, the salts must be pharmaceutically acceptable ones. The salts are ammonium salts, salts with alkali metals such as sodium and potassium, salts with alkaline earth metals such as calcium and magnesium, aluminum salts, zinc salts, salts with organic amines such as morpholine and piperidine, and salts with basic amino acids such as arginine and lysine.

The compounds of general formula (1) or salts thereof can be administered as they are or in the form of various medicinal compositions. The forms of the medicinal compositions are, for example, tablets, powders, pills, granules, capsules, suppositories, solutions, sugar-coated tablets and depots. They can be prepared with an ordinary preparation assistants.

For example, tablets can be prepared by mixing the dihydropyridine derivative used as the active ingredient of the present invention with a known assistant material such as an inert diluent, e. g. lactose, calcium carbonate or calcium phosphate; a binder, e. g. acacia, corn starch or gelatin; an excipient, e. g. alginic acid, corn starch or pregelatinized starch; a sweetening agent, e. g. sucrose, lactose or saccharin; a flavoring agent, e. g. peppermint, cherry; and magnesium stearate, talc or carboxymethylcellulose.

The N-type calcium channel antagonists containing one of the compounds of general formula (1) and salts thereof are usable as therapeutic agents for any of encephalopathies caused by the ischemia in the acute phase after the onset of cerebral infarction, cerebral hemorrhage (including subarachnoidal bleeding) or the like; progressive neurodegenerative diseases, e. g. Alzheimer's disease; AIDS related dementia; Parkinson's disease; dementia caused by cerebrovascular disorders and ALS; various pains, e. g. neuropathy caused by head injury; sharp pain caused by spinal injury, diabetes or thromboangitis obliterans; pain after an operation; migraine and visceral pain; various diseases caused by psychogenic stress, e. g. bronchial asthma; unstable angina and hypersensitive colon inflammation; emotional disorder; and drug addiction withdrawal symptoms, e. g. ethanol addiction withdrawal symptoms.

The dosage of the therapeutic agent used for the above-described purpose varies depending on the intended therapeutic effect, method of administration, period of therapy, age, body weight, etc. Usually, it is given to adults in an amount of 1 μg to 5 g/day in the oral administration, and 0.01 μg to 1 g/day in the parenteral administration.

The following Examples will further illustrate the preferred embodiments of the present invention, which by no means limit the invention.

EXAMPLE 1

Synthesis of 4-(3-chlorophenyl)-2,6-dimethyl-5-(3-phenyl-2-propene-1-ylcarbamoyl)-1,4-dihydropyridine-3-carboxylic acid 1) Synthesis of 3-oxo-N-(3-phenyl-2-propene-1-yl) butyramide 3.06 g (23.0 mmol) of cinnamylamine, 2.32 ml (30.1 mmol) of ketene dimer and 0.321 ml (2.30 mmol) of triethylamine were heated at 70° C. under stirring in 23 ml of toluene for 3 hours. A saturated aqueous sodium hydrogencarbonate solution was added to the reaction mixture. After the extraction with ethyl acetate, the organic layer was dried over anhydrous sodium sulfate and then concentrated under reduced pressure to obtain the title compound.

Yield: 5.08 mg (23.4 mmol) (100%)

MS (ESI, m/z) 216 (M−H)−

$^1$H-NMR (CDCl$_3$): 2.29 (3H, s), 3.47 (2H, s), 4.07 (2H, t), 6.20 (1H, dt), 6.54 (1H, d), 7.15–7.40 (5H, m)

2) Synthesis of 2-acetyl-3-(3-chlorophenyl)-N-(3-phenyl-2-propene-1-yl)acrylamide 652 mg (3.00 mmol) of 3-oxo-N-(3-phenyl-2-propene-1-yl)butyramide, 0.340 ml (3.00 mmol) of 3-chlorobenzaldehyde and 0.030 ml (0.30 mmol) of piperidine were heated under reflux in 25 ml of benzene overnight while water was removed. Benzene was evaporated under reduced pressure. The residue was purified by the silica gel chromatography (hexane/ethyl acetate=2/1) to obtain the title compound.

Yield: 379 mg (1.12 mmol) (37%)

MS (ESI, m/z) 340 (M+H)$^+$ $^1$H-NMR (CDCl$_3$): 2.46 (3H, s), 4.13–4.19 (2H, m), 5.01 (1H, s), 5.90(1H, t), 6.13 (1H, dt), 6.50 (1H, d), 7.22–7.55 (9H, m)

3) Synthesis of 2-cyanoethyl 4-(3-chlorophenyl)-2,6-dimethyl-5-(3-phenyl-2-propene-1-ylcarbamoyl)-1,4-dihydropyridine-3-carboxylate 193 mg (0.568 mmol) of 2-acetyl-3-(3-chlorophenyl)-N-(3-phenyl-2-propene-1-yl)acrylamide and 87.6 mg (0.568 mmol) of 2-cyanoethyl 3-aminocrotonate were heated at 70° C. under stirring in 2.8 ml of 2-propanol overnight. 2-Propanol was evaporated under reduced pressure. The residue was purified by the silica gel chromatography (hexane/ethyl acetate=1/2) to obtain the title compound.

Yield: 85.0 mg (0.179 mmol) (32%)

MS (ESI, m/z) 476 (M+H)$^+$ $^1$H-NMR (CDCl$_3$): 2.22 (3H, s), 2.30 (3H, s), 2.60 (2H, t), 3.90–4.00(2H, m), 4.15–4.30 (2H, m), 4.77 (1H, s), 5.55 (1H, t), 6.00 (1H, bs), 6.04 (1H, dt), 6.27 (1H, d), 7.12–7.32 (9H, m)

4) Synthesis of 4-(3-chlorophenyl)-2,6-dimethyl-5-(3-phenyl-2-propene-1-ylcarbamoyl)-1,4-dihydropyridine-3-carboxylate 85.0 mg (0.179 mmol) of 2-cyanoethyl 4-(3-chlorophenyl)-2,6-dimethyl-5-(3-phenyl-2-propene-1-ycarbamoyl)-1,4-dihydropyridine-3-carboxylate was dissolved in 3.6 ml of methanol. 0.358 ml of 1 N aqueous sodium hydroxide solution was added to the obtained solution, and they were stirred at room temperature for 2.5 hours. 2 N hydrochloric acid was added to the reaction mixture, and methanol was evaporated under reduced pressure. After the extraction with ethyl acetate, the organic layer was dried over anhydrous sodium sulfate and then concentrated under reduced pressure. The residue was purified by the silica gel chromatography (hexane/ethyl acetate=1/2) to obtain the title compound.

Yield: 38.9 mg (0.092 mmol) (51%)

MS (ESI, m/z) 421 (M−H)⁻

$^1$H-NMR (CDCl$_3$): 2.31 (6H, s), 3.92–4.02 (2H, m), 4.78 (1H, s), 5.54(1H, t), 5.70 (1H, s), 6.07 (1H, dt), 6.28 (1H, d), 7.14–7.31 (9H, m)

EXAMPLE 2

Synthesis of methyl 2,6-dimethyl-4-(3-nitrophenyl)-5-(3-phenyl-2-propene-1-ylcarbamoyl)-1,4-dihydropyridine-3-carboxylate 1) Synthesis of 2-acetyl-3-(3-nitrophenyl)-N-(3-phenyl-2-propene-1-yl)acrylamide The title compound was obtained from 652 mg (3.00 mmol) of 3-oxo-N-(3-phenyl-2-propene-1-yl)butyramide and 454 mg (3.00 mmol) of 3-nitrobenzaldehyde in the same manner as that of Example 1-2).

Yield: 345 mg (0.984 mmol) (33%)

$^1$H-NMR (CDCl$_3$): 2.50 (3H, s), 4.14–4.21 (2H, m), 6.09–6.20 (2H, m), 6.52 (1H, d), 7.27–7.33 (5H, m), 7.50 (1H, t), 7.57 (1H, s), 7.87 (1H, d), 8.21 (1H, d), 8.41 (1H, s)

2) Synthesis of methyl 2,6-dimethyl-4-(3-nitrophenyl)-5-(3-phenyl-2-propene-1-ylcarbamoyl)-1,4-dihydropyridine-3-carboxylate The title compound was obtained from 173 mg (0.492 mmol) of 2-acetyl-3-(3-nitrophenyl)-N-(3-phenyl-2-propene-1-yl)acrylamide and 56.6 mg (0.492 mmol) of methyl 3-aminocrotonate in the same manner as that of Example 1-3).

Yield: 138 mg (0.309 mmol) (63 %)

$^1$H-NMR (CDCl$_3$): 2.26 (3H, s), 2.32 (3H, s), 3.64 (3H, s), 3.98 (2H, t),4.96 (1H, s), 5.56 (1H, t), 6.00 (1H, bs), 6.06 (1H, dt), 6.33 (1H, d), 7.20–7.35 (5H, m), 7.39 (1H, t), 7.65 (1H, d), 8.00 (1H, d), 8.14 (1H, s)

EXAMPLE 3

Synthesis of 2-methoxyethyl 2,6-dimethyl-4-(3-nitrophenyl)-5-(3-phenyl-2-propene-1-ylcarbamoyl)-1,4-dihydropyridine-3-carboxylate The title compound was obtained from 173 mg (0.492 mmol) of 2-acetyl-3-(3-nitrophenyl)-N-(3-phenyl-2-propene-1-yl)acrylamide and 78.3 mg (0.492 mmol) of 2-methoxyethyl 3-aminocrotonate in the same manner as that of Example 1-3).

Yield: 157 mg (0.318 mmol) (65%)

$^1$H-NMR (CDCl$_3$): 2.25 (3H, s), 2.31 (3H, s), 3.30 (3H, s), 3.50–3.55(2H, m), 3.97 (2H, t), 4.09–4.25 (2H, m), 4.98 (1H, s), 5.63 (1H, t), 6.07 (1H, dt), 6.10 (1H, bs), 6.32 (1H, d), 7.18–7.32 (5H, m), 7.37 (1H, t), 7.68 (1H, d), 8.00 (1H, d), 8.14 (1H, s)

EXAMPLE 4

Synthesis of 2,6-dimethyl-4-(3-nitrophenyl)-5-(3-phenyl-2-propene-1-ylcarbamoyl)-1,4-dihydropyridine-3-carboxylc acid 1) Synthesis of 2-acetyl-3-(3-nitrophenyl)-N-(3-phenyl-2-propene-1-yl)acrylamide 1.03 g (4.74 mmol) of 3-oxo-N-(3-phenyl-2-propene-1-yl)butyramide, 723 mg (4.78 mmol) of 3-nitrobenzaldehyde and 0.2 ml (2.02 mmol) of piperidine were heated under reflux in the presence of a catalytic amount of p-toluenesulfonic acid in 30 ml of benzene overnight while water was removed. Ethyl acetate was added to the reaction mixture. After washing with 2 N hydrochloric acid and then with a saturated aqueous sodium hydrogencarbonate solution, the organic layer was dried over anhydrous sodium sulfate. After the concentration under reduced pressure, the residue was purified by the silica gel chromatography (hexane/ethyl acetate=2/1) to obtain the title compound.

Yield: 398 mg (1.14 mmol) (24.0%)

$^1$H-NMR (CDCl$_3$): 2.50 (3H, s), 4.14–4.21 (2H, m), 6.08–6.20 (2H, m), 6.52 (1H, d), 7.22–7.34 (5H, m), 7.50 (1H,t), 7.57 (1H, s), 7.89 (1H, d), 8.20 (1H, d), 8.40 (1H,s)

2) Synthesis of 2-cyanoethyl 2,6-dimethyl-4-(3-nitrophenyl)-5-(3-phenyl-2-propene-1-ylcarbamoyl)-1,4-dihydropyridine-3-carboxylate The title compound was obtained from 388 mg (1.11 mmol) of 2-acetyl-3-(3-nitrophenyl)-N-(3-phenyl-2-propene-1-yl)acrylamide and 174 mg (1.13 mmol) of 2-cyanoethyl 3-aminocrotonate in the same manner as that of Example 1-3).

Yield: 290 mg (0.60 mmol) (54.2%)

MS (ESI, m/z) 487 (M+H)⁺

$^1$H-NMR (CDCl$_3$): 2.27 (3H, s), 2.37 (3H, s), 2.65 (2H, t), 3.96–4.04 (2H, m), 4.20–4.34 (2H, m), 4.96 (1H, s), 5.52 (1H, t), 5.78 (1H, bs), 6.07 (1H, dt), 6.35 (1H, d), 7.20–7.34 (5H, m), 7.41 (1H,t), 7.68 (1H, d), 8.04 (1H, d), 8.13 (1H,s)

3) Synthesis of 2,6-dimethyl-4-(3-nitrophenyl)-5-(3-phenyl-2-propene-1-ylcarbamoyl)-1,4-dihydropyridine-3-carboxylate 254 mg (0.52 mmol) of 2-cyanoethyl 2,6-dimethyl-4-(3-nitrophenyl)-5-(3-phenyl-2-propene-1-ylcarbamoyl)-1,4-dihydropyridine-3-carboxylate was dissolved in 20 ml of methanol. 1 ml of 1 N aqueous sodium hydroxide solution was added to the obtained solution, and they were stirred at room temperature for 7 hours. 2 N hydrochloric acid was added to the reaction mixture, and methanol was evaporated under reduced pressure. Water was added to the residue, and precipitates thus formed were taken by the filtration. After washing with water and then with hexane/ethyl acetate 3:1), the product was dried under reduced pressure to obtain the title compound.

Yield: 165 mg (0.38 mmol) (73.2%)

MS (ESI, m/z) 432 (M−H)⁻

$^1$H-NMR (DMSO-d$_6$): 2.08 (3H, s), 2.25 (3H, s), 3.76–3.88 (2H, m), 4.99 (1H, s), 6.12 (1H, dt), 6.23 (1H, d), 7.18–7.34 (5H, m), 7.52 (1H,t), 7.60–7.66 (1H, m), 7.87 (1H, t), 7.97–8.06 (2H, m), 8.43 (1H,s)

EXAMPLE 5

Synthesis of 4-(3-chlorophenyl)-2,6-dimethyl-5-nitro-1,4-dihydropyridine-3-carboxylic acid (3-phenyl-2-propene-1-yl)amide 1) Synthesis of 2-cyanoethyl 4-(3-chlorophenyl)-2,6-dimethyl-5-nitro-1,4-dihydropyridine-3-carboxylate The title compound was obtained from 526 mg (5.10 mmol) of nitroacetone, 0.58 ml (5.12 mmol) of 3-chlorobenzaldehyde and 788 mg (5.11 mmol) of 2-cyanoethyl 3-aminocrotonate in the same manner as that of Example 1-3).

Yield: 1.251 g (3.46 mmol) (67.8%)
MS (ESI, m/z) 360 (M−H)⁻
¹H-NMR (CDCl₃): 2.42 (3H, s), 2.55 (3H, s), 2.63 (2H, t), 4.24–4.34 (2H, m), 5.37 (1H, s), 5.95 (1H, s), 7.17–7.27 (4H, m)

2) Synthesis of 4-(3-chlorophenyl)-2,6-dimethyl-5-nitro-1,4-dihydropyridine-3-carboxylic acid The title compound was obtained from 198 mg (0.55 mmol) of 2-cyanoethyl 4-(3-chlorophenyl)-2,6-dimethyl-5-nitro-1,4-dihydropyridine-3-carboxylate in the same manner as that of Example 4-3).

Yield: 98 mg (0.32 mmol) (58.0%)
MS (ESI, m/z) 307 (M−H)⁻
¹H-NMR (DMSO-d₆): 2.29 (6H, s), 5.23 (1H, s), 7.13–7.34 (4H, m), 9.58 (1H, s)

3) Synthesis of 4-(3-chlorophenyl)-2,6-dimethyl-5-nitro-1,4-dihydropyridine-3-carboxylic acid (3-phenyl-2-propene-1-yl)amide 93 mg (0.30 mmol) of 4-(3-chlorophenyl)-2,6-dimethyl-5-nitro-1,4-dihydropyridine-3-carboxylic acid, 100 mg (0.75 mmol) of cinnamylamine, 138 mg (0.54 mmol) of 2-chloro-1-methylpyridinium iodide and 0.15 ml (1.08 mmol) of triethylamine were stirred in 5 ml of DMF at room temperature for 2 days. DMF was evaporated under reduced pressure. Ethyl acetate was added to the reaction mixture. After washing with 1 N hydrochloric acid, the organic layer was dried over anhydrous sodium sulfate. After the concentration under reduced pressure, the residue was purified by the silica gel chromatography (hexane/ethyl cetate=4/1) to obtain the title compound.

Yield: 67 mg (0.16 mmol) (52.2%)
MS (ESI, m/z) 422 (M−H)⁻
¹H-NMR (CDCl₃): 2.27 (3H, s), 2.53 (3H, s), 3.90–4.06 (2H, m), 5.24 (1H, s), 5.49 (1H, m), 6.03 (1H, dt), 6.13 (1H, s), 6.29 (1H, d), 7;18–7.32 (9H, m)

EXAMPLE 6

Synthesis of 4-(3-chlorophenyl)-2,6-dimethyl-1,4-dihydropyridine-3,5-dicarboxylic acid 3-((2-methoxyethyl)amide) 5-((3-phenyl-2-propene-1-yl)amide)

245 mg (0.58 mmol) of 4-(3-chlorophenyl)-2,6-dimethyl-5-(3-phenyl-2-propene-1-ylcarbamoyl)-1,4-dihydropyridine-3-carboxylic acid, 0.06 ml (0.69 mmol) of 2-methoxyethylamine, 137 mg (0.71 mmol) of 1-(3-dimethylaminopropyl)-3-ethylcarbodiimide hydrochloride and 10 mg (0.08 mmol) of 4-dimethylaminopyridine were stirred in 12 ml of dichloromethane at room temperature for two days. Water was added to the reaction mixture. After washing with dichloromethane, the organic layer was dried over anhydrous sodium sulfate. After the concentration under reduced pressure, the residue was purified by HPLC (water/acetonitrile) to obtain the title compound.

Yield: 143 mg (0.30 mmol) (51.4%)
MS (ESI, m/z) 478 (M−H)⁻
¹H-NMR (CDCl₃): 2.18 (3H, s), 2.22 (3H, s), 3.24 (3H, s), 3.26–3.42 (4H, m), 3.94–4.02 (2H, m), 4.71 (1H, s), 5.21 (1H, s), 5.41 (1H, m), 5.68 (1H, m), 6.04 (1H, dt), 6.29 (1H, d), 7.16–7.30 (9H, m)

EXAMPLE 7

Synthesis of 4-(3-chlorophenyl)-2, 6dimethoxymethyl-6-methyl-3- (3-phenyl-2-propene-1-ylcarbamoyl)-1,4- dihydropyridine-5-carboxylic acid 1) Synthesis of benzyl 4,4-dimethoxy-3-oxobutyrate 2.68 g (14.1 mmol) of ethyl 4,4-dimethoxy-3-oxobutyrate, 3.62 ml (34.9 mmol) of benzyl alcohol and 244 mg (2.0 mmol) of 4-dimethylaminopyridine were heated under reflux in 40 ml of toluene for three nights. A phosphate buffer solution was added to the obtained reaction solution. After the extraction with ethyl acetate, the organic layer was washed with a saturated aqueous salt solution and then dried over anhydrous sodium sulfate. The solvent was evaporated under reduced pressure, and the residue was purified by the silica gel chromatography (hexane/ethyl acetate=9:1) to obtain the title compound.

Yield: 2.90 g (11.5 mmol) (81%)
¹H-NMR (CDCl₃): 3.36 (6H, s), 3.61 (2H, s), 4.54 (1H, s), 5.16 (2H, s) 7.28–7.36 (5H, m)

2) Synthesis of 5-(2-cyanoethyl) 3-benzyl 4-(3-chlorophenyl)-2-dimethoxymethyl-6-methyl-1,4-dihydropyridine-3,5-dicarboxylate 3.84 g (7.52 mmol) of benzyl 4,4-dimethoxy-3-oxobutyrate, 1.30 ml (11.5 mmol) of 3-chlorobenzaldehyde and 0.114 ml of piperidine were heated under reflux in 11.5 ml of benzene overnight while water was removed. The reaction solution was washed with water and then dried over anhydrous magnesium sulfate. The solvent was evaporated under reduced pressure. The residue thus obtained and 1.77 g (11.5 mmol) of 2-cyanoethyl 3-aminocrotonate were heated at 70° C. under stirring in 57.5 ml of 2-propanol overnight. The reaction mixture was then heated at 120° C. under stirring under atmospheric pressure for 4 hours while 2-propanol was evaporated. The residue was purified by the silica gel chromatography (hexane/ethyl acetate=2/1) to obtain the title compound.

Yield: 3.84 g (7.52 mmol) (65%)
MS (ESI, m/z) 533 (M+Na)⁺
¹H-NMR (CDCl₃): 2.37 (3H, s), 2.60 (2H, t), 3.41 (3H, s), 3.42 (3H, s) 4.17–4.31 (2H, m), 5.01 (1H, s), 5.06 (1H, d), 5.15 (1H, d), 6.02 (1H, s), 6.81 (1H, bs), 7.10–7.35 (9H, m)

3) Synthesis of 5-(2-cyanoethyl) 4-(3-chlorophenyl)-2-dimethoxymethyl-6-methyl-1,4-dihydropyridine-3,5-dicarboxylate 3.84 g (7.52 mmol) of 5-(2-cyanoethyl) 3-benzyl 4-(3-chlorophenyl)-2-dimethoxymethyl-6-methyl-1,4-dihydropyridine-3,5-dicarboxylate was dissolved in 37.6 ml of ethyl acetate. 107 mg of 10% palladium/carbon was added to the obtained solution, and they were stirred at room temperature for three nights. The insoluble matter was filtered off, and the solvent was evaporated under reduced pressure. The residue was purified by the silica gel chromatography (ethyl acetate) to obtain the title compound.

Yield: 2.37 g (5.63 mmol) (75%)
MS (ESI, m/z) 419 (M−H)⁻
¹H-NMR (DMSO-d₆): 2.34 (3H, s), 2.81–2.88 (2H, m), 4.16 (2H, t), 44 (1H, bs), 6.09 (1H, bs), 7.15–7.28 (4H, m), 8.54 (1H, bs)

4) Synthesis of 5-(2-cyanoethyl) 4-(3-chlorophenyl)-2-dimethoxymethyl-6-methyl-3-(3-phenyl-2-propene-1-ylcarbamoyl)-1,4-dihydropyridine-5-carboxylate The title compound was obtained from 1.59 g (3.77 mmol) of 5-(2-cyanoethyl) 4-(3-chlorophenyl)-2-dimethoxymethyl-6-methyl-1,4-dihydropyridine-3,5-dicarboxylate and 628 mg (4.71 mmol) of cinnamylamine in the same manner as that of Example 5-3).

Yield: 1.32 g (2.47 mmol) 65%

MS (ESI, m/z) 558 (M+Na)$^+$ $^1$H-NMR (CDCl$_3$): 2.39 (3H, s), 2.61 (2H, t), 3.36 (3H, s), 3.46 (3H, s) 3.97–4.04 (2H, m), 4.20–4.32 (2H, m), 5.01 (1H, s), 5.56 (1H, s), 6.08 (1H, dt), 6.33 (1H, bs), 6.34 (1H, d), 6.55 (1H, s), 7.11–7.31 (9H, m)

5) Synthesis of 4-(3-chlorophenyl)-2-dimethoxymethyl-6-methyl-3-(3-phenyl-2-propene-1-ylcarbamoyl)-1,4-dihydropyridine-5-carboxylic acid 134 mg (1.16 mmol) of 5-(2-cyanoethyl) 4-(3-chlorophenyl)-2-dimethoxymethyl-6-methyl-3-(3-phenyl-2-propene-1-ylcarbamoyl)-1,4-dihydropyridine-5-carboxylate was dissolved in 2.5 ml of methanol. 0.25 ml of 1 N aqueous sodium hydroxide solution was added to the obtained solution, and they were stirred at room temperature for 3 hours. An aqueous potassium hydrogensulfate solution was added to the reaction mixture. After the solvent was evaporated under reduced pressure, the residue was washed with water and then dried under reduced pressure to obtain the title compound.

Yield: 68 mg (0.141 mmol) 56%

MS (ESI, m/z) 481 (M–H)$^-$ $^1$H-NMR (DMSO-d$_6$): 2.28 (3H, s), 3.28 (3H, s), 3.32 (3H, s), 3.76–3.94 (2H, m), 4.90 (1H, s), 5.57 (1H, s), 6.17 (1H, dt), 6.32 (1H, d), 7.09–7.33 (9H, m), 8.02 (1H, bs)

EXAMPLE 8

Synthesis of 4-(3-chlorophenyl)-2,6-dimethyl-5-(methyl-(3-phenyl-2-propene-1-yl)carbamoyl)-1,4-dihydropyridine-3-carboxylic acid 1) Synthesis of N-methyl-3-oxo-N-(3-phenyl-2-propene-1-yl)butyramide 0.736 g (5.0 mmol) of methyl-(3-phenyl-2-propene-1-yl)amine, 0.386 ml (5.0 mmol) of ketene dimer and 0.07 ml (0.50 mmol) of triethylamine were heated at 70° C. under stirring in 5 ml of toluene overnight. A saturated aqueous sodium hydrogencarbonate solution was added to the reaction mixture. After the extraction with ethyl acetate, the organic layer was dried over anhydrous sodium sulfate. The solvent was evaporated under reduced pressure, and the residue was purified by the thin-layer silica gel chromatography (ethyl acetate) to obtain the title compound.

Yield: 306 mg (1.32 mmol) (26%)

MS (ESI, m/z) 232 (M+H)$^+$ $^1$H-NMR (CDCl$_3$): 2.27 (3H, s), 2.98 (3H, s), 3.57 (2H, s), 4.03 (1H, d) 4.16 (1H, d), 6.21 (1H, dt), 6.50 (1H, d), 7.20–7.40 (5H, m)

2) Synthesis of 2-cyanoethyl 4-(3-chlorophenyl)-2,6-dimethyl-5-(methyl-(3-phenyl-2-propene-1-yl)carbamoyl)-1,4-dihydropyridine-3-carboxylate 306 mg (1.32 mmol) of N-methyl-3-oxo-N-(3-phenyl-2-propene-1-yl)butyramide, 0.150 ml (1.32 mmol) of 3-chlorobenzaldehyde and 0.013 ml (0.132 mmol) of piperidine were heated under reflux overnight while water was removed. After washing with water, the organic layer was dried over anhydrous magnesium sulfate and then the solvent was evaporated under reduced pressure. The residue and 204 mg (1.32 mmol) of 2-cyanoethyl 3-aminocrotonate were heated at 85° C. under stirring in 6.6 ml of 2-propanol overnight. The reaction mixture was further heated at 120° C. under stirring under atmospheric pressure for 3 hours while 2-propanol was evaporated. The residue was purified by the high-performance liquid chromatography to obtain the title compound.

Yield: 224 mg (0.456 mmol) (35%)

MS (ESI, m/z) 490 (M+H)$^+$ $^1$H-NMR (CDCl$_3$): 1.75(3H, s), 2.30–2.90 (8H, m), 3.88–4.30 (4H, m), 4.85 (1H, s), 5.97–6.47 (3H, m), 7.03–7.40 (9H, m)

3) Synthesis of 4-(3-chlorophenyl)-2,6-dimethyl-5-(methyl-(3-phenyl-2-propene-1-yl)carbamoyl)-1,4-dihydropyridine-3-carboxylic acid 224 mg (0.456 mmol) of 2-cyanoethyl 4-(3-chlorophenyl)-2,6-dimethyl-5-(methyl-(3-phenyl-2-propene-1-yl)carbamoyl)-1,4-dihydropyridine-3-carboxylate was dissolved in 4.6 ml of methanol. 0.456 ml of 1 N aqueous sodium hydroxide solution was added to the obtained solution, and they were stirred at room temperature overnight. An aqueous potassium hydrogensulfate solution was added to the reaction mixture. Methanol was evaporated under reduced pressure. After the extraction with ethyl acetate, the organic layer was dried over anhydrous sodium sulfate and then concentrated under reduced pressure. The residue was purified by the silica gel chromatography (hexane/ethyl acetate=5/1) to obtain the title compound.

Yield: 109.4 mg (0.250 mmol) (55%)

MS (ESI, m/z) 435 (M–H)$^-$ $^1$H-NMR (d$_6$-DMSO): 1.72 (3H, s), 2.27 (3H, s), 2.50 (3H, s), 3.82–3.97 (2H, m), 4.64 (1H, s), 5.98–6.46 (2H, m), 7.00–7.40 (9H, m), 8.29 (1H, bs)

EXAMPLE 9

Synthesis of 4-(3-chlorophenyl)-2-methyl-5-oxo-1,4,5,7-tetrahydro [3,4-b]pyridine-3-carboxylic acid (3-phenyl-2-propene-1-yl)amide 1) Synthesis of ethyl 2-acetoxymethyl-4-(3-chlorophenyl)-6-methyl-5-(3-phenyl-2-propene-1-ylcarbamoyl)-1,4-dihydropyridine-3-carboxylate 652 mg (3.00 mmol) of 3-oxo-N-(3-phenyl-2-propene-1-yl)butyramide, 0.510 ml (3.00 mmol) of 3-chlorobenzaldehyde and 0.045 ml (0.30 mmol) of piperidine were heated under reflux in 37.5 ml of benzene overnight while water was removed. The reaction solution was washed with water and then dried over anhydrous magnesium sulfate. The solvent was evaporated under reduced pressure. The residue thus obtained, 564 mg (3.0 mmol) of ethyl 4-acetoxy-3-oxobutyrate and 278 mg (3.6 mmol) of ammonium acetate were heated at 80° C. under stirring in 15 ml of 2-propanol for four nights. The reaction mixture was then heated at 120° C. under stirring under atmospheric pressure for 4 hours while 2-propanol was evaporated. The residue was purified by the silica gel chromatography (hexane/ethyl acetate=1/2) to obtain the title compound.

Yield: 272 mg (0.535 mmol) (18%)

MS (ESI, m/z) 509 (M+H)$^+$ $^1$H-NMR (CDCl$_3$): 1.23 (3H, t), 2.24 (3H, s), 2.26 (3H, s), 3.90–4.15 (4H, m), 4.83 (1H, s), 5.28 (1H, d), 5.32 (1H, d), 5.59 (1H, bt), 6.04 (1H, dt), 6.25 (1H, d), 6.60 (1H, bs), 7.10–7.40 (9H, m)

2) Synthesis of 4-(3-chlorophenyl)-2-methyl-5-oxo-1,4,5,7-tetrahydro [3,4-b]pyridine-3-carboxylic acid (3-phenyl-2propene-1-yl)amide 272 mg (0.535 mmol) of ethyl 2-acetoxymethyl-4-(3-chlorophenyl-6-methyl-5-(3-phenyl-2-propene-1- ylcarbamoyl)-1,4-dihydropyridine-3-carboxylate was dissolved in 5.4 ml of methanol. 0.535 ml of 2 N aqueous sodium hydroxide solution was added to the obtained solution, and they were stirred at room temperature overnight. An aqueous potassium hydrogensulfate solution was added to the reaction mixture, and methanol was evaporated under reduced pressure. After the extraction with ethyl acetate, the organic layer was dried over anhydrous sodium sulfate and then concentrated under reduced pressure. The residue was washed with methanol and dried under reduced pressure to obtain the title compound.

Yield: 35.8 mg (0.851 mmol) (16%).

MS (ESI, m/z) 419 (M–H)⁻

$^1$H-NMR (d$_6$-DMSO): 2.05 (3H, s), 3.79 (2H, bt), 4.76 (1H, d), 4.86 (1H, d), 4.89 (1H, s), 6.01 (1H, dt), 6.13 (1H, d), 7.15–7.35 (9H, m), 8.02 (1H, bt), 9.32 (1H, bs)

EXAMPLE 10

Synthesis of 4-(3-cyanophenyl)-2,6-dimethyl-5-(3-phenyl-2-propene-1-ylcarbamoyl)-1,4-dihydropyridine-3-carboxylic acid 1) Synthesis of 2-cyanoethyl 4-(3-cyanophenyl)-2,6-dimethyl-5-(3-phenyl-2-propene-1-ylcarbamoyl)-1,4-dihydropyridine-3-carboxylate 541 mg (2.49 mmol) of 3-oxo-N-(3-phenyl-2-propene-1-yl)butyramide, 328 mg (2.50 mmol) of 3-cyanobenzaldehyde and 0.2 ml (2.02 mmol) of piperidine were heated under reflux in the presence of a catalytic amount of p-toluene Sulfonic acid in 30 ml of benzene overnight while water was removed. Ethyl acetate was added to the reaction mixture, which was washed with 2 N hydrochloric acid and then with a saturated aqueous sodium hydrogencarbonate solution. The organic layer was dried over anhydrous sodium sulfate and then concentrated under reduced pressure to obtain 2-acetyl-3-(3-cyanophenyl)-N-(3-phenyl-2-propene-1-yl) acrylamide. This product was heated together with 387 mg (2.5 1 mmol) of 2-cyanoethyl 3-aminocrotonate at 80° C. under stirring in 20 ml of 2-propanol for four days. 2-Propanol was evaporated under reduced pressure. The residue was purified by the silica gel chromatography (chloroform/methanol=100/1) to obtain the title compound.

Yield: 290 mg (0.62 mmol) (24.9%)

MS (ESI, m/z) 467 (M+H)⁺

$^1$H-NMR (CDCl$_3$): 2.26 (3H, s), 2.36 (3H, s), 2.60–2.67 (2H, m), 3.94–4.04 (2H, m), 4.22–4.30 (2H, m), 4.87 (1H, s), 5.49 (1H, t), 5.76 (1H, s), 6.07 (1H, dt), 6.34 (1H, d), 7.20–7.61 (9H, m)

2) Synthesis of 4-(3-cyanophenyl)-2,6-dimethyl-5-(3-phenyl-2-propene-1-ylcarbamoyl)-1,4-dihydropyridine-3-carboxylic acid The title compound was obtained from 284 mg (0.61 mmol) of 2-cyanoethyl 4-(3-cyanophenyl)-2,6-dimethyl-5-(3-phenyl-2-propene-1-ylcarbamoyl)-1,4-dihydropyridine-3-carboxylate in the same manner as that of Example 4-3).

Yield: 71 mg (0.17 mmol) (28.2%).

MS (ESI, m/z) 412 (M–H)⁻

$^1$H-NMR (DMSO-d$_6$): 2.08 (3H, s), 2.24 (3H, s), 3.83 (2H, t), 4.91 (1H, s), 6.12 (1H, dt), 6.22 (1H, d), 7.18–7.62 (9H, m), 7.84 (1H,t), 8.37 (1H,s)

EXAMPLE 11

Synthesis of 4-(3-chlorophenyl)-2,6-dimethyl-5-(3-phenylpropylcarbamoyl)-1,4-dihydropyridine-3-carboxylic acid 1) Synthesis of mono(2-cyanoethyl) 4-(3-chlorophenyl)-2,6-dimethyl-1,4-dihydropyridine-3,5-dicarboxylate 3.53 g (22.9 mmol) of 2-cyanoethyl 3-aminocrotonate, 4.40 g (22.9 mmol) of benzyl acetoacetate and 2.60 ml (23.0 mmol) of 3-chlorobenzaldehyde were heated at 80° C. under stirring in 100 ml of 2-propanol for 3 days. 2-Propanol was evaporated under reduced pressure to obtain 5-benzyl 3-(cyanoethyl) 4-(3-chlorophenyl)-2,6-dimethyl-1,4-dihydropyridine-3,5-dicarboxylate. 100 ml of ethyl acetate and 10% palladium/carbon were added to the reaction mixture and they were stirred at room temperature in hydrogen atmosphere under atmospheric pressure for 7 days. The reaction liquid was filtered, and the filtrate was evaporated under reduced pressure. The residue was washed with chloroform to obtain the title compound.

Yield: 4.82 g (13.4mmol) (58.4%)

MS (ESI, m/z) 359 (M–H)⁻

$^1$H-NMR (DMSO-d$_6$): 2.27 (3H, s), 2.29 (3H, s), 2.79–2.86 (2H, m), 4.15 (2H, t), 4.87 (1H, s), 7.10–7.28 (5H, m), 8.90 (1H, s)

2) Synthesis of 2-cyanoethyl 4-(3-chlorophenyl)-2,6-dimethyl-5-(3-phenylpropylcarbamoyl)-1,4-dihydropyridine-3-carboxylate The title compound was obtained from 357 mg (0.99 mmol) of mono(2-cyanoethyl) 4-(3-chlorophenyl)-2,6-dimethyl-1,4-dihydropyridine-3,5-dicarboxylate and 0.19 ml (1.34 mmol) of 3-phenylpropylamine in the same manner as that of Example 6.

Yield: 340 mg (0.71 mmol) (71.9%).

MS (ESI, m/z) 478 (M+H)⁺

$^1$H-NMR (CDCl$_3$): 1.65–1.76 (2H, m), 2.23 (3H, s), 2.33 (3H, s), 2.47 (2H,t), 2.64 (2H, t), 3.13–3.30 (2H, m), 4.23–4.32 (2H, m), 4.74 (1H, s), 5.33 (1H, t), 5.63 (1H, s), 7.07 (2H, d), 7.16–7.29 (7H, m)

3) Synthesis of 4-(3-chlorophenyl)-2,6-dimethyl-5-(3-phenylpropylcarbamoyl)-1,4-dihydropyridine-3-carboxylic acid The title compound was obtained from 330 mg (0.69 mmol) of 2-cyanoethyl 4-(3-chlorophenyl)-2,6-dimethyl-5-(3-phenylpropylcarbamoyl)-1,4-dihydropyridine-3-carboxylate in the same manner as that of Example 4-3).

Yield: 88 mg (0.21 mmol) (30.0%)

MS (ESI, m/z) 423 (M–H)⁻

$^1$H-NMR (DMSO-d$_6$): 1.57–1.68 (2H, m), 2.01 (3H, s), 2.24 (3H, s), 2.44 (2H,t), 2.98–3.12 (2H, m), 4.82 (1H, s), 7.07–7.30 (9H, m), 7.56 (1H,t), 8.26 (1H,s)

EXAMPLE 12

Synthesis of (3-phenyl-2-propene-1-yl) 4-(3-chlorophenyl)-5-cyano-2,6-dimethyl-1,4-dihydropyridine-3-carboxylate 540 mg (2.49 mmol) of 3-oxo-N-(3-phenyl-2-propene-1-yl)butyramide, 0.28 ml (2.47 mmol) of 3-chlorobenzaldehyde and 0.05 ml (0.51 mmol) of piperidine were heated under reflux in the presence of a catalytic amount of p-toluenesulfonic acid in 30 ml of benzene overnight while water was removed. Ethyl acetate was added to the reaction mixture. After washing with 2 N hydrochloric acid and then with a saturated aqueous sodium hydrogencarbonate solution, the organic layer was dried over anhydrous sodium sulfate and concentrated under reduced pressure to obtain 2-acetyl-3-(3-chlorophenyl)-N-(3-phenyl-2-propene-1-yl)acrylamide. The title compound was obtained from this compound and 212 mg (2.58 mmol) of 3-aminocrotonitrile in the same manner as that of Example 1-3).

Yield: 93 mg (0.23 mmol) (9.3%).

MS (ESI, m/z) 404 (M+H)$^+$ $^1$H-NMR (CDCl$_3$): 2.08 (3H, s), 2.26 (3H, s), 3.88–3.97 (2H, m), 4.47 (1H, s), 5.30 (1H, t), 5.71 (1H, s), 5.97 (1H, dt), 6.22 (1H, d), 7.17–7.33 (9H, m)

EXAMPLE 13

Synthesis of 4-(3-trifluoromethylphenyl)-2,6-dimethyl-5-[(3-phenyl-2-propene-1-yl)carbamoyl]-1,4-dihydropyridine-3-carboxylic acid 1) Synthesis of 2-acetyl-3-(3-trifluoromethylphenyl)-N-(3-phenyl-2-propene-1-yl)acrylamide The title compound was obtained from 652 mg (3.00 mmol) of 3-oxo-N-(3-phenyl-2-propene-1-yl)butyramide and 522 mg (3.00 mmol) of 3-trifluoromethylbenzaldehyde in the same manner as that of Example 4-1).

Yield: 453 mg (1.21 mmol) (40.4%)

MS (ESI, m/z) 374 (M+H)$^+$ $^1$H-NMR (CDCl$_3$): 2.44 (3H, s), 4.10 (2H, t), 6.08 (1H, dt), 6.18 (1H, br t), 6.46 (1H, d), 7.20–7.30 (5H, m), 7.42 (1H, t), 7.51 (1H, s), 7.51 (1H, s), 7.60 (1H, d), 7.72–7.76 (2H, m)

2) Synthesis of 2-cyanoethyl 4-(3-trifluoromethylphenyl)-2,6-dimethyl-5-[(3-phenyl-2-propene-1-yl)carbamoyl]-1,4-dihydropyridine-3-carboxylate The title compound was obtained from 453 mg (1.21 mmol) of 2-acetyl-3-(3-chlorophenyl)-N-(3-phenyl-2-propene-1-yl)acrylamide and 187 mg (1.21 mmol) of 2-cyanoethyl 3-aminocrotonate in the same manner as that of Example 1-3).

Yield: 197 mg (0.387 mmol) (32.0%)

MS (ESI, m/z) 508 (M–H)$^-$ $^1$H-NMR (CDCl$_3$): 2.21 (3H, s), 2.31 (3H, s), 2.62 (2H, t), 3.86 (1H, br t), 3.95 (2H, t), 4.22 (2H, t), 4.89 (1H, s), 5.59 (1H, br s), 6.01 (1H, dt), 6.24–6.31 (1H, m), 7.17–7.57 (9H, m)

3) Synthesis of 4-(3-trifluoromethylphenyl)-2,6-dimethyl-5-[(3-phenyl-2-propene-1-yl)carbamoyl]-1,4-dihydropyridine-3-carboxylic acid The title compound was obtained from 197 mg (0.387 mmol) of 2-cyanoethyl 4-(3-trifluoromethylphenyl)-2,6-dimethyl-5-[(3-phenyl-2-propene-1-yl)carbamoyl)]-1,4-dihydropyridine-3-carboxylate in the same manner as that of Example 4-3).

Yield: 160 mg (0.351 mmol) (90.6%)

MS (ESI, m/z) 457 (M+H)$^+$ $^1$H-NMR (DMSO-d$_6$): 2.08 (3H, s), 2.24 (3H, s), 3.82 (2H, dd), 4.96 (1H, s), 6.09–6.26 (2H, m), 7.20–7.32 (5H, m), 7.48 (4H, d), 7.84 (1H, t), 8.35 (1H, s)

EXAMPLE 14

Synthesis of 4-(3-bromophenyl)-2,6-dimethyl-5-[(3-phenyl-2-propene-1-yl)carbamoyl]-1,4-dihydropyridine-3-carboxylic acid 1) Synthesis of 2-acetyl-3-(3-bromophenyl)-N-(3-phenyl-2-propene-1-yl)acrylamide The title compound was obtained from 652 mg (3.00 mmol) of 3-oxo-N-(3-phenyl-2-propene-1-yl)butyramide and 555 mg (3.00 mmol) of 3-bromobenzaldehyde in the same manner as that of Example 4-1).

Yield: 552 mg (1.44 mmol) (48.0%)

MS (ESI, m/z) 384 (M+H)$^+$ $^1$H-NMR (CDCl$_3$): 2.43 (3H, s), 4.12 (2H, dt), 6.07–6.18 (2H, m), 6.48 (1H, d), 7.15–7.31 (6H, m), 7.43–7.49 (3H, m), 7.66 (1H, s)

2) Synthesis of 2-cyanoethyl 4-(3-bromophenyl)-2,6-dimethyl-5-[(3-phenyl-2-propene-1-yl)carbamoyl]-1,4-dihydropyridine-3-carboxylate The title compound was obtained from 500 mg (1.30 mmol) of 2-acetyl-3-(3-bromophenyl)-N-(3-phenyl-2-propene-1-yl)acrylamide and 201 mg (1.30 mmol) of 2-cyanoethyl 3-aminocrotonate in the same manner as that of Example 1-3).

Yield: 540 mg (1.04 mmol) (80.0%)

MS (ESI, m/z) 520 (M+H)$^+$ $^1$H-NMR (CDCl$_3$): 2.22 (3H, s), 2.31 (3H, s), 2.61 (2H, t), 3.96 (2H, br s), 4.18–4.30 (2H, m), 4.78 (1H, s), 5.58 (1H, br t), 6.00–6.10 (1H, m), 6.15 (1H, br s), 6.28 (1H, d), 7.12 (1H, t), 7.20–7.45 (8H, m)

3) Synthesis of 4-(3-bromophenyl)-2,6-dimethyl-5-[(3-phenyl-2-propene-1-yl)carbamoyl]-1,4-dihydropyridine-3-carboxylic acid The title compound was obtained from 540 mg (1.04 mmol) of 2-cyanoethyl 4-(3-bromophenyl)-2,6-dimethyl-5-[(3-phenyl-2-propene-1-yl)carbamoyl)]-1,4-dihydropyridine-3-carboxylate in the same manner as that of Example 4-3).

Yield: 243 mg (0.520 mmol) (50.0%)

MS (ESI, m/z) 467 (M+H)$^+$ $^1$H-NMR (DMSO-d6): 2.06 (3H, s), 2.24 (3H, s), 3.84 (2H, br s), 4.86 (1H, s), 6.10–6.28 (2H, m), 7.15–7.32 (9H, m), 7.81 (1H, br t), 8.30 (1H, s)

EXAMPLE 15

Synthesis of 4-(4-cyanophenyl)-2,6-dimethyl-5-[(3-phenyl-2-propene -1-yl)carbamoyl]-1,4-dihydropyridine-3-carboxylic acid 1) Synthesis of 2-acetyl-3-(4-cyanophenyl)-N-(3-phenyl-2-propene-1-yl)acrylamide 600 mg (2.76 mmol) of 3-oxo-N-(3-phenyl-2-propene-1-yl)butyramide, 362 mg (2.76 mmol) of 4-cyanobenzaldehyde and 23.5 mg (0.276 mmol) of piperidine were heated under reflux in the presence of a catalytic amount of p-toluenesulfonic acid in 30 ml of benzene for 6 hours while water was removed. Benzene was evaporated under reduced pressure. Ethyl acetate was added to the reaction mixture. After washing with 1 N hydrochloric acid and then with a saturated aqueous sodium hydrogencarbonate solution, the organic layer was dried over anhydrous sodium sulfate and then concentrated under reduced pressure. The residue was purified by the silica gel chromatography (hexane/ethyl acetate=5/1) to obtain the title compound.

Yield: 590 mg (1.79 mmol) (64.7%)

MS (ESI, m/z) 329 (M–H)$^-$

2) Synthesis of 2-cyanoethyl 4-(4-cyanophenyl)-2,6-dimethyl-5-[(3-phenyl-2-propene-1-yl)carbamoyl]-1,4-dihydropyridine-3-carboxylate The title compound was obtained from 590 mg (1.76 mmol) of 2-acetyl-3-(4-cyanophenyl)-N-(3-phenyl-2- propene-1-yl)acrylamide and 271 mg (1.76 mmol) of 2-cyanoethyl 3-aminocrotonate in the same manner as that of Example 1-3).

Yield: 720 mg (1.54 mmol) (87.7%)

MS (ESI, m/z) 467 (M+H)$^+$ $^1$H-NMR (CDCl$_3$): 2.20 (3H, s), 2.32 (3H, s), 2.61 (2H, t), 3.97 (2H, br d), 4.23 (2H, t), 4.91 (1H, s), 5.68 (1H, br s), 6.04 (1H, dt), 6.30 (1H, d), 6.52 (1H, br s), 7.20–7.35 (5H, m), 7.41 (2H, d), 7.52 (2H, d)

3) Synthesis of 4-(4-cyanophenyl)-2,6-dimethyl-5-[(3-phenyl-2-propene-1-yl)carbamoyl]-1,4-dihydropyridine-3-carboxylic acid The title compound was obtained from 720 mg (1.54 mmol) of 2-cyanoethyl 4-(cyanophenyl)-2,6-dimethyl-5-[(3-phenyl-2-propene-1-yl)carbamoyl]-1,4-dihydropyridine-3-carboxylate in the same manner as that of Example 4-3).

Yield: 488 mg (1.18 mmol) (76.6%)

MS (ESI, m/z) 414 (M+H)$^+$ $^1$H-NMR (DMSO-d$_6$): 2.06 (3H, s), 2.24 (3H, s), 3.82 (2H, t), 4.93 (1H, s), 6.08–6.22 (2H, m), 7.19–7.37 (7H, m), 7.67 (2H, d), 7.81 (1H, t), 8.35 (1H, s)

EXAMPLE 16

Synthesis of 2,6-dimethyl-5-(3-phenyl-2-propene-1-yl)carbamoyl]-4-(pyridine-3-yl)-1,4-dihydropyridine-3-carboxylic acid 1) Synthesis of 2-cyanoethyl 2,6-dimethyl-5-(3-phenyl-2-propene-1-ylcarbamoyl)-4-(pyridine-3-yl)-1,4-dihydropyridine-3-carboxylate 516 mg (2.37 mmol) of 3-oxo-N-(3-phenyl-2-propene-1-yl)butyramide, 0.255 ml (2.70 mmol) of 3-pyridylaldehyde and 0.06 ml (0.61 mmol) of piperidine were heated under reflux in the presence of a catalytic amount of p-toluenesulfonic acid in 30 ml of benzene overnight while water was removed. Ethyl acetate was added to the reaction mixture. After washing with a saturated aqueous sodium hydrogencarbonate solution, the organic layer was dried over anhydrous sodium sulfate and then concentrated under reduced pressure to obtain 2-acetyl-3-(pyridine-3-yl)-N-(3-phenyl-2-propene-1-yl)acrylamide. 20 ml of 2-propanol and 365 mg (2.37 mmol) of 2-cyanoethyl 3-aminocrotonate were added to the product, and they were heated at 80° C. under stirring overnight. 2-Propanol was evaporated under reduced pressure, and the residue was purified by the silica gel chromatography (chloroform/methanol=50/1) to obtain the title compound.

Yield: 793 mg (1.79 mmol) (75.5%)

MS (ESI, m/z) 443 (M+H)$^+$ $^1$H-NMR (CDCl$_3$): 2.27 (3H, s), 2.35 (3H, s), 3.84–4.08 (2H, m), 4.27 (2H, t), 4.84 (1H, s), 5.55 (1H, m), 5.77 (1H, m), 6.07 (1H, dt), 6.33 (1H, d), 7.18–7.72 (7H, m), 8.30–8.72 (2H, m)

2) Synthesis of 2,6-dimethyl-5-(3-phenyl-2-propene-1-ylcarbamoyl)-4-(pyridine-3-yl)-1,4-dihydropyridine-3-carboxylic acid The title compound was obtained from 790 mg (1.79 mmol) of 2-cyanoethyl 2,6-dimethyl-5-(3-phenyl-2-propene-1-ylcarbamoyl)-4-(pyridine-3-yl)-1,4-dihydropyridine-3-carboxylate in the same manner as that of Example 4-3).

Yield: 170 mg (0.44 mmol) (24.5%)

MS (ESI, m/z) 388 (M–H)$^-$ $^1$H-NMR (DMSO-d$_6$): 2.07 (3H, s), 2.24 (3H, s), 3.78–3.86 (2H, m),4.0 (1H, s), 6.13 (1H, dt), 6.22 (1H, d), 7.18–7.36 (6H, m), 7.52 (1H, d), 7.83 (1H, t), 8.29–8.37 (2H, m), 8.40 (1H,s)

EXAMPLE 17

Synthesis of 2,6-dimethyl-4-(4-nitrophenyl)-5-[(3-phenyl-2-propene-1-yl)carbamoyl]-1,4-dihydropyridine-3-carboxylic acid 1) Synthesis of 2-acetyl-3-(4-nitrophenyl)-N-(3-phenyl-2-propene-1-yl)acrylamide The title compound was obtained from 500 mg (2.30 mmol) of 3-oxo-N-(3-phenyl-2-propene-1-yl)butyramide and 348 mg (2.30 mmol) of 4-nitrobenzaldehyde in the same manner as that of Example 1-2).

Yield: 424 mg (1.21 mmol) (52.6%)

MS (ESI, m/z) 351 (M+H)$^+$ $^1$H-NMR (CDCl$_3$): 2.46 (3H, s), 4.10 (2H, t), 6.06 (1H, t), 6.29 (1H, br t), 6.48 (1H, d), 7.22–7.32 (5H, m), 7.53 (1H, s), 7.66 (2H, d), 8.12 (2H, d)

2) Synthesis of 2-cyanoethyl 2,6-dimethyl-4-(4-nitrophenyl)-5-[(3-phenyl-2-propene-1-yl)carbamoyl]-1,4-dihydropyridine-3-carboxylate 424 mg (1.21 mmol) of 2-acetyl-3-(4-nitrophenyl)-N-(3-phenyl-2-propene-1-yl)acrylamide and 187 mg (1.21 mmol) of 2-cyanoethyl 3-aminocrotonate were heated at 70° C. under stirring in 10 ml of 2-propanol for 2 days. 2-Propanol was evaporated under reduced pressure, and the residue was purified by the silica gel chromatography (dichloromethane/methanol=100/1) to obtain the title compound.

Yield: 396 mg (0.814 mmol) (67.3%)

MS (ESI, m/z) 487 (M+H$^+$ $^1$H-NMR (CDCl3): 2.21 (3H, s), 2.33 (3H, s), 2.62 (2H, t), 3.98 (2H, dd), 4.23 (2H, t), 4.97 (1H, s), 5.67 (1H, t), 6.05 (1H, dt), 6.32 (1H, d), 7.21–7.32 (5H, m), 7.47 (2H, d), 8.09 (2H, d)

3) Synthesis of 2,6-dimethyl-4-(4-nitrophenyl)-5-[(3-phenyl-2-propene -1-yl)carbamoyl]-1,4-dihydropyridine-3-carboxylic acid 396 mg (0.814 mmol) of 2-cyanoethyl 2,6-dimethyl-4-(4-nitrophenyl)-5-[(3-phenyl-2-propene-1-yl)carbamoyl]-1,4-dihydropyridine-3-carboxylate was dissolved in 10 ml of methanol. 0.895 ml of 1 N aqueous sodium hydroxide solution was added to the solution, and they were stirred at room temperature overnight. 1 N hydrochloric acid was added to the reaction mixture and then methanol was evaporated under reduced pressure. Water was added to the residue, and a precipitate thus obtained was taken by the filtration. The product was washed with water and then with hexane/ethyl acetate (3:1) and dried under reduced pressure to obtain the title compound.

Yield: 289 mg (0.667 mmol) (81.9%)

MS (ESI, m/z) 434 (M+H)$^+$ $^1$H-NMR (DMSO-d$_6$): 2.06 (3H, s), 2.25 (3H, s), 3.82 (2H, br s), 5.00 (1H, s), 6.08–6.22 (2H, m), 7.18–7.29 (5H, m), 7.43 (2H, d), 7.83 (1H, t), 8.10 (2H, d), 8.38 (1H, s)

EXAMPLE 18

Synthesis of 4-(3-chlorophenyl)-2,6-dimethyl-5-{[3-(2-methoxyphenyl)-2-propene-1-yl]carbamoyl}-1,4-dihydropyridine-3-carboxylic acid 1) Synthesis of 2-cyanoethyl 4-(3-chlorophenyl)-2,6-dimethyl-5-{[3-(2-methoxyphenyl)-2-propene-1-yl]carbamoyl}-1,4-dihydropyridine-3-carboxylate 150 mg (0.416 mmol) of mono(2-cyanoethyl) 4-(3-chlorophenyl)-2,6-dimethyl-1,4-dihydropyridine-3,5- dicarboxylate and 81.4 mg (0.499 mmol) of 3-(2-methoxyphenyl)-allylamine were dissolved in 10 ml of dichloromethane. 120 mg (0.624 mmol) of 1-(3-dimethylaminopropyl)-3-ethylcarbodiimide hydrochloride and 63.7 mg (0.416 mmol) of 1-hydroxybenzotriazole were added to the obtained solution under cooling with ice, and they were stirred at room temperature for 2 hours. Dichloromethane was evaporated under reduced pressure. Ethyl acetate was added to the residue, and the product was washed with 1 N hydrochloric acid and then with a saturated aqueous sodium hydrogencarbonate solution. The organic layer was dried over anhydrous sodium sulfate and then concentrated under reduced pressure. The residue was purified by the silica gel chromatography (dichloromethane/methanol=100/1) to obtain the title compound.

Yield: 140 mg (0.279 mmol) (67.0%)

MS (ESI, m/z) 506 (M+H)$^+$ $^1$H-NMR (CDCl$_3$): 2.19 (3H, s), 2.30 (3H, s), 2.58–2.65 (2H, m), 3.82 (3H, s), 3.90–4.01 (2H, m), 4.15–4.68 (2H, m), 4.78 (1H, s), 5.61 (1H, t), 6.06 (1H, dt), 6.36 (1H, s), 6.71 (1H, d), 6.83–6.92 (2H, m), 7.11–7.35 (6H, m)

2) Synthesis of 4-(3-chlorophenyl)-2,6-dimethyl-5-{[3-(2-methoxyphenyl)-2-propene-1-yl]carbamoyl}-1,4-dihydropyridine-3-carboxylic acid The title compound was obtained from 140 mg (0.279 mmol) of 2-cyanoethyl 4-(3-chlorophenyl)-2,6-dimethyl-5-{[3-(2-methoxyphenyl)-2-propene-1-yl]carbamoyl}-1,4-dihydropyridine-3-carboxylate in the same manner as that of Example 4-3).

Yield: 70.0 mg (0.155 mmol) (55.4%)

MS (ESI, m/z) 453 (M+H)$^+$ $^1$H-NMR (DMSO-d$_6$): 2.05 (3H, s), 2.26 (3H, s), 3.78 (3H, s), 3.84 (2H, d), 4.84 (1H, s), 6.11 (1H, dt), 6.63 (1H, d), 6.88–7.00 (2H, m), 7.10–7.24 (5H, m), 7.36 (1H, d), 7.81 (1H, t), 8.30 (1H, s)

EXAMPLE 19

Synthesis of 4-(4-cyanophenyl)-2,6-dimethyl-1,4-dihydropyridine-3,5-carboxylic acid 3-[3-(morpholine-4-yl)-propyl]amide 5-(3-phenyl-2-propene-1-yl)amide 100 mg (0.242 mmol) of 4-(4-cyanophenyl)-2,6-dimethyl-5-[(3-phenyl-2-propene-1-yl)carbamoyl]-1,4-dihydropyridine-3-carboxylic acid and 42.0 mg (0.290 mmol) of N-(3-aminopropyl)morpholine were dissolved in 10 ml of dichloromethane. 69.6 mg (0.363 mmol) of 1-(3-dimethylaminopropyl)-3-ethylcarbodiimide hydrochloride and 37.1 mg (0.242 mmol) of 1-hydroxybenzotriazole were added to the obtained solution under cooling with ice, and they were stirred at room temperature for 3 hours. Dichloromethane was evaporated under reduced pressure. Ethyl acetate was added to the residue, and the product was washed with a saturated aqueous sodium hydrogencarbonate solution. The organic layer was dried over anhydrous sodium sulfate and then concentrated under reduced pressure. The residue was purified by the recrystallization (recrystallization solvent: acetone/petroleum ether) to obtain the title compound.

Yield: 72.0 mg (0.133 mmol) (55.1%)

MS (ESI, m/z) 540 (M+H)$^+$ $^1$H-NMR (DMSO-d$_6$): 1.43 (2H, dt), 2.01 (3H, s), 2.07 (5H, t), 2.22 (4H, t), 3.03 (2H, br s), 3.52 (4H, t), 3.81 (2H, t), 4.97 (1H, s), 6.02–6.18 (2H, m), 7.20–7.36 (7H, m), 7.62 (1H, t), 7.68 (2H, d), 7.83 (1H, s)

EXAMPLE 20

Synthesis of (3-phenyl-2-propene-1-yl) 4-(3-chlorophenyl)-2,6-dimethyl-5-[3-(imidazole-1-yl)propylcarbamoyl]-1,4-dihydropyridine-3-carboxylate The title compound was obtained from 100 mg (0.236 mmol) of mono(3-phenyl-2-propene-1-yl) 4-(3-chlorophenyl)-2,6-dimethyl-1,4-dihydropyridine-3,5-dicarboxylate and 35.5 mg (0.284 mmol) of 1-(3-aminoproyl)imidazole in the same manner as that of Example 19.

Yield: 85.0 mg (0.160 mmol) (67.9%)

MS (ESI, m/z) 531 (M+H)$^+$ $^1$H-NMR (DMSO-d$_6$): 1.74 (2H, t), 2.00 (3H, s), 2.29 (3H, s), 2.99 (2H, q), 3.76 (2H, dt), 4.63 (2H, ddd), 4.90 (1H, s), 6.25 (1H, dt), 6.43 (1H, d), 6.85 (1H, s), 7.07–7.35 (10H, m), 7.51 (1H, s), 7.67 (1H, t), 8.44 (1H, s)

EXAMPLE 21

Synthesis of 4-(3-chlorophenyl)-2,6-dimethyl-5-(phenylcarbamoylmethylcarbamoyl)-1,4-dihydropyridine-3-carboxylic acid 1) Synthesis of t-butyl phenylcarbamoylmethylcarbamate 1.27 g (1.19 mmol) of 1-(3-dimethylaminopropyl)-3-ethylcarbodiimide hydrochloride, 681 mg (5.04 mmol) of 1-hydroxybenzotriazole and 0.95 ml (6.82 mmol) of triethylamine were added to 1.15 g (6.56 mmol) of t-butoxycarbonylglycine in 20 ml of dichloromethane under cooling in an ice bath, and they were stirred at room temperature overnight. Ethyl acetate was added to the reaction mixture, and the product was washed with 0.1 N hydrochloric acid and then with a saturated aqueous sodium hydrogencarbonate solution. The organic layer was dried over anhydrous sodium sulfate and then concentrated under reduced pressure to obtain the title compound.

Yield: 1.30 g (5.19 mmol) (79.1%)

$^1$H-NMR (CDCl$_3$): 1.48 (9H, s), 3.93 (2H, d), 5.28 (1H, brd), 7.12 (1H, t), 7.32 (2H, t), 7.51 (2H, d), 8.17 (1H, brd)

2) Synthesis of 2-amino-N-phenylacetamide 40 ml of dichloromethane and 20 ml of trifluoroacetic acid were added to 687 mg (2.74 mmol) of t-butyl phenylcarbamoylmethylcarbamate, and they were stirred at room temperature for 3 hours. Dichloromethane and trifluoroacetic acid were evaporated under reduced pressure. A saturated aqueous sodium hydrogencarbonate solution was added to the residue. After the extraction with ethyl acetate and then with dichloromethane, the organic layer was dried over anhydrous sodium sulfate and then concentrated under reduced pressure to obtain the title compound.

Yield: 247 mg (1.64 mmol) (59.9%)

$^1$H-NMR (CDCl$_3$): 3.48 (2H, m), 7.04–7.15 (1H, t), 7.20–7.37 (2H, m), 7.60 (2H, d), 9.34 (1H, brd)

3) Synthesis of 2-cyanoethyl 4-(3-chlorophenyl)-2,6-dimethyl-5-(phenylcarbamoylmethylcarbamoyl)-1,4-dihydropyridine-3-carboxylate 179 mg (0.49 mmol) of mono(2-cyanoethyl) 4-(3-chlorophenyl)-2,6-dimethyl-1,4-dihydropyridine-3,5-dicarboxylate, 245mg (1.63 mmol) of 2-amino-N- phenylacetamide, 129 mg (0.67 mmol) of 1-(3-dimethylaminopropyl)-3-ethylcarbodiimide hydrochloride and 11 mg (0.09 mmol) of 4-dimethylaminopyridine were stirred in 10 ml of dichloromethane at room temperature overnight. Ethyl acetate was added to the reaction mixture, and the product was washed with 1 N hydrochloric acid and then with a saturated aqueous sodium hydrogencarbonate solution. The organic layer was dried over anhydrous sodium sulfate and then concentrated under reduced pressure. The residue was purified by the silica gel chromatography (chloroform/methanol=100/1) to obtain the title compound.

Yield: 221 mg (0.45 mmol) (90.7%)

MS (ESI, m/z) 493 (M+H)$^+$ $^1$H-NMR (CDCl$_3$): 2.31 (3H, s), 2.35 (3H, s), 2.64 (2H, t), 3.99 (2H, t), 4.23–4.35 (2H, m), 4.83 (1H, s), 5.74 (1H, s), 6.30 (1H, brd), 7.06–7.33 (7H, m), 7.42 (2H, d), 8.32 (1H, s)

4) Synthesis of 4-(3-chlorophenyl)-2,6-dimethyl-5-(phenylcarbamoylmethylcarbamoyl)-1,4-dihydropyridine-3-carboxylic acid The title compound was obtained from 216 mg (0.44 mmol) of 2-cyanoethyl 4-(3-chlorophenyl)-2,6-dimethyl-5-(phenylcarbamoylmethylcarbamoyl)-1,4-dihydropyridine-3-carboxylate in the same manner as that of Example 4-3).

Yield: 37 mg (0.08 mmol) (19.2%)

MS (ESI, m/z) 438 (M–H)$^-$ $^1$H-NMR (DMSO-d$_6$): 2.15 (3H, s), 2.25 (3H, s), 3.74–3.94 (2H, m), 4.83 (1H, s), 7.03 (1H, t), 7.12–7.33 (6H, m), 7.55 (2H,d), 7.74 (1H, t), 8.40 (1H, s), 9.87 (1H,s)

EXAMPLE 22

Synthesis of 5-acetyl-4-(3-chlorophenyl)-2,6-dimethyl-1,4-dihydropyridine-3-carboxylic acid (3-phenyl-2-propene-1-yl)amide 569 mg (2.62 mmol) of 3-oxo-N-(3-phenyl-2-propene-1-yl)butyramide, 0.3 ml (2.65 mmol) of 3-chlorobenzaldehyde and 0.03 ml (0.34 mmol) of piperidine were heated under reflux in the presence of a catalytic amount of p-toluenesulfonic acid in 30 ml of benzene overnight while water was removed. Ethyl acetate was added to the reaction mixture, and the product was washed with 1 N hydrochloric acid and then with a saturated aqueous sodium hydrogencarbonate solution. The organic layer was dried over anhydrous sodium sulfate and then concentrated under reduced pressure to obtain 2-acetyl-3-(3-chlorophenyl)-N-(3-phenyl-2-propene-1-yl)acrylamide. 20 ml of 2-propanol and 260 mg (2.62 mmol) of 4-amino-3-pentene-2-on were added to the product, and they were heated at 80° C. under stirring for 3 days. 2-Propanol was evaporated under reduced pressure, and the residue was purified by the silica gel chromatography (ethyl acetate) to obtain the title compound.

Yield: 98 mg (0.08 mmol) (8.8%)

MS (ESI, m/z) 419 (M–H)$^-$ $^1$H-NMR (DMSO-d$_6$): 2.05 (3H, s), 2.09 (3H, s), 2.29 (3H, s), 3.88 (2H,t), 4.95 (1H, s), 6.18 (1H, dt), 6.32 (1H, d), 7.09–7.35 (9H, m), 7.94 (1H,t), 8.48 (1H,s)

EXAMPLE 23

Synthesis of (3-phenyl-2-propene-1-yl) 4-(3-chlorophenyl)-2,6-dimethyl-5-[3-(morpholine-4-yl)propylcarbamoyl]-1,4-dihydropyridine-3-carboxylate The title compound was obtained from 100 mg (0.236 mmol) of mono(3-phenyl-2-propene-1-yl) 4-(3-chlorophenyl)-2,6-dimethyl-1,4-dihydropyridine-3,5-dicarboxylate and 41.0 mg (0.284 mmol) of N-(3-aminopropyl)morpholine in the same manner as that of Example 18-1).

Yield: 120 mg (0.218 mmol) (92.4%)

MS (ESI, m/z) 550 (M+H)$^+$ $^1$H-NMR (CDCl$_3$): 1.55 (2H, t), 2.16 (3H, s), 2.20–2.31 (6H, m), 2.32 (3H, s), 3.12–3.25 (1H, m), 3.32–3.42 (1H, m), 3.59 (4H, dd), 4.70 (2H, ddd), 4.86 (1H, s), 6.14–6.23 (2H, m), 6.30 (1H, t), 6.48 (1H, d), 7.11–7.34 (9H, m)

EXAMPLE 24

Synthesis of (R)-1-phenylethyl 4-(3-chlorophenyl)-2,6-dimethyl-5-(3-phenyl-2-propene-1-ylcarbamoyl)-1,4-dihydropyridine-3-carboxylate 81 mg (0.192 mmol) of 4-(3-chlorophenyl)-2,6-dimethyl-5-(3-phenyl-2-propene-1-ylcarbamoyl)-1,4-dihydropyridine-3-carboxylic acid, 0.08 ml (0.67 mmol) of R-(+)-1-phenylethanol, 70 mg (0.37 mmol) of 1-(3-dimethylaminopropyl)-3-ethylcarbodiimide hydrochloride and 6 mg (0.05 mmol) of 4-dimethylaminopyridine were stirred in 10 ml of dichloromethane at room temperature for 3 days. Ethyl acetate was added to the reaction mixture, and the product was washed with 1 N hydrochloric acid. The organic layer was dried over anhydrous sodium sulfate and then concentrated under reduced pressure. The residue was purified by the silica gel chromatography (hexane/ethyl acetate=1/1) to obtain the title compound.

Yield: 85 mg (0.16 mmol) (84.3%)

MS (ESI, m/z) 527 (M+H)$^+$ $^1$H-NMR (CDCl$_3$): 1.47 (3H, dd), 2.24 (3H, d), 2.31 (3H, d), 3.87–4.06 (2H, m), 4.84 (1H, d), 5.42 (1H, t), 5.49 (1H, s), 5.78–5.91 (1H, m), 6.06 (1H, dt), 6.28 (1H, d), 7.04–7.34 (14H, m)

EXAMPLE 25

Synthesis of 2-cyanoethyl 4-(3-chlorophenyl)-2,6-dimethyl-5-{[3-(pyridine-4-yl)-2-propene-1-yl]carbamoyl}-1,4-dihydropyridine-3-carboxylate 221 mg (0.610 mmol) of 3-pyridine-4-yl-allylamine and 200 mg (0.554 mmol) of mono(2-cyanoethyl) 4-(3-chlorophenyl)-2,6-dimethyl-1,4-dihydropyridine-3,5-dicarboxylate were dissolved in 10 ml of DMF. 159 mg (0.831 mmol) of 1-(3-dimethylaminopropyl)-3-ethylcarbodiimide hydrochloride and 123 mg (1.22 mmol) of triethylamine were added to the obtained solution under cooling with ice, and they were stirred at room temperature for 2 days. DMF was evaporated under reduced pressure. After the extraction with a saturated aqueous sodium hydrogencarbonate solution and ethyl acetate, the organic layer was dried over anhydrous sodium sulfate and then concentrated under reduced pressure. The residue was purified by the silica gel chromatography (dichloromethane/methanol= 100/1 to 10/1) to obtain the title compound.

Yield: 161 mg (0.338 mmol) (60.9%)

MS (ESI, m/z) 477 (M+H)$^+$ $^1$H-NMR (CDCl$_3$): 2.26 (3H, s), 2.31 (3H, s), 2.64 (2H, t), 4.01 (2H, t), 4.26 (2H, t), 4.83 (1H, s), 5.86 (1H, t), 6.14 (1H, d), 6.31 (1H, dt), 6.71 (1H, s), 7.10–7.31 (6H, m), 8.48 (2H, d)

EXAMPLE 26

Synthesis of 4-(3-chlorophenyl)-2,6-dimethyl-5-{[3-(pyridine-4-yl)-2-propene-1-yl]carbamoyl}-1,4-dihydropyridine-3-carboxylic acid 161 mg (0.338 mmol) of the compound obtained in Example 25 was dissolved in 10 ml of methanol. 0.372 ml of 1 N aqueous sodium hydroxide solution was added to the obtained solution, and they were stirred at room temperature for 4 hours. After the addition of 1 N hydrochloric acid, methanol was evaporated under reduced pressure. Water was added to the residue, and a precipitate thus formed was taken by the filtration and then recrystallized (recrystallization solvent: methanol/isopropyl ether) to obtain the title compound.

Yield: 52.0 mg (0.123 mmol) (36.3%)
MS (ESI, m/z) 424 (M+H)$^+$
$^1$H-NMR (CDCl3): 2.34 (3H, s), 2.58 (3H, s), 4.02 (2H, t), 5.05 (1H, s), 6.00–6.18 (2H, m), 6.36 (1H, t), 6.58 (1H, s), 7.08–7.41 (6H, m), 8.50 (2H, d)

EXAMPLE 27

Synthesis of 2-cyanoethyl 4-(furan-3-yl)-2,6-dimethyl-5-[(3-phenyl-2-propene-1-yl)carbamoyl]-1,4-dihydropyridine-3-carboxylate 1) Synthesis of 2-acetyl-3-(furan-3-yl)-N-(3-phenyl-2-propene-1-yl)acrylamide The title compound was obtained from 500 mg (2.30 mmol) of 3-oxo-N-(3-phenyl-2-propene-1-yl)butyramide and 221 mg (2.30 mmol) of 3-furaldehyde in the same manner as that of Example 4-1).

Yield: 477 mg (1.62 mmol) (70.2%)
MS (ESI, m/z) 296 (M+H)$^+$
$^1$H-NMR (CDCl$_3$): 2.41 (3H, s), 4.19 (2H, t), 6.22 (1H, dt), 6.38 (1H, br s), 6.60 (1H, d), 6.66 (1H, s), 7.21–7.41 (7H, m), 7.82 (1H, s)

2) Synthesis of 2-cyanoethyl 4-(furan-3-yl)-2,6-dimethyl-5-[(3-phenyl-2-propene-1-yl)carbamoyl]-1,4-dihydropyridine-3-carboxylate The title compound was obtained from 477 mg (1.62 mmol) of 2-acetyl-3-(furan-3-yl)-N-(3-phenyl-2-propene-1-yl)acrylamide and 250 mg (1.62 mmol) of 2-cyanoethyl 3-aminocrotonate in the same manner as that of Example 1-3).

Yield: 368 mg (0.853 mmol) (52.6%)
MS (ESI, m/z) 432 (M+H)$^+$
$^1$H-NMR (CDCl$_3$): 2.30 (3H, s), 2.31 (3H, s), 2.72 (2H, t), 4.04 (2H, dt), 4.35 (2H, dt), 4.73 (1H, s), 5.72 (1H, br s), 5.79 (1H, br t), 6.15 (1H, dt), 6.33 (1H, t), 7.20–7.34 (8H, m)

EXAMPLE 28

Synthesis of 2-cyanoethyl 4-(3-chlorophenyl)-2,6-dimethyl-5-[3-(imidazole-1-yl)propylcarbamoyl]-1,4-dihydropyridine-3-carboxylate The title compound was obtained from 150 mg (0.416 mmol) of mono(2-cyanoethyl) 4-(3-chlorophenyl)-2,6-dimethyl-1,4-dihydropyridine-3,5-dicarboxylate and 62.5 mg (0.499 mmol) of 1-aminopropylimidazole in the same manner as that of Example 25.

Yield: 107 mg (0.229 mmol) (55.1%)
MS (ESI, m/z) 468 (M+H)$^+$
$^1$H-NMR (CDCl$_3$): 1.85 (2H, t), 2.17 (3H, s), 2.31 (3H, s), 2.63 (2H, t), 3.10–3.30 (2H, m), 3.77 (2H, dd), 4.23 (2H, t), 4.80 (1H, s), 6.12 (1H, t), 6.88 (1H, s), 7.00 (1H, s), 7.06 (1H, s), 7.08–7.37 (5H, m)

EXAMPLE 29

Synthesis of 2-cyanoethyl 4-(3-chlorophenyl)-2,6-dimethyl-5-[3-(morpholine-4-yl)propylcarbamoyl]-1,4-dihydropyridine-3-carboxylate The title compound was obtained from 150 mg (0.416 mmol) of mono(2-cyanoethyl) 4-(3-chlorophenyl)-2,6-dimethyl-1,4-dihydropyridine-3,5-dicarboxylate and 72.0 mg (0.499 mmol) of N-(3-aminopropyl)morpholine in the same manner as that of Example 25.

Yield: 110 mg (0.226 mmol) (54.3%)
MS (ESI, m/z) 487 (M+H)$^+$
$^1$H-NMR (CDCl$_3$): 1.57 (2H, dd), 2.14 (3H, s), 2.22–2.34 (9H, m), 2.60 (2H, t), 3.15–3.25 (1H, m), 3.35–3.45 (1H, m), 3.60 (4H, dd), 4.12–4.29 (2H, m), 4.82 (1H, s), 6.40–6.45 (2H, m), 7.13–7.29 (4H, m)

EXAMPLE 30

Synthesis of 2-cyanoethyl 4-(3-chlorophenyl)-2,6-dimethyl-5-[3-(2-oxopyrrolidine-1-yl)propylcarbamoyl]-1,4-dihydropyridine-3-carboxylate The title compound was obtained from 150 mg (0.416 mmol) of mono(2-cyanoethyl) 4-(3-chlorophenyl)-2,6-dimethyl-1,4-dihydropyridine-3,5-dicarboxylate and 71.0 mg (0.499 mmol) of 1-(3-aminopropyl)-2-pyrrolidinone in the same manner as that of Example 18-1).

Yield: 117 mg (0.241 mmol) (58.0%)
MS (ESI, m/z) 485 (M+H)$^+$
$^1$H-NMR (CDCl$_3$): 1.55 (2H, t), 1.98–2.08 (4H, m), 2.18 (3H, s), 2.32 (3H, s), 2.38 (2H, t), 2.61–2.66 (2H, m), 2.94–3.11 (3H, m), 3.25–3.40 (3H, m), 4.23 (2H, t), 4.91 (1H, s), 6.22 (1H, s), 6.61 (1H, t), 7.10–7.29 (4H, m)

EXAMPLE 31

Synthesis of 2-cyanoethyl 4-(3-chlorophenyl)-2,6-dimethyl-5-[3-(pyrrolidine-1-yl)propylcarbamoyl]-1,4-dihydropyridine-3-carboxylate The title compound was obtained from 150 mg (0.416 mmol) of mono(2-cyanoethyl) 4-(3-chlorophenyl)-2,6-dimethyl-1,4-dihydropyridine-3,5-dicarboxylate and 64.0 mg (0.499 mmol) of 1-(3-aminopropyl)pyrrolidine in the same manner as that of Example 18-1).

Yield: 147 mg (0.312 mmol) (75.0%)
MS (ESI, m/z) 471 (M+H)$^+$
$^1$H-NMR (CDCl$_3$): 1.52–1.65 (2H, m), 1.70 (4H, br t), 2.12 (3H, s), 2.21 (3H, s), 2.31–2.46 (6H, m), 2.59 (2H, t), 3.10–3.22 (1H, m), 3.32–3.42 (1H, m), 4.15–4.29 (2H, m), 4.80 (1H, s), 6.84 (1H, t), 7.08–7.22 (4H, m)

EXAMPLE 32

Synthesis of 2-cyanoethyl 4-(3-chlorophenyl)-2,6-dimethyl-5-[3-(4-methoxyphenyl)-2-propene-1-ylcarbamoyl]-1,4-dihydropyridine-3-carboxylate The title compound was obtained from 234 mg (0.648 mmol) of mono(2-cyanoethyl) 4-(3-chlorophenyl)-2,6-dimethyl-1,4-dihydropyridine-3,5-dicarboxylate and 127 mg (0.778 mmol) of 3-(4-methoxyphenyl)-allylamine in the same manner as that of Example 18-1).

Yield: 182 mg (0.360 mmol) (55.5%)
MS (ESI, m/z) 506 (M+H)$^+$
$^1$H-NMR (CDCl$_3$): 2.37 (3H, s), 2.40 (3H, s), 2.65 (2H, t), 3.75–3.81 (5H, m), 4.23–4.38 (2H, m), 5.26 (1H, s), 6.75–6.88 (3H, m), 7.17–7.42 (6H, m), 8.00 (1H, d)

EXAMPLE 33

Synthesis of 4-(3-chlorophenyl)-2,6-dimethyl-5-(4-phenylbutylcarbamoyl)-1,4-dihydropyridine-3-carboxylic acid 1) Synthesis of 2-cyanoethyl 4-(3-chlorophenyl)-2,6-dimethyl-5-(4-phenylbutylcarbamoyl)-1,4-dihydropyridine-3-carboxylate The title compound was obtained from 200 mg (0.554 mmol) of mono(2-cyanoethyl) 4-(3-chlorophenyl)-2,6- dimethyl-1,4-dihydropyridine-3,5-dicarboxylate and 99.2 mg (0.665 mmol) of 1-amino-4-phenylbutane in the same manner as that of Example 18-1).

Yield: 266 mg (0.541 mmol) (97.6%)

MS (ESI, m/z) 492 (M+H)$^+$ $^1$H-NMR (CDCl$_3$): 1.44 (4H, br), 2.14 (3H, s), 2.53 (3H, s), 2.50–2.60 (4H, m), 3.10–3.28 (2H, m), 4.19–4.24 (2H, m), 4.74 (1H, s), 5.46 (1H, br), 6.64 (1H, s), 7.10–7.23 (9H, m)

2) Synthesis of 4-(3-chlorophenyl)-2,6-dimethyl-5-(4-phenylbutylcarbamoyl)-1,4-dihydropyridine-3-carboxylic acid The title compound was obtained from 266 mg (0.541 mmol) of 2-cyanoethyl 4-(3-chlorophenyl)-2,6-dimethyl-5-(4-phenylbutylcarbamoyl)-1,4-dihydropyridine-3-carboxylate in the same manner as that of Example 4-3).

Yield: 146 mg (0.333 mmol) (61.5%)

MS (ESI, m/z) 439 (M+H)$^+$ $^1$H-NMR (DMSO-d$_6$): 1.32–1.45 (4H, m), 1.98 (3H, s), 2.23 (3H, s), 2.51 (2H, br), 3.05 (2H, t), 4.79 (1H, s), 7.05–7.28 (9H, m), 7.51 (1H, t), 8.23 (1H, s)

EXAMPLE 34

Synthesis of 4-(3-chlorophenyl)-2,6-dimethyl-5-(3,3-diphenylpropylcarbamoyl)-1,4-dihydropyridine-3-carboxylic acid 1) Synthesis of 2-cyanoethyl 4-(3-chlorophenyl)-2,6-dimethyl-5-(3,3-diphenylpropylcarbamoyl)-1,4-dihydropyridine-3-carboxylate 219 mg (0.61 mmol) of mono(2-cyanoethyl) 4-(3-chlorophenyl)-2,6-dimethyl-1,4-dihydropyridine-3,5-dicarboxylate, 138 mg (0.72 mmol) of 1-(3-dimethylaminopropyl)-3-ethylcarbodiimide hydrochloride, 201 mg (0.95 mmol) of 3,3-diphenylpropylamine and 20 mg (0.16 mmol) of 4-dimethylaminopyridine were stirred in 10 ml of dichloromethane at room temperature overnight. 2 N hydrochloric acid was added to the reaction mixture. After the extraction with dichloromethane, the organic layer was dried over anhydrous sodium sulfate and then concentrated under reduced pressure. The residue was purified by the silica gel chromatography (hexane/ethyl acetate=1/1) to obtain the title compound.

Yield: 280mg (0.51 mmol) (83.3%)

MS (ESI, m/z) 554 (M+H)$^+$ $^1$H-NMR (CDCl$_3$): 2.05–2.23 (2H, m), 2.21 (3H, s), 2.32 (3H, s), 2.64 (2H, t), 3.06–3.22 (2H, m), 3.72 (1H, t), 4.20–4.35 (2H, m), 4.73 (1H, s), 5.31 (1H, t), 5.58 (1H, s), 7.09–7.30 (14H, m)

2) Synthesis of 4-(3-chlorophenyl)-2,6-dimethyl-5-(3,3-diphenylpropylcarbamoyl)-1,4-dihydropyridine-3-carboxylic acid The title compound was obtained from 275 mg (0.50 mmol) of 2-cyanoethyl 4-(3-chlorophenyl)-2,6-dimethyl-5-(3,3-diphenylpropylcarbamoyl)-1,4-dihydropyridine-3-carboxylate in the same manner as that of Example 4-3).

Yield: 158 mg (0.32 mmol) (63.1%)

MS (ESI, m/z) 499 (M−H)$^−$ $^1$H-NMR (DMSO-d6): 2.01 (3H, s), 2.03–2.17 (2H, s), 2.23 (3H, s), 2.82–3.03 (2H,m), 3.84 (1H,t), 4.82 (1H, s), 7.08–7.31 (14H, m), 7.56 (1H, t), 8.26 (1H, s)

EXAMPLE 35

Synthesis of 4-(3-chlorophenyl)-2,6-dimethyl-5-(4-phenylpiperazine-1-carbonyl)-1,4-dihydropyridine-3-carboxylic acid 1) Synthesis of 2-cyanoethyl 4-(3-chlorophenyl)-2,6-dimethyl-5-(4-phenylpiperazine-1-carbonyl)-1,4-dihydropyridine-3-carboxylate 216 mg (0.60 mmol) of mono(2-cyanoethyl) 4-(3-chlorophenyl)-2,6-dimethyl-1,4-dihydropyridine-3,5-dicarboxylate, 147 mg (0.76 mmol) of 1-(3-dimethylaminopropyl)-3-ethylcarbodiimide hydrochloride, 0.14 ml (0.92 mmol) of 1-phenylpiperazine and 25 mg (0.20 mmol) of 4-dimethylaminopyridine were stirred in 10 ml of dichloromethane at room temperature for 4 days. A saturated aqueous sodium hydrogencarbonate solution was added to the reaction mixture. After the extraction with dichloromethane, the organic layer was dried over anhydrous sodium sulfate and then concentrated under reduced pressure. The residue was purified by the silica gel chromatography (chloroform/methanol=100/1) to obtain the title compound Yield: 304 mg (0.60 mmol) (100%)

MS (ESI, m/z) 505 (M+H)$^+$ $^1$H-NMR (CDCl$_3$): 1.80 (3H, s), 2.40 (3H, s), 2.36–2.50 (2H,m), 2.60–3.45 8H, m), 4.06–4.25 (2H, m), 4.90 (1H, s), 5.38 (1H, s), 6.76–6.96 (3H, m), 7.10–7.29 (6H, m)

2) Synthesis of 4-(3-chlorophenyl)-2,6-dimethyl-5-(4-phenylpiperazine-1-carbonyl)-1,4-dihydropyridine-3-carboxylic acid The title compound was obtained from 298 mg (0.59 mmol) of 2-cyanoethyl 4-(3-chlorophenyl)-2,6-dimethyl-5-(4-phenylpiperazine-1-carbonyl)-1,4-dihydropyridine-3-carboxylate in the same manner as that of Example 4-3).

Yield: 167 mg (0.37 mmol) (62.6%)

MS (ESI, m/z) 450 (M−H)$^−$ $^1$H-NMR (DMSO-d$_6$): 1.71 (3H, s), 2.29 (3H, s), 2.55–3.45 (8H,m), 4.67 (1H,s), 6.76–6.88 (3H, m), 7.00–7.08 (2H, m), 7.13–7.31 (4H, m), 8.29 (1H, s)

EXAMPLE 36

Synthesis of 4-(3-chlorophenyl)-6-ethyl-2-methyl-5-(3-phenyl-2-propene-1-ylcarbamoyl)-1,4-dihydropyridine-3-carboxylic acid 1) Synthesis of benzyl 3-oxovalerate 2.50 g (19.2 mmol) of methyl 3-oxovalerate, 6.23 g (57.6 mmol) of benzyl alcohol and 234 mg (1.92 mmol) of 4-dimethylaminopyridine were heated under reflux in 30 ml of toluene overnight. Ethyl acetate was added to the reaction solution. After washing with 1 N hydrochloric acid, the organic layer was dried over anhydrous sodium sulfate and then concentrated under reduced pressure. The residue was purified by the silica gel chromatography (hexane/ethyl acetate=10/1) to obtain the title compound.

Yield: 1.59 g (7.71 mmol) (40.2%)

MS (ESI, m/z) 207 (M+H)$^+$ $^1$H-NMR (CDCl$_3$): 1.07 (3H, t), 2.54 (2H, dd), 3.49 (2H, s), 5.18 (2H, s), 7.36 (5H, br)

2) Synthesis of benzyl 2-propionyl-3-(3-chlorophenyl)acrylate (mixture of E:Z=1:1)

1.59 g (7.71 mmol) of benzyl 3-oxovalerate, 1.08 g (7.71 mmol) of 3-chlorobenzaldehyde and 65.7 mg (0.771 mmol)

of piperidine were heated under reflux in the presence of a catalytic amount of p-toluenesulfonic acid in 50 ml of benzene for 6 hours while water was removed. Benzene was evaporated under reduced pressure. Ethyl acetate was added to the reaction mixture. After washing with 1 N hydrochloric acid and then with a saturated aqueous sodium hydrogencarbonate solution, the organic layer was dried over anhydrous sodium sulfate and then concentrated under reduced pressure. The residue was purified by the silica gel chromatography (hexane/ethyl acetate=10/1) to obtain the title compound.

Yield: 2.17 g (6.68 mmol) (86.7%)

$^1$H-NMR (CDCl$_3$): 1.06–1.16 (3H, m), 2.55 (1H, dd), 2.71 (1H, dd), 5.28 (2H, d), 7.18 (1H, s), 7.30–7.53 (9H, m)

3) Synthesis of 3-benzyl 5-(2-cyanoethyl) 4-(3-chlorophenyl)-2-ethyl-6-methyl-1,4-dihydropyridine-3,5-dicarboxylate 1.00 g (3.08 mmol) of benzyl 2-propionyl-3-(3-chlorophenyl)acrylate (mixture of E:Z=1:1) and 475 mg (3.08 mmol) of 2-cyanoethyl 3-aminocrotonate were heated under reflux in 10 ml of 2-propanol at 80° C. for 2 days. 2-Propanol was evaporated under reduced pressure, and the residue was purified by the silica gel chromatography (dichloromethane/methanol=100/1) to obtain the title compound.

Yield: 631 mg (1.36 mmol) (44.2%)

MS (ESI, m/z) 465 (M+H)$^+$ $^1$H-NMR (DMSO-d$_6$): 1.09 (3H, t), 2.24 (3H, s), 2.39–2.58 (2H, m), 3.72–3.92 (2H, m), 4.85 (1H, s), 6.10–6.27 (2H, m), 7.11–7.36 (9H, m), 7.85 (1H, t), 8.27 (1H, s)

4) Synthesis of 5-(2-cyanoethyl) 4-(3-chlorophenyl)-2-ethyl-6-methyl-1,4-dihydropyridine-3,5-dicarboxylate 631 mg (1.36 mmol) of 3-benzyl 5-(2-cyanoethyl) 4-(3-chlorophenyl)-2-ethyl-6-methyl-1,4-dihydropyridine-3,5-dicarboxylate was dissolved in 20 ml of ethyl acetate, and the obtained solution was stirred in the presence of 10% palladium/carbon at room temperature in hydrogen atmosphere under atmospheric pressure for 2 days. 10% palladium/carbon was filtered off, and the filtrate was concentrated under reduced pressure. The residue was purified by the silica gel chromatography (dichloromethane/methanol=10/1) to obtain the title compound.

Yield: 371 mg (0.990 mmol) (72.8%)

MS (ESI, m/z) 373 (M–H)$^-$ $^1$H-NMR (CDCl$_3$): 1.19–1.31 (3H, m), 2.37 (3H, s), 2.63–2.95 (4H, m), 4.23–4.32 (2H, m), 4.97 (1H, s), 5.89 (1H, s), 7.10–7.27 (4H, m)

5) Synthesis of 2-cyanoethyl 4-(3-chlorophenyl)-6-ethyl-2-methyl-5-(3-phenyl-2-propene-1-ylcarbamoyl)-1,4-dihydropyridine-3-carboxylate The title compound was obtained from 251 mg (0.670 mmol) of 5-(2-cyanoethyl) 4-(3-chlorophenyl)-2-ethyl-6-methyl-1,4-dihydropyridine-3,5-dicarboxylate and 107 mg (0.804 mmol) of cinnamylamine in the same manner as that of Example 18-1).

Yield: 320 mg (0.653 mmol) (97.5%)

MS (ESI, m/z) 490 (M+H)$^+$ $^1$H-NMR (CDCl$_3$): 1.22 (3H, t), 2.31 (3H, s), 3.97 (2H, br), 2.58–2.66 (2H, m), 4.78 (1H, s), 5.59 (1H, t), 6.01–6.10 (1H, m), 6.28 (1H, d), 7.16–7.29 (9H, m)

6) Synthesis of 4-(3-chlorophenyl)-6-ethyl-2-methyl-5-(3-phenyl-2-propene-1-ylcarbamoyl)-1,4-dihydropyridine-3-carboxylic acid The title compound was obtained from 320 mg (0.653 mmol) of 2-cyanoethyl 4-(3-chlorophenyl)-6-ethyl-2-methyl-5-(3-phenyl-2-propene-1-ylcarbamoyl)-1,4-dihydropyridine-3-carboxylate in the same manner as that of Example 4–3).

Yield: 168 mg (0.384 mmol) (58.9%)

MS (ESI, m/z) 437 (M+H)$^+$ $^1$H-NMR (DMSO-d$_6$): 1.09 (3H, t), 2.24 (3H, s), 2.38–2.58 (2H, m), 3.72–3.92 (2H, m), 4.85 (1H, s), 6.10–6.27 (2H, m), 7.10–7.36 (9H, m), 7.85 (1H, t), 8.27 (1H, s)

EXAMPLE 37

Synthesis of 4-(3-chlorophenyl)-2,6-dimethyl-5-(2-phenylethylcarbamoyl)-1,4-dihydropyridine-3-carboxylic acid

1) Synthesis of 2-cyanoethyl 4-(3-chlorophenyl)-2,6-dimethyl-5-(2-phenylethylcarbamoyl)-1,4-dihydropyridine-3-carboxylate The title compound was obtained from 215 mg (0.60 mmol) of mono(2-cyanoethyl) 4-(3-chlorophenyl)-2,6-dimethyl-1,4-dihydropyridine-3,5-dicarboxylate and 0.12 ml (0.96 mmol) of 2-phenylethylamine in the same manner as that of Example 34-1).

Yield: 225 mg (0.49 mmol) (80.8%)

MS (ESI, m/z) 464 (M+H)$^+$ $^1$H-NMR (CDCl$_3$): 2.20 (3H, s), 2.31 (3H, s), 2.63 (2H, t), 2.65–2.80 (2H, m), 3.04–3.63 (2H, m), 4.19–4.35 (2H, m), 4.64 (1H, s), 5.30 (1H, t), 5.60 (1H, s), 7.01–7.31 (9H, m)

2) Synthesis of 4-(3-chlorophenyl)-2,6-dimethyl-5-(2-phenylethylcarbamoyl)-1,4-dihydropyridine-3-carboxylate The title compound was obtained from 220 mg (0.60 mmol) of 2-cyanoethyl 4-(3-chlorophenyl)-2,6-dimethyl-5-(2-phenylethylcarbamoyl)-1,4-dihydropyridine-3-carboxylate in the same manner as that of Example 4-3).

Yield: 158 mg (0.32 mmol) (63.1%)

MS (ESI, m/z) 409 (M–H)$^-$ $^1$H-NMR (DMSO-d$_6$): 1.96 (3H, s), 2.23 (3H, s), 2.60–2.73 (2H, s), 3.21–3.36 (2H,m), 4.78 (1H, s), 7.04–7.29 (9H, m), 7.54 (1H, t), 8.26 (1H, s)

EXAMPLE 38

Synthesis of 4-(3-chlorophenyl)-2,6-dimethyl-5-(2-phenoxyethylcarbamoyl)-1,4-dihydropyridine-3-carboxylic acid

1) Synthesis of 2-cyanoethyl 4-(3-chlorophenyl)-2,6-dimethyl-5-(2-phenoxyethylcarbamoyl)-1,4-dihydropyridine-3-carboxylate The title compound was obtained from 200 mg (0.554 mmol) of mono(2-cyanoethyl) 4-(3-chlorophenyl)-2,6-dimethyl-1,4-dihydropyridine-3,5-dicarboxylate and 91.3 mg (0.665 mmol) of 2-phenoxyethylamine in the same manner as that of Example 18-1).

Yield: 151 mg (0.315 mmol) (56.8%)

MS (ESI, m/z) 480 (M+H)$^+$ $^1$H-NMR (CDCl$_3$): 2.20 (3H, s), 2.30 (3H, s), 2.57 (2H, t), 3.59 (2H, t), 3.92 (2H, t), 4.18–4.26 (2H, m), 4.74 (1H, s), 5.90 (1H, t), 6.26 (1H, s), 6.81 (2H, d), 6.96 (1H, t), 7.06–7.09 (2H, m), 7.15–7.19 (1H, m), 7.23–7.30 (3H, m)

2) Synthesis of 4-(3-chlorophenyl)-2,6-dimethyl-5-(2-phenoxylethylcarbamoyl)-1,4-dihydropyridine-3-carboxylic acid The title compound was obtained from 151 mg (0.315 mmol) of 2-cyanoethyl 4-(3-chlorophenyl)-2,6-dimethyl-5-(2-phenylbutylcarbamoyl)-1,4-dihydropyridine-3-carboxylate in the same manner as that of Example 4-3).

Yield: 80.2 mg (0.188 mmol) (59.6%)

MS (ESI, m/z) 427 (M+H)$^+$ $^1$H-NMR (DMSO-d$_6$): 2.02 (3H, s), 2.24 (3H, s), 3.00 (2H, br), 3.92 (2H, t), 4.81 (1H, s), 6.88–6.96 (4H, m), 7.13 (5H, br), 7.28 (2H, t), 7.72 (1H, t), 8.30 (1H, s)

EXAMPLE 39

Synthesis of 5-(1-benzylpiperidine-4-ylcarbamoyl)-4-(3-chlorophenyl)-2,6-dimethyl-1,4-dihydropyridine-3-carboxylic acid

1) Synthesis of 2-cyanoethyl 5-(1-benzylpiperidine-4-ylcarbamoyl)-4-(3-chlorophenyl)-2,6-dimethyl-1,4-dihydropyridine-3-carboxylate The title compound was obtained from 217 mg (0.60 mmol) of mono(2-cyanoethyl) 4-(3-chlorophenyl)-2,6-dimethyl-1,4-dihydropyridine-3,5-dicarboxylate and 0.18 ml (0.88 mmol) of 4-amino-1-benzylpiperidine in the same manner as that of Example 35–1).

Yield: 177 mg (0.33 mmol) (55.3%)

MS (ESI, m/z) 533 (M+H)$^+$ $^1$H-NMR (CDCl$_3$): 1.18–1.40 (2H, m), 1.67–1.88 (2H, m), 2.02–2.19 (2H, m), 2.21 (3H, s), 2.33 (3H, s), 2.52–2.68 (2H, m), 2.62 (2H, t), 3.44 (2H, s), 3.70–3.84 (1H, m), 4.22–4.32 (2H, m), 4.70 (1H, s), 5.21 (1H, d), 5.57 (1H, s), 7.17–7.31 (9H, m)

2) Synthesis of 5-(1-benzylpiperidine-4-ylcarbamoyl)-4-(3-chlorophenyl)-2,6-dimethyl-1,4-dihydropyridine-3-carboxylic acid The title compound was obtained from 171 mg (0.32 mmol) of 2-cyanoethyl 5-(1-benzylpiperidine-4-ylcarbamooyl)-4-(3-chlorophenyl)-2,6-dimethyl-1,4-dihydropyridine-3-carboxylate in the same manner as that of Example 4-3).

Yield: 95 mg (0.20 mmol) (61.8%)

MS (ESI, m/z) 478 (M–H)$^-$ $^1$H-NMR (DMSO-d$_6$): 1.21–1.65 (4H, m), 1.88–2.02 (2H, m), 1.95 (3H, s), 2.25 (3H, s), 2.62–2.80 (2H, m), 3.42 (2H, m), 3.49–3.65 (1H, m), 4.78 (1H, s), 7.03–7.40 (10H, m), 8.23 (1H, s)

EXAMPLE 40

Synthesis of 4-(3-chlorophenyl)-6-ethyl-2-methyl-5-(3-phenylpropylcarbamoyl)-1,4-dihydropyridine-3-carboxylic acid

1) Synthesis of 2-cyanoethyl 4-(3-chlorophenyl)-6-ethyl-2-methyl-5-(3-phenylpropylcarbamoyl)-1,4-dihydropyridine-3-carboxylate The title compound was obtained from 250 mg (0.667 mmol) of 5-(2-cyanoethyl) 4-(3-chlorophenyl)-2-ethyl-6-methyl-1,4-dihydropyridine-3,5-dicarboxylate and 108 mg (0.800 mmol) of 3-phenylpropylamine in the same manner as that of Example 18-1).

Yield: 161 mg (0.327 mmol) (49.1%)

MS (ESI, m/z) 492 (M+H)$^+$ $^1$H-NMR (CDCl3): 1.18 (3H, t), 1.64–1.74 (2H, m), 2.29 (3H, s), 2.46 (2H, t), 2.51–2.63 (4H, m), 3.10–3.24 (2H, m), 4.18–4.28 (2H, m), 4.73 (1H, s), 5.43 (1H, t), 6.51 (1H, s), 7.03–7.32 (9H, m)

2) Synthesis of 4-(3-chlorophenyl)-6-ethyl-2-methyl-5-(3-phenylpropylcarbamoyl)-1,4-dihydropyridine-3-carboxylic acid The title compound was obtained from 161 mg (0.327 mmol) of 2-cyanoethyl 4-(3-chlorophenyl)-6-ethyl-2-methyl-5-(3-phenylpropylcarbamoyl)-1,4-dihydropyridine-3-carboxylate in the same manner as that of Example 4-3).

Yield: 78.0 mg (0.178 mmol) (54.3%)

MS (ESI, m/z) 439 (M+H)$^+$ $^1$H-NMR (DMSO-d$_6$): 1.07 (3H, t), 1.62 (2H, quint), 2.24 (3H, s), 2.32–2.47 (4H, m), 2.94–3.14 (2H, m), 4.79 (1H, s), 7.11–7.28 (9H, m), 7.60 (1H, t), 8.21 (1H, s)

The structural formulae of the compounds obtained in Examples 1 to 40 are shown in the following Table together with Example numbers.

1

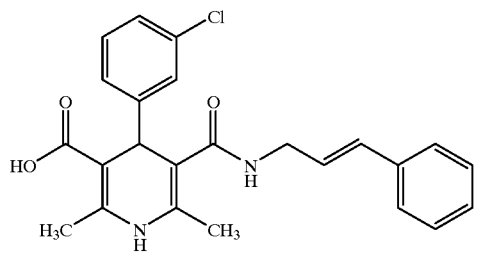

5

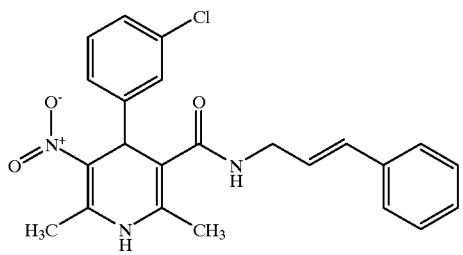

-continued
2
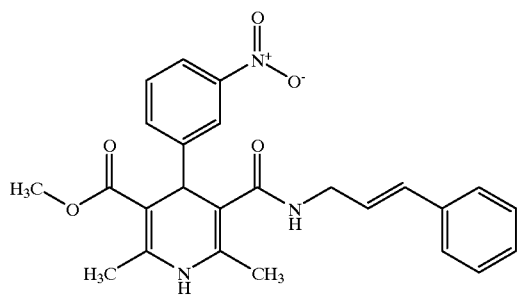
6
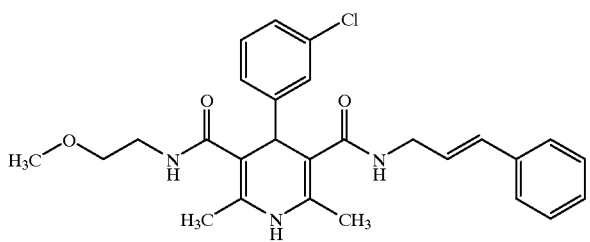
3
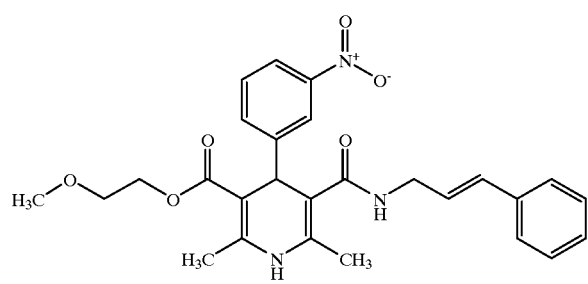
7
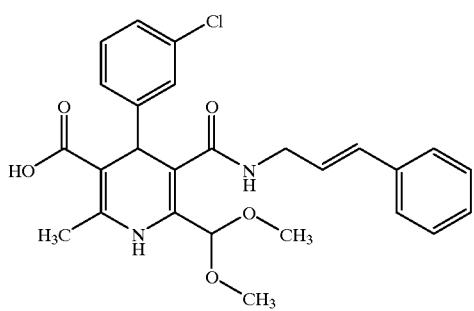
4
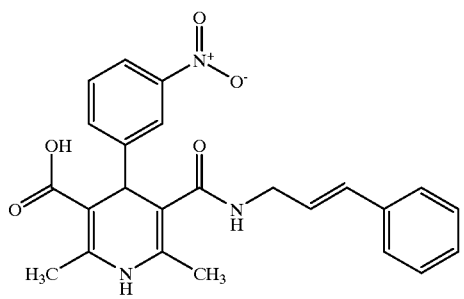
8
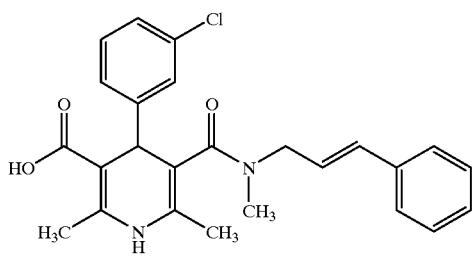
9
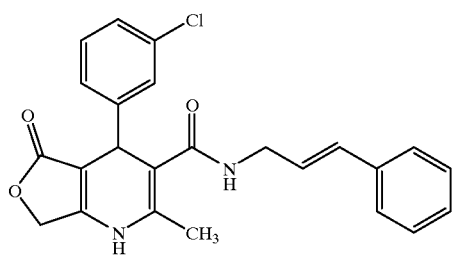
13
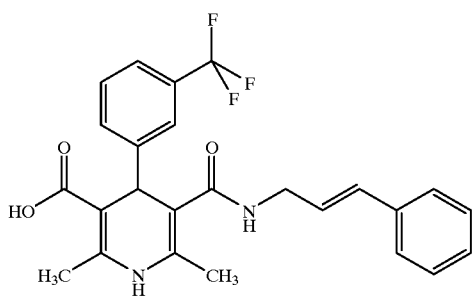
10
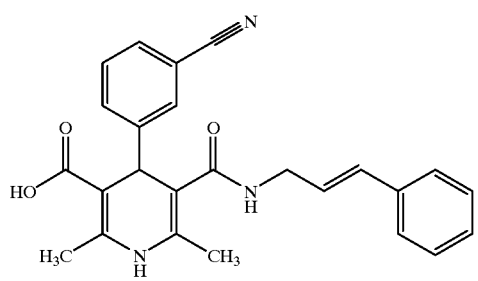
14
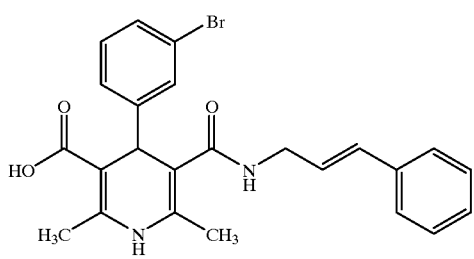

-continued
11
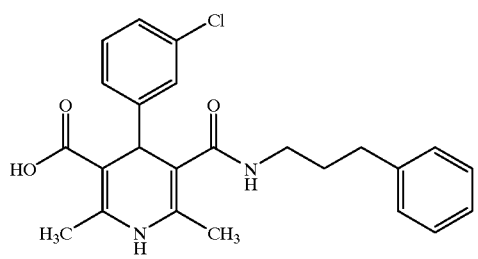
15
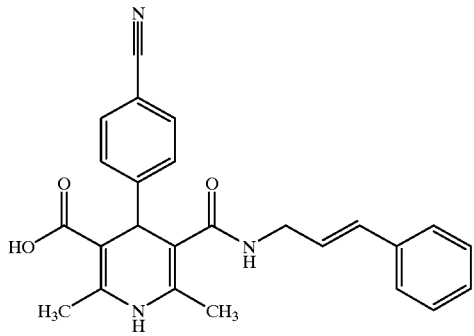
12
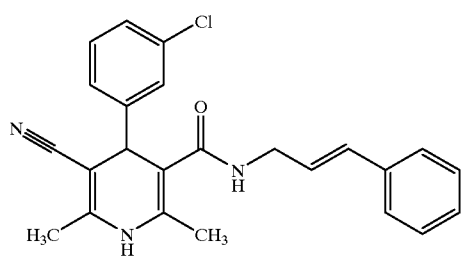
16
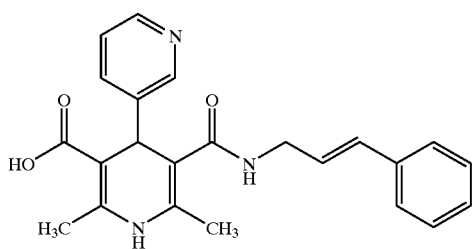
17
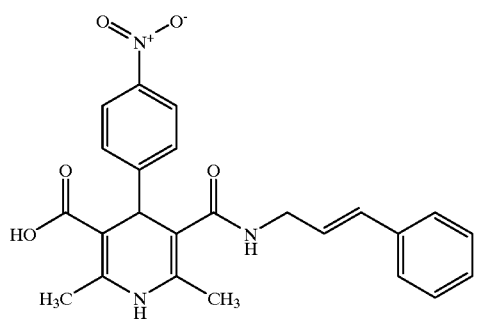
21
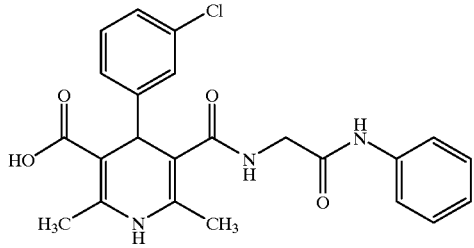
18
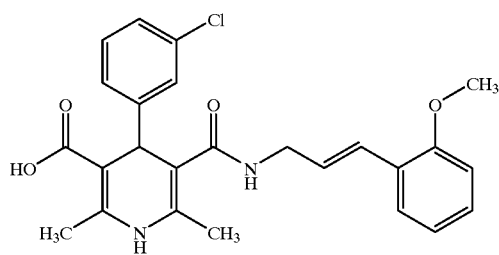
22
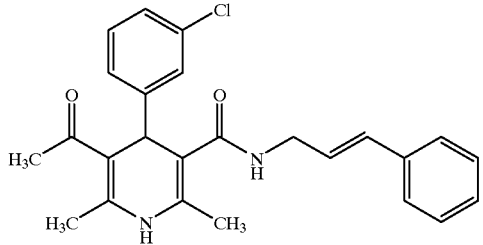
19
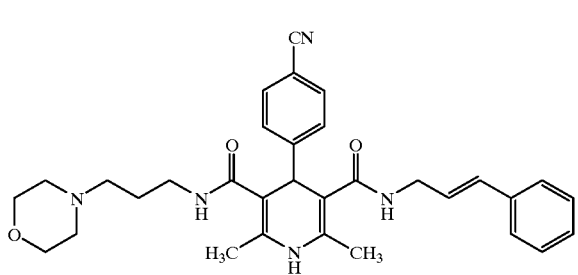
23
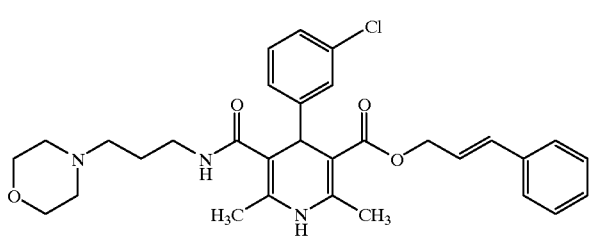

20
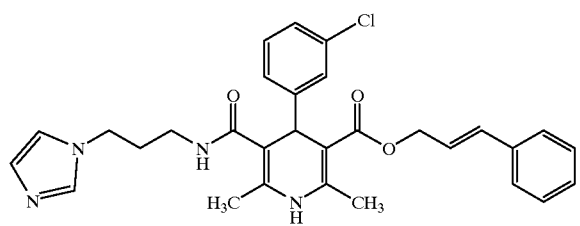
24
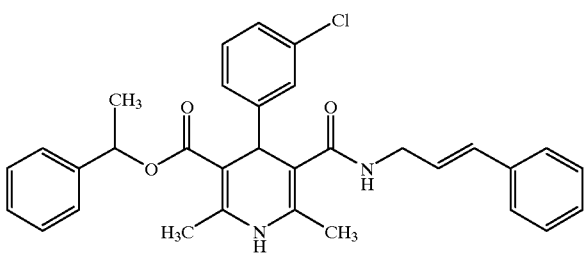
25
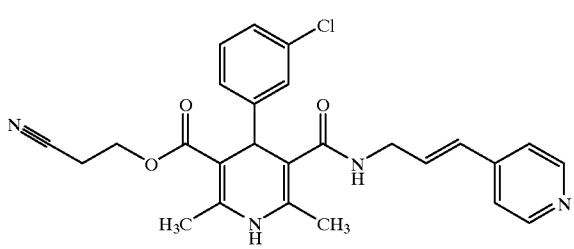
29
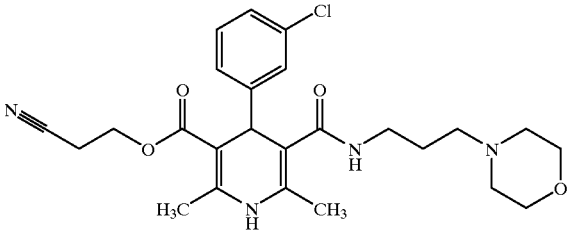
26
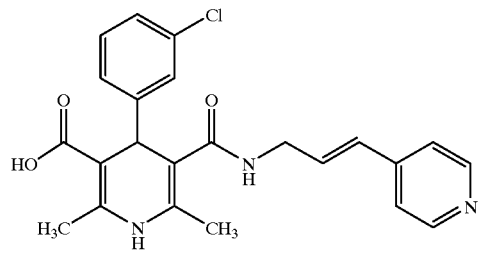
30
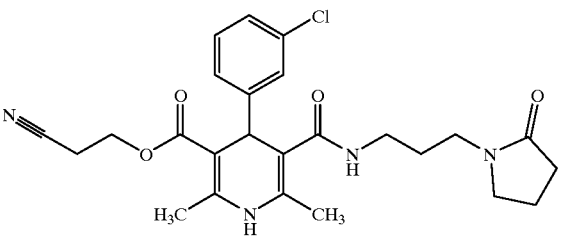
27
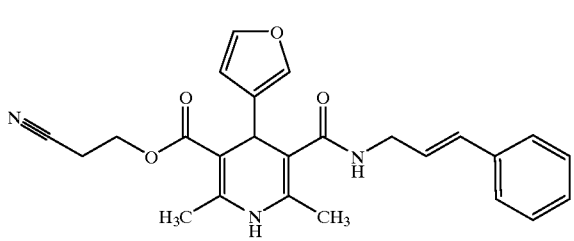
31
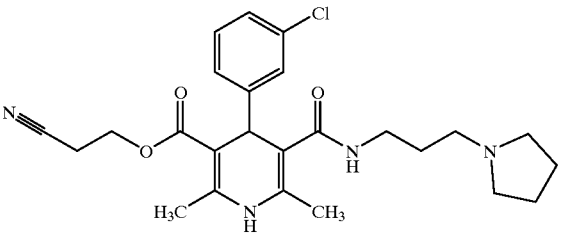
28
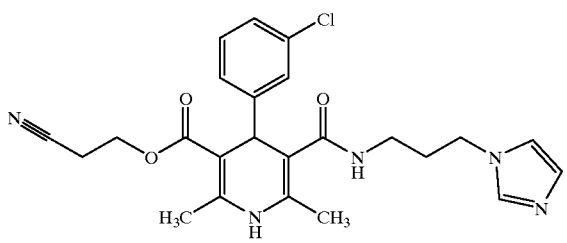
32
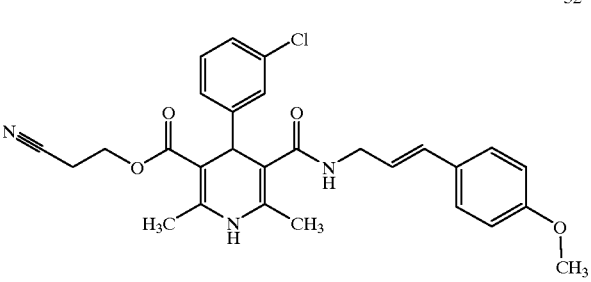
33
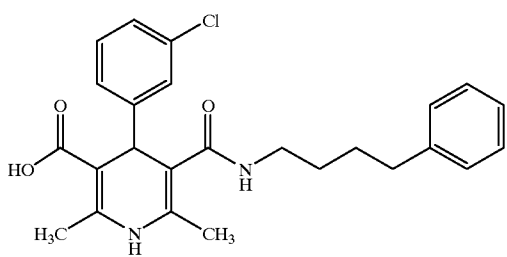
37
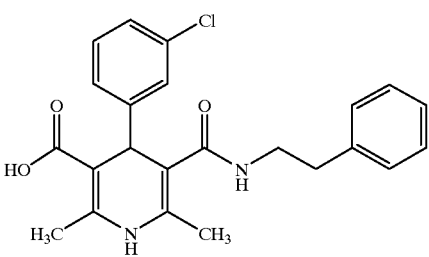

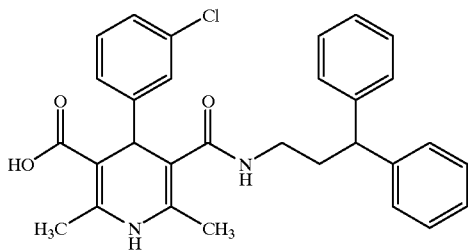

34

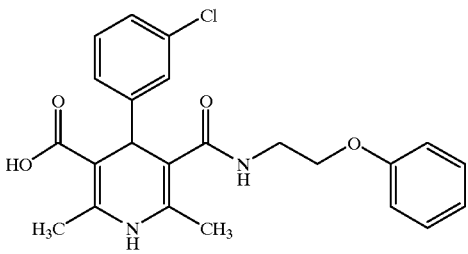

38

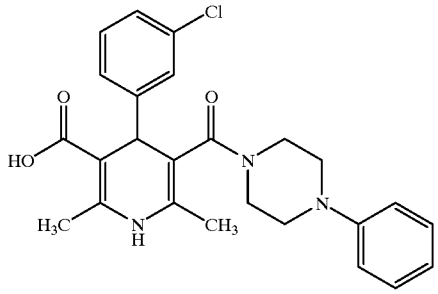

35

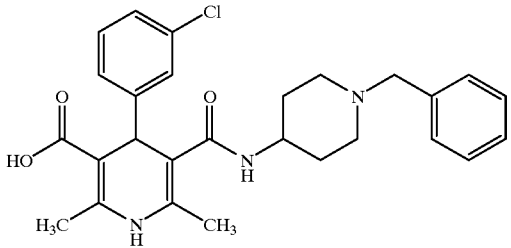

39

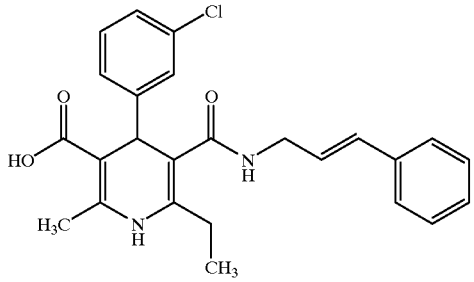

36

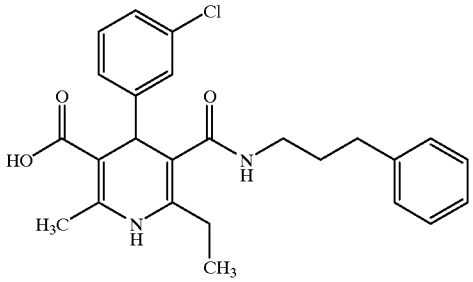

40

Test Example
Activity of Inhibiting the Action of L-type Calcium Channel

The activity of the dihydropyridine derivatives of the present invention to inhibit the action of L-type calcium channel was determined by the following method wherein the relaxation reaction on the KCl contraction of isolated thoracic aorta samples of rats was utilized.

1) Preparation of Isolated Thoracic Aorta Samples of Rats

The slips of thoracic aorta extracted from Wistar rats were used. Blood vessels were cut to form rings having a width of about 3 mm. The endothelial cells of the blood vessels were mechanically removed. The samples were suspended in a strain gauge in Tyrode solution (comprising 158.3 mM of NaCl, 4.0 mM of KCl, 15 mM of $MgCl_2$, 0.42 mM of $NaH_2PO_4$, 10 mM of $NaHCO_3$, 2 mM of $CaCl_2$ and 5 mM of glucose) in which a gaseous mixture of $O_2$ (95%) and $CO_2$ (5%) was introduced, to apply a stationary tension of 2 g. The tension of the blood vessel was recorded with a multipen recorder (Rikadenki Kogyo Co., Ltd.) by using a transducer after the amplification with a tension amplifier (EF-601G; Nihon Kohden Corporation). The experiments were conducted at 37° C.

2) Determination of Relaxation Reaction Against KCl contraction

After the tension was stabilized, the nutrient solution in the sample tank was replaced with High $K^+$ Tyrode solution (comprising 112.3 mM of NaCl, 50 mM of KCl, 1.05 mM of $MgCl_2$, 0.42 mM of $NaH_2PO_4$, 10 mM of $NaHCO_3$, 2 mM of $CaCl_2$ and 5 mM of glucose) to cause the contraction reaction. 30 minutes after, the solution in the sample tank was replaced with normal Tyrode solution. Then, the solution in the sample tank was again replaced with High $K^+$ Tyrode solution and the contraction reaction was observed. After the maximum contraction reaction occurred, a test compound was cumulatively added to realize concentrations of $10^{-9}$, $10^{-8}$, $10^{-7}$ and $10^{-6}$ M at intervals of 90 minutes. The inhibition rate of the test compound on the maximum contraction reaction was employed as the index of the activity of inhibiting the action of L-type calcium channel.

Test Example
Inhibition Activity of N-type Calcium Channel (Patch Clamp Method)

The activity of dihydropyridines derivatives of the present invention to the inhibition of N-type calcium channel was determined by the following method wherein the calcium electric currents in the cells of maxillary sympathetic ganglions of rats were detected by the whole cell voltage clamp method as described below.

1) Preparation of Cells of Maxillary Sympathetic Ganglions of Rats

The cervix of each of Wistar rats (2 to 4 weeks old) was opened to expose the maxillary ganglions under anesthesia with pentobarbital. A pair of the ganglions were removed and immediately washed with $Ca^{2+}$-free Tyrode solution cooled with ice. Each ganglion was cut into 3 or 4 pieces and kept in the $Ca^{2+}$-free Tyrode solution for 15 minutes. Then, these pieces were treated with papain [Washington Biochemicals (lot#35J557); 20 U/ml] for 20 minutes and then with a mixture of 2-type collagenase [Washington Biochemicals (CLS2); 5900 U/ml]and dispase [Calbiochem (lot#1312973); 16 mg/ml] for one hour. After enzymatic treatment, the ganglion cells were mechanically isolated by pipetting. The isolated ganglion cells were used for the experiments within 6 hours.

2) Determination of Calcium Electric Current

The calcium electric current was determined by the whole cell voltage clamp method under the fixed membrane potential. The pipette electrode was pulled from glass tube (inner diameter: 1.5 mm; Narishige) in two stage of a vertical pipette puller (PB-7; Narishige). The ionic current was amplified with a patch amplifier (CEZ-2300; Nihon Kohden Corporation). The noises were cut at 10 kHz (E-3201B, NF Electronic Instrument) and then the ionic current was monitored on a storage oscilloscope (DS-9121, Iwatsu) and, at the same time, recorded with a DAT data recorder (RD-120TE, TEAC). Then it was passed through a 1 kHz filter and recorded in a computer (Compaq DeskPro) with pCLAMP software (Axon Instrument) of 3 kHz. All the experiments were performed at room temperature (25±2° C.). In the measurement of the current through the calcium channel, 10 mM barium (composition of the solution: shown below) was used in place of calcium as the charge carrier. The transmission of barium through the calcium channel was higher than that of calcium in the sympathetic ganglion cells, and the calcium-dependent channel inactivation was slight when barium was used.

The test compounds were rapidly administered by Y-tube method by Murase et al. [Brain Res. 525, 84 (1990)]. Each compound was dissolved in DMSO preparing 10 mM mother solution. At the highest drug concentration used, the vehicle (0.1%) had no significant effect on the calcium electric current.

3) Solution Composition

Composition of Normal Tyrode's solution: NaCl; 143, KCl; 4, $MgCl_2$; 0.5; $CaCl_2$; 1.8, glucose; 5.5, $NaH_2PO_4$; 0.33, HEPES; 5 (Mm). The pH was adjusted to 7.4 with tris-OH.

Composition of Ca-free Tyrode's solution: the same as that of the Normal Tyrode's solution except that it was free of $CaCl_2$.

External solution for the determination of calcium electric current (mM): TEACl; 144, CsCl;. 4, $BaCl_2$; 1.8, $MgCl_2$; 0.53, glucose: 5.5, HEPES; 5 (pH 7.4)

Solution in patch electrode: CsCl; 140, $MgCl_2$; 5, $CaCl_2$ 0.28, HEPES; 10 (pH 7.2), EGTA; 5 (pH 7.2).

4) Results

The electric current was induced by the depolarization for 50 ms, from the holding potential of −60 mV to the test potential of 0 mV. This test potential was the peak in the current/voltage relationship, and the inhibition effect was examined at this point at which the error by the drift of the holding potential was reduced. As Tsein et al. reported, the maxillary ganglion cells were substantially free of L-type component (not more than 5%), and at least 85% thereof comprised the N-type component. After recording a calcium electric current for 5 continuous pulses, the test compound was cumulatively added with concentrations of 0.1, 1 and 10 uM. The pretreatment time for the compound of each concentration was 2 minutes.

Test Example
Activity of Inhibiting the Action of N-type Calcium Channel (Fluorescent Dye Method):

Human neuroblastoma cell IMR-32 was obtained from ATCC (American Type Culture Collection). The culture medium was prepared by adding 2 mM of L-glutamine (GIBCO), 1 mM of sodium pyruvate of pH 6.5 (GIBCO), a liquid antibiotic/antimicotic mixture (GIBCO) and 10% fetal calf serum (Cell Culture Technologies) to an Eagle minimum essential medium (GIBCO) free of Phenol Red and containing earle's salts supplyment. 3 ml of $1 \times 10^5$/ml IMR-32 cells was spread on a glass dish (Iwaki Glass Co., Ltd.) having a bottom diameter of 35 mm, which had been treated with poly-D-lysine (SIGMA) and also with collagen (COLLAGEN VITROGEN 100; a product of Collagen Co.). After the culture for 2 days, 1 mM (final concentration) of dibutyl cAMP and 2.5 μM of bromodeoxyuridine (SIGMA) were added to the culture mixture. After the culture for additional 10 to 14 days, the cells were used for the activity determination. The IMR-32 cell medium prepared as described above was replaced with Eagle minimum essential medium (GIBCO) containing 1 ml of 10 μM fura-2/AM (Dojin Kagaku Co.) and earle's salts supplyment but free of Phenol Red, and the incubation was conducted at 25° C. for one hour.

Then the medium was replaced with fura-2/AM-free Eagle minimum essential medium (GIBCO) free of Phenol Red and containing earle's salts supplyment. After conducting the incubation at 37° C. for one hour, the medium was replaced with a recording medium (comprising 20 mM of HEPES-KOH, 115 mM of NaCl, 5.4 mM of KCl, 0.8 mM of $MgCl_2$, 1.8 mM of $CaCl_2$ and 13.8 mM of D-glucose). The N-calcium channel inhibition activity was determined and analyzed with a fluorescent microscope (Nikon corporation) and an image analysis apparatus ARGUS 50 (Hamamatsu Photonics). Namely, a recording medium (comprising 20 mM of HEPES-KOH, 115 mM of NaCl, 5.4 mM of KCl, 0.8 mM of $MgCl_2$, 1.8 mM of $CaCl_2$ and 13.8 mM of D-glucose) containing 1 μM of Nifedipine was applied to the cells and refluxed by Y-tube method for 2 minutes. Then, a 60 mM potassium chloride-containing stimulating agent was rapidly given. Thereafter, 60 mM potassium chloride-containing stimulating agents which further contained 0.1, 1 or 10 μM of a test compound were rapidly and successively administered by Y-tube method to determine the channel inhibition activity. Finally, 60 mM potassium chloride-containing stimulating agent further containing 1 μM of omega conotoxin (Peptide Kenkyu-sho) was rapidly given by Y-tube method to realize 100% inhibition of the N-type calcium channel.

Table 1 shows the results of the determination of the activity of inhibiting the N-type calcium channel (with 0.1 μM of a dihydropyridine derivative) and also the activity of inhibiting the L-type calcium channel (with $10^{-7}$ M of a dihydropyridine derivative) by the patch clamp method. Table 2 shows the results of the determination of the activity of inhibiting the N-type calcium channel by the fluorescent dye method.

TABLE 1

| Example | N-type inhibition 0.1 uM (%) | L-type inhibition $10^{-7}$ M (%) | $IC_{50}$, nM |
|---|---|---|---|
| 1 | 35 | 19 | >1000 |
| 4 | 16 | −7 | 914 |
| 12 | 24 | 21 | 220 |
| 17 | 16 | −6 | >1000 |

TABLE 2

| Example | N-type inhibition pIC$_{50}$ |
|---------|------------------------------|
| 1 | 5.3 |
| 4 | 5.8 |
| 10 | 5.6 |
| 12 | 5.9 |
| 17 | 5.8 |
| 21 | 6.1 |
| 34 | 6.2 |

It is apparent from the above-described facts that the new dihydropyridine derivatives have an excellent activity of inhibiting the action of the N-type calcium channel.

The activity of inhibiting the L-type calcium channel of them was also examined to find that it was weak.

The new dihydropyridine derivatives of the present invention had the activity of selectively inhibit the action of the N-type calcium channel. Therefore, the new dihydropyridine derivatives of the present invention are usable for the treatment of encephalopathies caused by the ischemia in the acute phase after the onset of cerebral infarction, cerebral hemorrhage (including subarachnoidal bleeding) or the like; progressive neurodegenerative diseases; e. g. Alzheimer's disease; AIDS related dementia; Parkinson's disease; dementia caused by cerebrovascular disorders and ALS; neuropathy caused by head injury; sharp pain and a cold feeling caused by diabetes or thromboangitis obliterans; pain after an operation; various pains, e. g. migraine and visceral pain; bronchial asthma; various diseases caused by psychogenic stress, e. g. unstable angina and hypersensitive colon inflammation; emotional disorder; and drug addiction withdrawal symptoms, e. g. ethanol addiction withdrawal symptoms.

What is claimed is:

1. Dihydropyridine derivatives of following general formula (1) or pharmaceutically acceptable salts thereof:

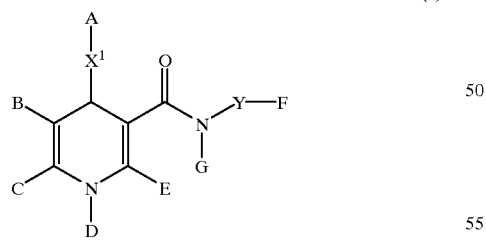

(1)

wherein

A represents a group of following general formula (2), 1-naphthyl group, 2-naphthyl group, thiophene-3-yl group, thiophene-2-yl group, furan-3-yl group, furan-2-yl group, pyridine-4-yl group, pyridine-3-yl group, pyridine-2-yl group, indole-2-yl group or indole-3-yl group:

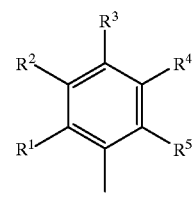

(2)

wherein $R^1$, $R^2$, $R^3$, $R^4$ and $R^5$ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group, B represents a cyano group, nitro group, acetyl group, tetrazole group, triazole group or a group of following general formula (3) or (4):

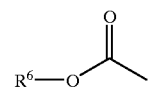

(3)

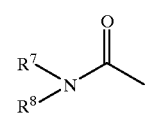

(4)

wherein $R^6$ to $R^8$ each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group excluding pyridine-3-ylpropyl group, a heteroaryl-lower alkenyl group, a cyano-lower alkyl group or a cyano-lower alkenyl group, and the chains in $R^6$ to $R^8$ may have a hetero atom, and $R^7$ and $R^8$ may together form a ring which may contain a hetero atom, C represents a hydrogen atom, a lower alkyl group, dimethoxymethyl group, cyano group, a hydroxy-lower alkyl group or a halogeno-lower alkyl group, D represents a hydrogen atom, a lower alkyl group, a hydroxy-lower alkyl group or an aryl-lower alkyl group, E represents a hydrogen atom, a lower alkyl group, dimethoxymethyl group, cyano group, a hydroxy-lower alkyl group or a halogeno-lower alkyl group, F represents an aryl group, a heteroaryl group or a cyclic alkyl group which may have a hetero atom, provided that the cyclic alkyl group which may have a hetero atom is not a piperidyl group, G represents a hydrogen atom or a lower alkyl group, $X^1$ represents an interatomic bond, —$CH_2$—, —$CH_2CH_2$—, CH=CH— or —C≡C—, and Y represents a group of any of following general formulae (5) to (14):

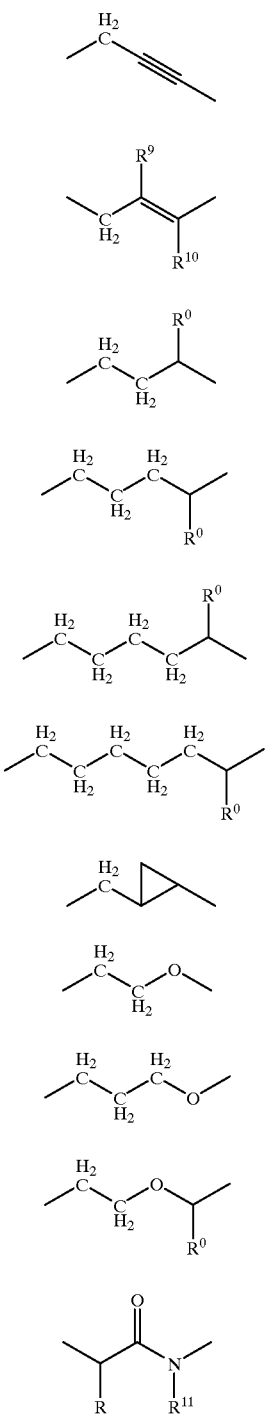

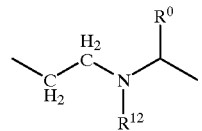

wherein $R^9$ to $R^{12}$ and $R^0$ may be the same or different from each other, and each represent hydrogen atom, a lower alkyl group, a hydroxy-lower alkyl group, a thio-lower alkyl group, an alkylthio-lower alkyl group, an aryl group, an aryl-lower alkyl group or a heteroaryl-lower alkyl group, and B and C may together form a lactone ring or lactam ring or two of $R^1$ to $R^3$ may be bonded together to form a ring, and $R^9$ and $R^{10}$ may be bonded together to form a ring.

2. The dihydropyridine derivatives or pharmaceutically acceptable salts thereof stated in claim 1, wherein F in general formula (1) is a group of following formula (15), thiophene-3-yl group, thiophene-2-yl group, furan-3-yl group, furan-2-yl group, pyridine-4-yl group, pyridine-3-yl group, pyridine-2-yl group, cyclohexyl group, pyrrolidine-1-yl group, morpholine-4-yl group, imidazole-1-yl group or pyrrolidinone-1-yl group:

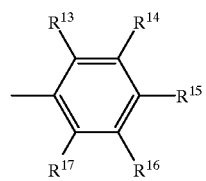

wherein $R^{13}$, $R^{14}$, $R^{15}$, $R^{16}$ and $R^{17}$ may be the same or different from each other, and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, carbamoyl which may have a substituent, a carboxyamide group which may have a substituent, an aroyl group, an aryl group, a heteroaryl group or a saturated cyclic hydrocarbon group having 3 to 8 carbon atoms, which may have a hetero atom in its chain if necessary; and two of $R^{13}$ to $R^{15}$ may be bonded together to form a ring.

3. The dihydropyridine derivatives or pharmaceutically acceptable salts thereof stated in claim 1, wherein Y represents a group represented by general formula (6).

4. The dihydropyridine derivatives or pharmaceutically acceptable salts thereof stated in claim 1, wherein D represents hydrogen atom, G represents hydrogen atom, $X^1$ represents an interatomic bond, and Y represents a group represented by general formula (6) wherein $R^9$ to $R^{10}$ each represent hydrogen atom.

5. The dihydropyridine derivatives or pharmaceutically acceptable salts thereof stated in claim 1, wherein B represents a group represented by general formula (3) or a group represented by general formula (4) wherein either $R^7$ or $R^8$ represents hydrogen atom or B is condensed with C to form a lactone ring, D represents hydrogen atom, G represents hydrogen atom, $X^1$ represents an interatomic bond, and Y represents a group represented by general formula (6) wherein $R^9$ to $R^{10}$ each represent hydrogen atom.

6. The dihydropyridine derivatives or pharmaceutically acceptable salts thereof stated in claim 1, wherein B represents a group represented by general formula (3) wherein $R^6$ represents hydrogen atom, D represents hydrogen atom, G represents hydrogen atom, $X^1$ represents an interatomic bond, and Y represents a group represented by general formula (6) wherein $R^9$ and $R^{10}$ each represent hydrogen atom.

7. The dihydropyridine derivatives or pharmaceutically acceptable salts thereof stated in claim 2, wherein B represents a group represented by general formula (3) wherein $R^6$ represents hydrogen atom or a group represented by general formula (4) wherein either $R^7$ or $R^8$ represents hydrogen atom, D represents hydrogen atom, G represents hydrogen atom, $X^1$ represents an interatomic bond, and Y represents a group represented by general formula (7).

8. The dihydropyridine derivatives or pharmaceutically acceptable salts thereof stated in claim 7, wherein B represents a group represented by general formula (3) wherein $R^6$ represents hydrogen atom.

9. The dihydropyridine derivatives or pharmaceutically acceptable salts thereof stated in claim 2, wherein B represents a group represented by general formula (3) wherein $R^6$ represents a group other than hydrogen atom, D represents hydrogen atom, G represents hydrogen atom, $X^1$ represents an interatomic bond, and Y represents a group represented by general formula (7).

10. The dihydropyridine derivatives or pharmaceutically acceptable salts thereof stated in claim 2, wherein B represents a group represented by general formula (3) wherein $R^6$ represents an aryl-lower alkenyl group, a heteroaryl-lower alkenyl group or a cyano-lower alkyl group. D represents hydrogen atom, G represents hydrogen atom, $X^1$ represents an interatomic bond, and Y represents a group represented by general formula (7).

11. The dihydropyridine derivatives or pharmaceutically acceptable salts thereof stated in claim 1, wherein A represents a group represented by general formula (2), B represents a group represented by general formula (3) wherein $R^6$ represents hydrogen atom, D represents hydrogen atom, F represents a group represented by general formula (15), G represents hydrogen atom, $X^1$ represents an interatomic bond, and Y is a group represented by general formula (6) wherein $R^9$ to $R^{10}$ each represent hydrogen atom.

12. The dihydropyridine derivatives or pharmaceutically acceptable salts thereof stated in claim 11, wherein C represents methyl group and E represents methyl group.

13. Dihydropyridine derivatives of following general formula (16) or pharmaceutically acceptable salts thereof:

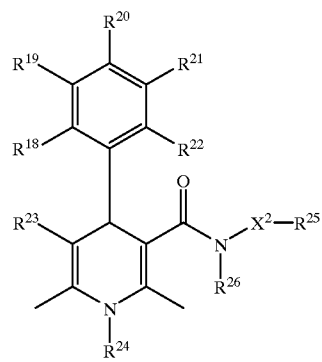

(16)

wherein $R^{18}$, $R^{19}$, $R^{20}$, $R^{21}$ and $R^{22}$ may be the same or different from each other, and each represent hydrogen atom, a halogen atom, hydroxyl group, amino group, cyano group, nitro group, a lower alkyl group, a lower alkoxyl group, a lower alkenyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkoxyl group or an aroyl group, $R^{23}$ represents carboxyl group, carbamoyl group, cyano group or a group of following general formula (17):

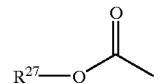

(17)

wherein $R^{27}$ represents a linear, branched or cyclic, saturated or unsaturated hydrocarbon group having 1 to 6 carbon atoms which may contain an oxygen atom in the chain, $R^{24}$ represents a hydrogen atom, a lower alkyl group, a hydroxy-lower alkyl group or an aryl-lower alkyl group, $R^{25}$ represents a substituted or unsubstituted aryl group, a substituted or unsubstituted heteroaryl group or a cyclic alkyl group, provided that the cyclic alkyl group is not a piperidyl group, $R^{26}$ represents a hydrogen atom or a lower alkyl group, $X^2$ represents a group of any of following general formulae (18) to (21):

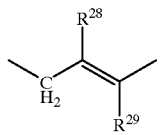

(18)

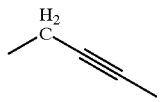

(19)

-continued (20)

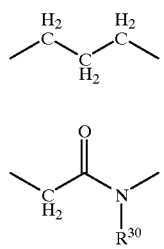

(21)

wherein $R^{28}$ to $R^{30}$ may be the same or different from each other, and each represent hydrogen atom or a lower alkyl group, and two of $R^{18}$ to $R^{20}$ may be bonded together to form a ring.

14. The dihydropyridine derivatives or pharmaceutically acceptable salts thereof stated in claim 13, wherein $R^{24}$, $R^{28}$ and $R^{29}$ each represent hydrogen atom, and $X^2$ represents a group of formula (18).

15. A method of inhibiting N-type calcium channels, comprising administering to a subject in need thereof an effective amount of a dihydropyridine derivative or a pharmaceutically acceptable salt thereof as recited in claim 1.

16. A method of inhibiting N-type calcium channels, comprising administering to a subject in need thereof an effective amount of a dihydropyridine derivative or a pharmaceutically acceptable salt thereof as recited in claim 13.

17. A method of treating encephalopathies caused by the ischemia in the acute phase after the onset of cerebral infarction or cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine, visceral pain, bronchial asthma, unstable angina, hypersensitive colon inflammation, and drug addiction withdrawal symptoms, comprising administering to a subject in need thereof an effective amount of a dihydropyridine derivative or a pharmaceutically acceptable salt thereof as recited in claim 1.

18. A method of treating encephalopathies caused by the ischemia in the acute phase after the onset of cerebral infarction or cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine, visceral pain, bronchial asthma, unstable angina, hypersensitive colon inflammation, and drug addiction withdrawal symptoms, comprising administering to a subject in need thereof an effective amount of a dihydropyridine derivative or a pharmaceutically acceptable salt thereof as recited in claim 13.

19. A pharmaceutical composition, comprising the dihydropyridine derivative or pharmaceutically acceptable salt thereof as recited in claim 1 and a pharmaceutically acceptable carrier or diluent.

20. A pharmaceutical composition, comprising the dihydropyridine derivative or pharmaceutically acceptable salt thereof as recited in claim 13 and a pharmaceutically acceptable carrier or diluent.

21. A method of inhibiting N-type calcium channels, comprising administering to a subject in need thereof an effective amount of a dihydropyridine derivative of following general formula (1-1) or a pharmaceutically acceptable salt thereof:

(1-1)

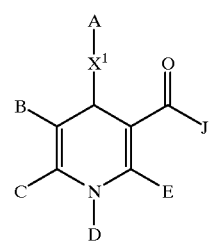

wherein

A represents a group of following general formula (2), 1-naphthyl group, 2-naphthyl group, thiophene-3-yl group, thiophene-2-yl group, furan-3-yl group, furan-2-yl group, pyridine-4-yl group, pyridine-3-yl group, pyridine-2-yl group, indole-2-yl group, indole-3-yl group, quinoline-2-yl group, quinoline-3-yl group, quinoline-4-yl group, quinoline-5-yl group, quinoline-6-yl group, quinoline-7-yl group, quinoline-8-yl group, another heteroaryl group, cyclohexyl group, cyclopentyl group or another cyclic alkyl group which may have a hetero atom in its group:

(2)

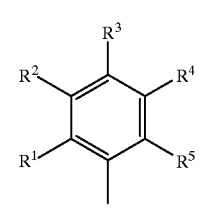

wherein $R^1$, $R^2$, $R^3$, $R^4$ and $R^5$ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group, B represents a cyano group, nitro group, acetyl group, tetrazole group, triazole group or a group of following general formula (3) or (4):

(3)

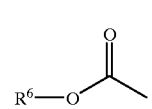

(4)

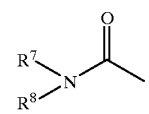

wherein $R^6$ to $R^8$ each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains in $R^6$ to $R^8$ may have a hetero atom, and $R^7$ and $R^8$ may together form a ring which may contain a hetero atom, C represents a hydrogen atom, dimethoxymethyl group, cyano group, a lower alkyl group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group, D represents a hydrogen atom, a lower alkyl group, a hydroxy lower alkyl group or an aryl-lower alkyl group, E represents a hydrogen atom, dimethoxymethyl group, cyano group, a lower alkyl group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group, $X^1$ represents an interatomic bond, —$CH_2$—, —$CH_2CH_2$—, CH=CH— or —C≡C—, J represents a group of any of following formulae (J-1) to (J-3):

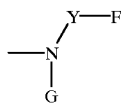
(J-1)

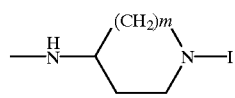
(J-2)

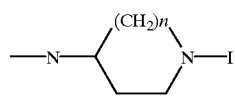
(J-3)

wherein

F in formula (J-1) represents an aryl group, a heteroaryl group or a cyclic alkyl group which may contain a hetero atom, G represents hydrogen atom or a lower alkyl group, Y represents a group of any of following general formulae (5) to (14), (22) and (23):

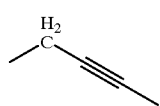
(5)

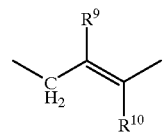
(6)

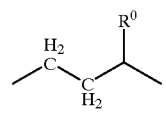
(7)

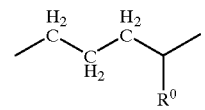
(8)-1

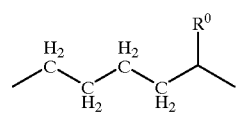
(8)-2

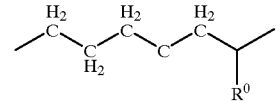
(8)-3

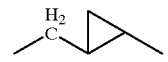
(9)

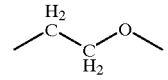
(10)

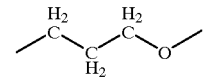
(11)

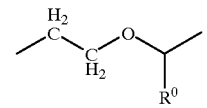
(12)

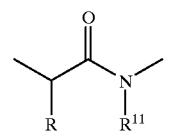
(13)

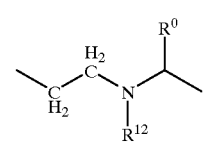
(14)

(22)

-continued

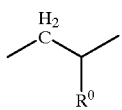
(23)

wherein $R^9$ to $R^{12}$, R and $R^0$ may be the same or different from each other, and each represent hydrogen atom, a lower alkyl group, a hydroxy-lower alkyl group, a thio-lower alkyl group, an alkylthio-lower alkyl group, an aryl group, an aryl-lower alkyl group or a heteroaryl-lower alkyl group, and, in formulae (J-2) and (J-3), m represents an integer of 1 to 3, n represents an integer of 2 or 3, I represents an aryl group, a heteroaryl group, a cyclic alkyl group which may contain a hetero atom or a group of following formula (Ia):

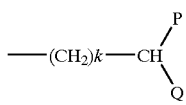
(Ia)

wherein k is 0, 1 or 2, P and Q may be the same or different from each other, and each represent a hydrogen atom, a lower alkyl group, a hydroxy-lower alkyl group, a thio-lower alkyl group, an alkylthio-lower alkyl group, an aryl group, an aryl-lower alkyl group, a heteroaryl group or a heteroaryl-lower alkyl group, or P and Q together form a ring which may contain a hetero atom, and B and C may together form a lactone ring or lactam ring or two of $R^1$ to $R^3$ may be bonded together to form a ring, and $R^9$ and $R^{10}$ may be bonded together to form a ring.

22. The method of claim 21, wherein J represents a group of formula (J-1).

23. The method of claim 22, wherein F represents a group of following formula (15), thiophene-3-yl group, thiophene-2-yl group, furan-3-yl group, furan-2-yl group, pyridine-4-yl group, pyridine-3-yl group, pyridine-2-yl group, imidazole-1-yl group, another heteroaryl group, piperidine-1-yl group, piperidine-4-yl group, pyrrolidine-1-yl group, pyrrolidine-3-yl group, piperidinone-1-yl group, pyrrolidinone-1-yl group, piperazine-1-yl group, morpholine-4-yl group, cyclohexyl group, cyclopentyl group or a cyclic alkyl group having 3 to 8 carbon atoms:

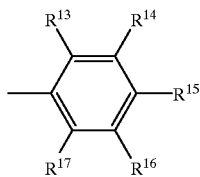
(15)

wherein $R^{13}$, $R^{14}$, $R^{15}$, $R^{16}$ and $R^{17}$ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, carbamoyl group which may have a substituent, a carboxyamide group which may have a substituent, an aroyl group, an aryl group, a heteroaryl group or a saturated cyclic hydrocarbon group having 3 to 8 carbon atoms, which may have a hetero atom in its chain if necessary.

24. A method of treating encephalopathies caused by the ischemia in the acute phase after the onset of cerebral infarction or cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine, visceral pain, bronchial asthma, unstable angina, hypersensitive colon inflammation, and drug addiction withdrawal symptoms, comprising administering to a subject in need thereof an effective amount of a dihydropyridine derivative represented by the following formula (1-1) or pharmaceutically acceptable salt thereof:

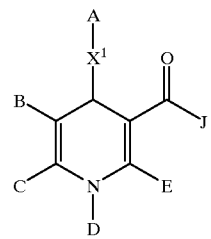
(1-1)

wherein

A represents a group of following general formula (2), 1-naphthyl group, 2-naphthyl group, thiophene-3-yl group, thiophene-2-yl group, furan-3-yl group, furan-2-yl group, pyridine-4-yl group, pyridine-3-yl group, pyridine-2-yl group, indole-2-yl group, indole-3-yl group, quinoline-2-yl group, quinoline-3-yl group, quinoline-4-yl group, quinoline-5-yl group, quinoline-6-yl group, quinoline-7-yl group, quinoline-8-yl group, another heteroaryl group, cyclohexyl group, cyclopentyl group or another cyclic alkyl group which may have a hetero atom in its group:

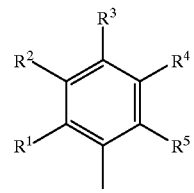
(2)

wherein $R^1$, $R^2$, $R^3$, $R^4$ and $R^5$ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group, B represents a cyano group, nitro group, acetyl group, tetrazole group, triazole group or a group of following general formula (3) or (4):

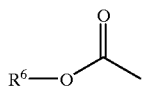

(3)

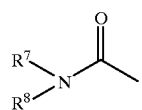

(4)

wherein $R^6$ to $R^8$ each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains in $R^6$ to $R^8$ may have a hetero atom, and $R^7$ and $R^8$ may together form a ring which may contain a hetero atom, C represents a hydrogen atom, dimethoxymethyl group, cyano group, a lower alkyl group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group, D represents a hydrogen atom, a lower alkyl group, a hydroxy lower alkyl group or an aryl-lower alkyl group, E represents a hydrogen atom, dimethoxymethyl group, cyano group, a lower alkyl group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group, $X^1$ represents an interatomic bond, —CH$_2$—, —CH$_2$CH$_2$—, CH═CH— or —C≡C—, J represents a group of any of following formulae (J-1) to (J-3):

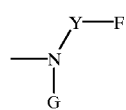

(J-1)

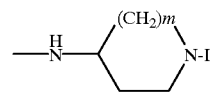

(J-2)

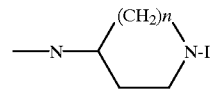

(J-3)

wherein

F in formula (J-1) represents an aryl group, a heteroaryl group or a cyclic alkyl group which may contain a hetero atom, G represents a hydrogen atom or a lower alkyl group, Y represents a group of any of following general formulae (5) to (14), (22) and (23):

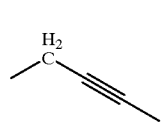

(5)

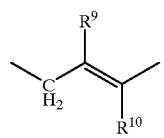

(6)

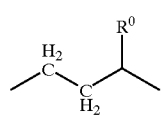

(7)

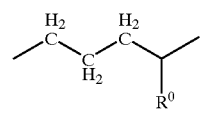

(8)-1

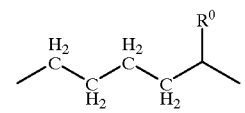

(8)-2

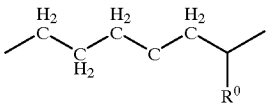

(8)-3

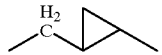

(9)

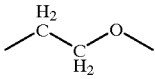

(10)

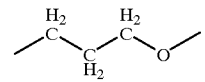

(11)

(12)
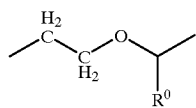

(13)
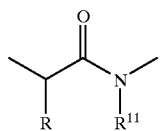

(14)
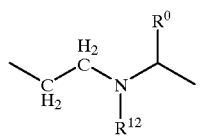

(22)

(23)
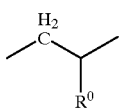

wherein $R^9$ to $R^{12}$, R and $R^0$ may be the same or different from each other, and each represent hydrogen atom, a lower alkyl group, a hydroxy-lower alkyl group, a thio-lower alkyl group, an alkylthio-lower alkyl group, an aryl group, an aryl-lower alkyl group or a heteroaryl-lower alkyl group, and, in formulae (J-2) and (J-3), m represents an integer of 1 to 3, n represents an integer of 2 or 3, I represents an aryl group, a heteroaryl group, a cyclic alkyl group which may contain a hetero atom or a group of following formula (Ia):

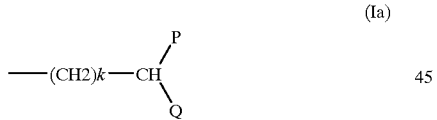
(Ia)

wherein k is 0, 1 or 2, P and Q may be the same or different from each other, and each represent a hydrogen atom, a lower alkyl group, a hydroxy-lower alkyl group, a thio-lower alkyl group, an alkylthio-lower alkyl group, an aryl group, an aryl-lower alkyl group, a heteroaryl group or a heteroaryl-lower alkyl group, or P and Q together form a ring which may contain a hetero atom, and B and C may together form a lactone ring or lactam ring or two of $R^1$ to $R^3$ may be bonded together to form a ring, and $R^9$ and $R^{10}$ may be bonded together to form a ring.

25. The method of claim 24, wherein J represents a group of formula (J-1).

26. The method of claim 25, wherein F represents a group of following formula (15), thiophene-3-yl group, thiophene-2-yl group, furan-3-yl group, furan-2-yl group, pyridine-4-yl group, pyridine-3-yl group, pyridine-2-yl group, imidazole-1-yl group, another heteroaryl group, piperidine-1-yl group, piperidine-4-yl group, pyrrolidine-1-yl group, pyrrolidine-3-yl group, piperidinone-1-yl group, pyrrolidinone-1-yl group, piperazine-1-yl group, morpholine-4-yl group, cyclohexyl group, cyclopentyl group or a cyclic alkyl group having 3 to 8 carbon atoms:

(15)
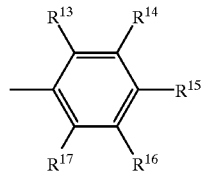

wherein $R^{13}$, $R^{14}$, $R^{15}$, $R^{16}$ and $R^{17}$ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, carbamoyl group which may have a substituent, a carboxyamide group which may have a substituent, an aroyl group, an aryl group, a heteroaryl group or a saturated cyclic hydrocarbon group having 3 to 8 carbon atoms, which may have a hetero atom in its chain if necessary.

27. A method of treating bronchial asthma, unstable angina, or hypertensive colon inflammation, comprising administering to a subject in need thereof an effective amount of a dihydropyridine derivative represented by formula (1-1) or a pharmaceutically acceptable salt thereof:

(1-1)
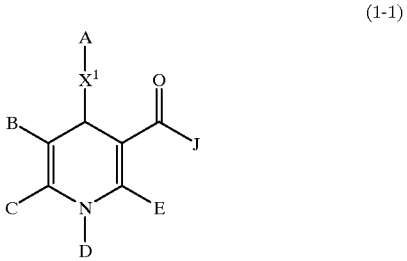

wherein

A represents a group of following general formula (2), 1-naphthyl group, 2-naphthyl group, thiophene-3-yl group, thiophene-2-yl group, furan-3-yl group, furan-2-yl group, pyridine-4-yl group, pyridine-3-yl group, pyridine-2-yl group, indole-2-yl group, indole-3-yl group, quinoline-2-yl group, quinoline-3-yl group, quinoline-4-yl group, quinoline-5-yl group, quinoline-6-yl group, quinoline-7-yl group, quinoline-8-yl group, another heteroaryl group, cyclohexyl group, cyclopentyl group or another cyclic alkyl group which may have a hetero atom in its group:

(2)

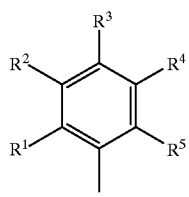

wherein R¹, R², R³, R⁴ and R⁵ may be the same or different from each other, and each represent hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a lower alkoxycarbonyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl group, a heteroaryl group, an aryl-lower alkoxyl group or an aroyl group, B represents a cyano group, nitro group, acetyl group, tetrazole group, triazole group or a group of following general formula (3) or (4):

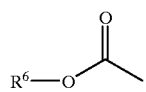
(3)

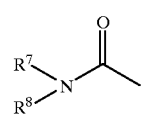
(4)

wherein R⁶ to R⁸ each represent hydrogen atom, a linear, branched or cyclic, saturated or unsaturated hydrocarbon group having 1 to 6 carbon atoms, an alkyl group substituted with a cyclic alkyl group which may contain a hetero atom, a substituted or unsubstituted aryl group, a substituted or unsubstituted heteroaryl group, a hydroxy-lower alkyl group, a hydroxy-lower alkenyl group, a halogeno-lower alkyl group, a halogeno-lower alkenyl group, an aryl-lower alkyl group, an aryl-lower alkenyl group, a heteroaryl-lower alkyl group, a heteroaryl-lower alkenyl group, a cyano-lower alkyl group or a cyano-lower alkenyl group, and the chains in R⁶ to R⁸ may have a hetero atom, and R⁷ and R⁸ may together form a ring which may contain a hetero atom, C represents a hydrogen atom, dimethoxymethyl group, cyano group, a lower alkyl group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group, D represents a hydrogen atom, a lower alkyl group, a hydroxy lower alkyl group or an aryl-lower alkyl group, E represents a hydrogen atom, dimethoxymethyl group, cyano group, a lower alkyl group, a hydroxy-lower alkyl group, a halogeno-lower alkyl group, an amino-lower alkyl group, an azido-lower alkyl group, an aryl group, a heteroaryl group, an aryl-lower alkyl group or a heteroaryl-lower alkyl group, $X^1$ represents an interatomic bond, —$CH_2$—, —$CH_2CH_2$—, CH=CH— or —C≡C—, J represents a group of any of following formulae (J-1) to (J-3):

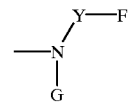
(J-1)

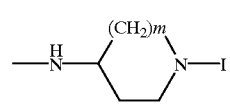
(J-2)

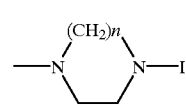
(J-3)

wherein

F in formula (J-1) represents an aryl group, a heteroaryl group or a cyclic alkyl group which may contain a hetero atom, G represents hydrogen atom or a lower alkyl group, Y represents a group of any of following general formulae (5) to (14), (22) and (23):

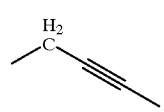
(5)

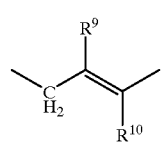
(6)

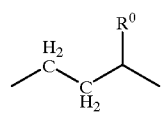
(7)

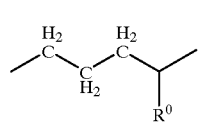
(8)-1

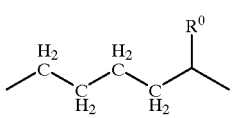
(8)-2

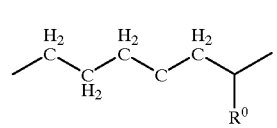
(8)-3

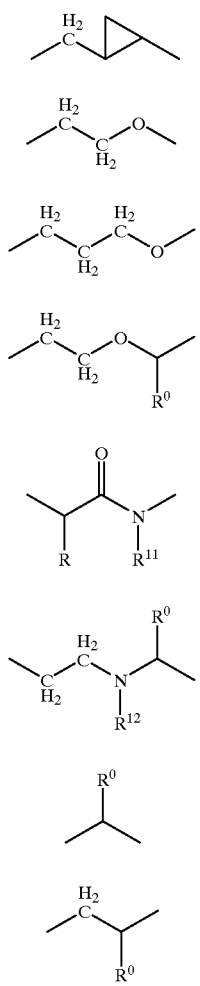

(9)
(10)
(11)
(12)
(13)
(14)
(22)
(23)

wherein $R^9$ to $R^{12}$, R and $R^0$ may be the same or different from each other, and each represent hydrogen atom, a lower alkyl group, a hydroxy-lower alkyl group, a thio-lower alkyl group, an alkylthio-lower alkyl group, an aryl group, an aryl-lower alkyl group or a heteroaryl-lower alkyl group, and, in formulae (J-2) and (J-3), m represents an integer of 1 to 3, n represents an integer of 2 or 3, I represents an aryl group, a heteroaryl group, a cyclic alkyl group which may contain a hetero atom or a group of following formula (Ia):

wherein k is 0, 1 or 2, P and Q may be the same or different from each other, and each represent hydrogen atom, a lower alkyl group, a hydroxy-lower alkyl group, a thio-lower alkyl group, an alkylthio-lower alkyl group, an aryl group, an aryl-lower alkyl group, a heteroaryl group or a heteroaryl-lower alkyl group, or P and Q together form a ring which may contain a hetero atom, and B and C may together form a lactone ring or lactam ring or two of $R^1$ to $R^3$ may be bonded together to form a ring, and $R^9$ and $R^{10}$ may be bonded together to form a ring.

28. The method of claim 27, wherein J represents a group of formula (J-1).

29. The method of claim 28, wherein F represents a group of following formula (15), thiophene-3-yl group, thiophene-2-yl group, furan-3-yl group, furan-2-yl group, pyridine-4-yl group, pyridine-3-yl group, pyridine-2-yl group, imidazole-1-yl group, another heteroaryl group, piperidine-1-yl group, piperidine-4-yl group, pyrrolidine-1-yl group, pyrrolidine-3-yl group, piperidinone-1-yl group, pyrrolidinone-1-yl group, piperazine-1-yl group, morpholine-4-yl group, cyclohexyl group, cyclopentyl group or a cyclic alkyl group having 3 to 8 carbon atoms:

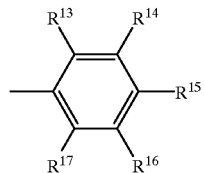

(15)

wherein $R^{13}$, $R^{14}$, $R^{15}$, $R^{16}$ and $R^{17}$ may be the same or different from each other, and each represent a hydrogen atom, a halogen atom, hydroxyl group, carboxyl group, amino group, cyano group, nitro group, a lower alkyl group, a lower alkoxyl group, a lower alkenyl group, a lower alkynyl group, a lower alkylamino group, a lower alkylthio group, a lower alkanoyl group, a hydroxy-lower alkyl group, a hydroxy-lower alkoxyl group, a hydroxy-lower alkenyl group, a halogeno-lower alkyl group, a halogeno-lower alkoxyl group, a halogeno-lower alkenyl group, an aryl-lower alkyl group, an aryl-lower alkoxyl group, a lower alkoxycarbonyl group, carbamoyl group which may have a substituent, a carboxyamide group which may have a substituent, an aroyl group, an aryl group, a heteroaryl group or a saturated cyclic hydrocarbon group having 3 to 8 carbon atoms, which may have a hetero atom in its chain if necessary.

30. A method of treating encephalopathies caused by the ischemia in the acute phase after the onset of cerebral infarction or cerebral hemorrhage, Alzheimer's disease, AIDS related dementia, Parkinson's disease, progressive neurodegenerative disease, neuropathy caused by head injury, sharp pain caused by thromboangitis obliterans, pain after an operation, migraine, visceral pain, bronchial asthma, unstable angina, hypersensitive colon inflammation, and drug addiction withdrawal symptoms, comprising administering to a subject in need thereof an effective amount of a dihydropyridine derivative or a pharmaceutically acceptable salt thereof as recited in claim 3.

31. A method of treating encephalopathies caused by the ischemia in the acute phase after the onset of cerebral infarction or cerebral hemorrhage, neuropathy caused by head injury, sharp pain caused by thromboangitis obliterans, pain after an operation, migraine, or visceral pain, comprising administering to a subject in need thereof an effective amount of a dihydropyridine derivative or a pharmaceutically acceptable salt thereof as recited in claim 1.

32. A method of treating encephalopathies caused by the ischemia in the acute phase after the onset of cerebral infarction or cerebral hemorrhage, neuropathy caused by head injury, sharp pain caused by thromboangitis obliterans, pain after an operation, migraine, or visceral pain, comprising administering to a subject in need thereof an effective amount of a dihydropyridine derivative or a pharmaceutically acceptable salt thereof as recited in claim 13.

33. The method of claim 31, which is a method of treating encephalopathies caused by the ischemia in the acute phase after the onset of cerebral infarction or cerebral hemorrhage.

34. The method of claim 31, which is a method of treating neuropathy caused by head injury.

35. The method of claim 31, which is a method of treating sharp pain caused by thromboangitis obliterans.

36. The method of claim 31, which is a method of treating pain after an operation, migraine, or visceral pain.

37. The method of claim 32, which is a method of treating encephalopathies caused by the ischemia in the acute phase after the onset of cerebral infarction or cerebral hemorrhage.

38. The method of claim 32, which is a method of treating neuropathy caused by head injury.

39. The method of claim 32, which is a method of treating sharp pain caused by thromboangitis obliterans.

40. The method of claim 32, which is a method of treating pain after an operation, migraine, or visceral pain.

* * * * *